US010709665B2

(12) United States Patent
Garcia et al.

(10) Patent No.: US 10,709,665 B2
(45) Date of Patent: Jul. 14, 2020

(54) ZINC MELOXICAM COMPLEX MICROPARTICLE MULTIVESICULAR LIPOSOME FORMULATIONS AND PROCESSES FOR MAKING THE SAME

(71) Applicant: Pacira Pharmaceuticals, Inc., San Diego, CA (US)

(72) Inventors: Louie Daniel Garcia, San Diego, CA (US); Stephanie Kurz, San Diego, CA (US); Soroush Ardekani, San Diego, CA (US); Kathleen Dunne Albright Los, San Diego, CA (US); Katherine Stone, San Diego, CA (US); Ernest G. Schutt, San Diego, CA (US); Vladimir Kharitonov, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 15/816,916

(22) Filed: Nov. 17, 2017

(65) Prior Publication Data
US 2018/0161275 A1 Jun. 14, 2018

Related U.S. Application Data

(60) Provisional application No. 62/424,274, filed on Nov. 18, 2016.

(51) Int. Cl.
*A61K 9/127* (2006.01)
*A61K 31/555* (2006.01)
(Continued)

(52) U.S. Cl.
CPC .......... *A61K 9/1277* (2013.01); *A61K 9/0019* (2013.01); *A61K 9/127* (2013.01);
(Continued)

(58) Field of Classification Search
CPC .... A61K 9/1277; A61K 47/24; A61K 31/555; A61K 9/127; A61K 9/0019; A61P 29/00
See application file for complete search history.

(56) References Cited

U.S. PATENT DOCUMENTS 3,547,119 A 12/1970 Hall et al.
4,311,137 A 1/1982 Gerard
(Continued)

FOREIGN PATENT DOCUMENTS

CN 101744764 6/2010
EP 0 280 503 4/1993
(Continued)

OTHER PUBLICATIONS

Culita et al., Apr. 2012, Evaluation of cytotoxic and antiproliferative activity of Co(II), Ni(II), Cu(II) and Zn(ii) complexes with meloxicam on virus—transformed tumor cells, Revista de Chemie-Bucharest, 63(4):384-389.
(Continued)

*Primary Examiner* — Gollamudi S Kishore
(74) *Attorney, Agent, or Firm* — Knobbe, Martens, Olson & Bear, LLP

(57) ABSTRACT

Embodiments of the present disclosure are related to multivesicular liposome formulations encapsulating zinc meloxicam complex microparticles. Methods of making the zinc meloxicam complex microparticles and administering the zinc meloxicam complex microparticles encapsulated in multivesicular liposome formulations and their use as medicaments are also provided.

34 Claims, 33 Drawing Sheets

(51) Int. Cl.
   *A61P 29/00* (2006.01)
   *A61K 9/00* (2006.01)
   *A61K 47/24* (2006.01)
   *A61K 31/5415* (2006.01)

(52) U.S. Cl.
   CPC ........ *A61K 31/5415* (2013.01); *A61K 31/555* (2013.01); *A61K 47/24* (2013.01); *A61P 29/00* (2018.01)

(56) References Cited

U.S. PATENT DOCUMENTS

| | | |
|---|---|---|
| 4,531,937 A | 7/1985 | Yates |
| 4,565,696 A | 1/1986 | Heath et al. |
| 4,612,370 A | 9/1986 | Hunt |
| 4,755,173 A | 7/1988 | Konopka et al. |
| 4,897,355 A | 1/1990 | Eppstein et al. |
| 4,933,192 A | 6/1990 | Darling et al. |
| 5,204,112 A | 4/1993 | Hope et al. |
| 5,230,899 A | 7/1993 | Park et al. |
| 5,576,017 A | 11/1996 | Kim |
| 5,723,147 A | 3/1998 | Kim et al. |
| 5,759,573 A | 6/1998 | Kim |
| 5,766,627 A | 6/1998 | Sankaram et al. |
| 5,962,016 A | 10/1999 | Willis |
| 5,993,850 A | 11/1999 | Sankaram et al. |
| 6,017,328 A | 1/2000 | Fischell et al. |
| 6,106,858 A | 8/2000 | Ye et al. |
| 6,132,766 A | 10/2000 | Sankaram et al. |
| 6,162,462 A | 12/2000 | Bolotin et al. |
| 6,258,791 B1 | 7/2001 | Braun et al. |
| 6,306,432 B1 | 10/2001 | Shirley et al. |
| 6,759,057 B1 | 7/2004 | Weiner et al. |
| 7,105,330 B2 | 9/2006 | Stern et al. |
| 8,071,127 B2 * | 12/2011 | Cipolla ............... A61K 9/0073 424/450 |
| 8,097,614 B2 | 1/2012 | Heit |
| 8,182,835 B2 | 5/2012 | Kim et al. |
| 2002/0009466 A1 | 1/2002 | Brayden |
| 2002/0035107 A1 | 3/2002 | Henke |
| 2002/0039596 A1 | 4/2002 | Hartounian et al. |
| 2002/0041895 A1 * | 4/2002 | Gregoriadis ........... A61K 9/127 424/450 |
| 2002/0169102 A1 | 11/2002 | Frey, II |
| 2003/0060559 A1 | 3/2003 | Oliviere et al. |
| 2003/0162234 A1 | 8/2003 | Jallad et al. |
| 2003/0235610 A1 | 12/2003 | McLean et al. |
| 2004/0071767 A1 | 4/2004 | Cevc et al. |
| 2004/0171740 A1 | 9/2004 | Ruberti et al. |
| 2004/0224010 A1 | 11/2004 | Hofland et al. |
| 2004/0268425 A1 | 12/2004 | Bookbinder et al. |
| 2005/0272697 A1 | 12/2005 | Herzberg et al. |
| 2006/0104968 A1 | 5/2006 | Bookbinder et al. |
| 2007/0009434 A1 | 1/2007 | Low et al. |
| 2007/0009583 A1 | 1/2007 | Qvist |
| 2007/0065541 A1 | 3/2007 | Keller et al. |
| 2007/0116777 A1 | 5/2007 | Schwarz et al. |
| 2007/0232566 A1 | 10/2007 | Wright et al. |
| 2007/0235889 A1 | 10/2007 | Hartounian et al. |
| 2008/0075807 A1 | 3/2008 | Baldwin et al. |
| 2008/0090861 A1 | 4/2008 | Barrett |
| 2009/0131543 A1 | 5/2009 | Weitz et al. |
| 2009/0232731 A1 | 9/2009 | Funk et al. |
| 2009/0269396 A1 | 10/2009 | Cipolla et al. |
| 2009/0291133 A1 | 11/2009 | Wang et al. |
| 2009/0311237 A1 | 12/2009 | Frost |
| 2010/0035937 A1 | 2/2010 | Gruber |
| 2010/0056403 A1 | 3/2010 | Abad |
| 2010/0119592 A1 | 5/2010 | Frankel |
| 2010/0305500 A1 * | 12/2010 | Lambert ............... A61K 9/0019 604/82 |
| 2011/0142917 A1 | 6/2011 | Alpert et al. |
| 2011/0237648 A1 | 9/2011 | Khvorova |
| 2011/0250264 A1 | 10/2011 | Schutt et al. |
| 2012/0027842 A1 | 2/2012 | Hutchinson et al. |
| 2012/0114740 A1 | 5/2012 | Garcia et al. |
| 2012/0128757 A1 | 5/2012 | Kikuchi et al. |
| 2012/0244206 A1 | 9/2012 | Cipolla et al. |
| 2013/0183374 A1 | 7/2013 | Garcia et al. |
| 2013/0189348 A1 | 7/2013 | Garcia et al. |
| 2013/0189350 A1 | 7/2013 | Garcia et al. |
| 2013/0209547 A1 | 8/2013 | Garcia et al. |
| 2013/0209548 A1 | 8/2013 | Garcia et al. |
| 2015/0174069 A1 | 6/2015 | Hong et al. |
| 2015/0231069 A1 | 8/2015 | Modi |
| 2015/0265867 A1 | 9/2015 | Sarangapani |
| 2016/0102086 A1 | 4/2016 | Dodd et al. |
| 2016/0220692 A1 | 8/2016 | Pienta et al. |

FOREIGN PATENT DOCUMENTS

| | | |
|---|---|---|
| WO | WO 87/07506 | 12/1987 |
| WO | WO 88/07853 | 10/1988 |
| WO | WO 92/09268 | 6/1992 |
| WO | WO 94/23697 | 10/1994 |
| WO | WO 96/08235 | 3/1996 |
| WO | WO 99/025319 | 5/1999 |
| WO | WO 03/020037 | 3/2003 |
| WO | WO 03/046145 | 6/2003 |
| WO | WO 04/000226 | 12/2003 |
| WO | WO 07/049278 | 5/2007 |
| WO | WO 08/030818 | 3/2008 |
| WO | WO 08/072952 | 6/2008 |
| WO | WO 08/063341 | 10/2008 |
| WO | WO 10/014895 | 2/2010 |
| WO | WO 10/113983 | 10/2010 |
| WO | 2012/058483 | * 5/2012 |

OTHER PUBLICATIONS

Duangjit et al., Mar. 2013, Evaluation of meloxicam-loaded cationic transfersomes as transdermal drug delivery carriers, AAPS PharmSciTech, 14(1):133-140.

Dyakova et al., 3d metal complexes with meloxicam as therapeutic agents in the fight against human glioblastoma multiforme and cervical carcinoma, Biotechnology & Biotechnological Equipment, 26(6):1190-1200.

International Search Report and Written Opinion dated Feb. 13, 2018 in PCT/US17/62375.

Bangham et al., 1965, Diffusion of Univalent Ions across the Lamellae of Swollen Phospholipids, J. Mol. Biol., 13:238-252.

Bannwarth et al., Piroxicam concentrations in plasma and synovial fluid after a single dose of piroxicam-β-cyclodextrin, International Journal of Clinical Pharmacology and Therapeutics, (2001) 39(1):33-36.

Bardou et al., 2010, Preventing the gastrointestinal adverse effects of nonsteroidal anti-inflammatory drugs: From risk factor identification to risk factor intervention, Joint Bone Spine, 77(1):6-12.

Barnard et al., 2006, Increase in Nonfatal Digestive Perforations and Haemorrhages Following Introduction of Selective NSAIDs, Drug Safety, 29(7):613-20.

Bjorkman, 1999, Current Status of Nonsteroidal Anti-Inflammatory Drug (NSAID) Use in the United States: Risk Factors and Frequency of Complications, Am. J. Med., 107(6A):3S-10S.

Cullis et al., 1987, Liposomes as Pharmaceuticals, (Ostro, Ed.), Marcel Dekker Inc., pp. 60-65.

Dorland's Illustrated Medical Dictionary, 2000, Definition of Instillation, W.B. Saunders Company, Philadelphia, PA, p. 904.

Foong et al., 1988, Retention and Distribution of Liposorne-entrapped [3H]Methotrexate Injected into Normal or Arthritic Rabbit Joints, J. Pharm. Pharmacol., 40:464-468.

Foong et al., 1993, Treatment of Antigen-induced Arthritis in Rabbits with Liposome-entrapped Methotrexate Injected Intra-articularly, J. Pharm. Pharmacol., 45:204-209.

Fowler, 1986, Plasma and Synovial Fluid Concentrations of Diclofenac Sodium and its Hydroxylated Metabolites During Once-Daily Administration of a 100 mg Slow-Release Formulation, Eur. J. Clin. Pharmacol., 31:469-472.

(56) References Cited

OTHER PUBLICATIONS

Fricker et al., Aug. 2010, Phospholipids and lipid-based formulations in oral drug delivery, Pharmaceutical Research, 27:1469-1486.
Hollenz et al., 2006, NSAID-Associated Dyspepsia and Ulcers: A prospective Cohort Study in Primary Care, Digestive Diseases, 24:189-194.
Huang, 1969, Studies on Phosphatidylcholine Vesicles. Formation and Physical Characteristics, Biochemistry, 8(1):334-352.
Hundal et al., 1993, Total and Free Plasma and Total Synovial Fluid Piroxicam Concentrations: Relationship to Antiinflammatory Effect in Patients with Reactive Arthritis and Other Arthritides, Scand. J. Rheumatol., 22(4):183-187.
Hwang et al., 1999, Remote loading of diclofenac, insulin and fluorescein isothiocyanate labeled insulin into liposomes by pH and acetate gradient methods, Int. J. Pharm., 179:85-95.
Jain et al., Aug. 2007, Multivesicular liposomes bearing celecoxib-beta-cyclodextrin complex for transdermal delivery, Drug Deliv., 14(6):327-335.
Kim et al., 1981, Preparation of Cell-Size Unilamellar Liposomes With High Captured Volume and Defined Siz, Biochimica et Biophysica Acta, 646(1):1-9.
Kim et al., 1983, Preparation of Multivesicular Liposomes, Biochimica et Biophysica Acta, 728:339-348.
Larsen et al., 2008, Intra-Articular Depot Formulation Principles: Role in the Management of Postoperative Pain and Arthritic Disorders, J. Pharm. Sci., 97(11):4622-4654.
Mantripragada, 2002, A lipid based depot (DepoFoam® technology) for sustained release drug delivery, Progress in Lipid Research 41:392-406.
Martin et al., 1993, Physical Pharmacy, Fourth Edition, Lippincott Williams & Wilkins, Baltimore, MD, p. 101.
Neander et al., 1992, Pharmacokinetics of intraarticuiar indomethacin in patients with osteoarthritis, Eur. J. Clin. Pharmacol., 42(3):301-305.
Patel et al., 2007, Chapter 25. Pain Management, in Desai et al. eds., Gibaldi's Drug Delivery Systems in Pharmaceutical Care, p. 469.
Peris et al., 2001, Iatrogenic Cost Factors Incorporating Mild and Moderate Adverse Events in the Economic Comparison of Aceclofenac and Other NSAIDs, Pharmacoeconomics, 19(7):779-790.
Shibuya et al., 2009, Colonic mucosal lesions associated with long-term or short-term administration of nonsteroidal anti-inflammatory drugs, Colorectal Diseases, 12:1113-1121.
Xu Shi Ying, 2006, Microencapsulation Technology: Principles and Applications, Beijing Chemical Industry Press ISBN 7-5025-8870-1.
Yamagata et al., 2007, Prevalence and incidence of NSAID-induced gastrointestinal ulcers and bleeding, Nippon Rinsho, 65(10):1749-1753.
Zhang, 2008, STEALTH Liposomes: the silent nanobombers, Trends in Bio/Pharm. Ind., 4:19-24.

\* cited by examiner

ZINC MELOXICAM COMPLEX MICROPARTICLE MULTIVESICULAR LIPOSOME FORMULATIONS AND PROCESSES FOR MAKING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

Orally administered nonsteroidal anti-inflammatory drugs (NSAIDs) are effective relievers of pain and inflammation in a variety of therapeutic settings. Oral NSAID treatment, however, has been linked to a variety of serious gastrointestinal complications, including peptic ulcer, digestive perforation, hemorrhage, colonic ulcer, and colitis (Hollenz et al., Dig Dis., 24(1-2):189-94 (2006); Yamagata et al., Nippon Rinsho, 65(10):1749-53 (2007); Shibuya et al., Colorectal Dis. (2009)). Gastro-intestinal (GI) symptoms can appear within the first two weeks of therapy. Therefore, patients with both acute and chronic conditions are affected (Peris et al., Pharmacoeconomics, 19(7):779-90 (2001)). GI toxicity, and the increased morbidity that results from it, account for the majority of the cost associated with NSAID therapy (Id). It threatens both the utility and economic viability of NSAID therapy for the treatment of pain and inflammation (Bjorkman, Am. J. Med., 107(6A):3S-10S (1999)). Gastro-protective co-therapy is being explored as a solution to the GI toxicity problem; however this approach is currently considered cost prohibitive. In general, GI toxicity is attributable to the magnitude and duration of drug exposure required to achieve efficacious drug levels at the site of action, for instance at the synovial site of action.

Postoperative pain is one of the most common forms of acute pain (Schug et al., PharmacoEconomics 1993; (4): 260-267; Carr et al., Lancet. 1999; 353: 2051-8). Inflammatory mediators, including prostanoids, are released as a result of surgical trauma. These mediators affect the development of pain by either changing the firing threshold or by direct stimulation of nociceptors (Kurukahvecioglu et al., West Indian Med J. 2007 December; 56(6):530-33). A multimodal approach to postoperative analgesia, using a combination of agents (e.g., opioids, local anesthetics, NSAIDs) and delivery techniques (patient-controlled analgesia, epidural and regional blocks), is currently recognized as a best practice in pain management (Breivik et al., Bailliére's Clin Anaesthesiol. 1995; 9:423-60; Breivik et al., Bailliére's Clin Anaesthesiol. 1995; 9:403-22; ASA Task Force, Anesthesiology. 1995; 82:1071-81; Dahl et al., Acta Anaesthesiol Scand. 2000; 44:1191-203).

Meloxicam (MLX) is an NSAID that exhibits anti-inflammatory, analgesic, and antipyretic activities. It has the following structure:

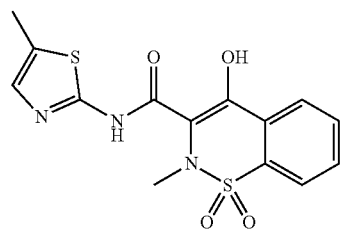 [SMILES: Cc1cnc(NC(=O)C2=C(O)c3ccccc3S(=O)(=O)N2C)s1]

It is believed that MLX exerts its anti-inflammatory effect by blocking cyclooxygenase (COX), the enzyme responsible for converting arachidonic acid to prostaglandin H2, a precursor of inflammation-producing prostaglandins. MLX is considered a potent and more selective inhibitor of cyclooxygenase-2 (COX-2), the enzyme responsible for mediating inflammation-related prostaglandin, than cyclooxygenase 1 (COX-1), which plays a role in protecting the stomach lining. MLX is approved for use in a variety of clinical conditions, including pain management in inflammatory conditions, such as osteoarthritis, rheumatoid arthritis, and juvenile rheumatoid arthritis. MLX is approved for once daily oral administration as 7.5 mg or 15 mg tablets, or in oral suspension of 7.5 mg/5 mL. This relatively high, side effect-inducing dose is generally necessary to achieve efficacious drug levels. For example, a side effect-inducing dose may be necessary to achieve efficacious drug levels in the synovial cavity. The levels of drug achieved in the synovial cavity following systemic MLX administration have been shown to be significantly lower than that of plasma (Bannwart et al., Int. J. Clin. Pharmacol. Therapy, 39(1):33-36 (2001); Hundal et al., Scand. J. Rheumatol., 22(4):183-187 (1993)). Generally, MLX can be administered to a number of cavities and tissues of the body.

The local residence time of a drug in the synovial cavity is closely related to drug efficacy (Foong et al., J. Pharm. Pharmacol., 40(7):464-468 (1988); Foong et al., J. Pharm. Pharmacol., 45(3):204-209 (1993)). However, drugs are typically cleared in a matter of hours from the synovial fluid (Neander et al., Eur. J. Clin. Pharmacol., 42(3):301-305 (1992); Larsen et al., J. Pharm. Sci., 97(11):4622-4654 (2008)). Unencapsulated NSAID drugs, therefore, whether they are administered intraarticularly or orally, have limited opportunity to achieve their therapeutic effect.

Meloxicam has limited solubility at physiological pH and its solubility is highly pH dependent. Earlier MVL formulation work revealed that a very high internal pH (~9.5) would be required to achieve the desired solubility and potency. In some cases, following neutralization in a reduced pH environment, MLX dissolved readily into the organic phase during the manufacture of the MVLs, and easily passed through DepoFoam (MVL) particle membranes. As a result, previous attempts to encapsulate MLX in MVLs had limited success or low encapsulation yields. Therefore, there remains a need to develop new meloxicam liposomal formulations with high encapsulation yields and sustained release properties.

SUMMARY

The present application relates to meloxicam divalent metal complexes encapsulated multivesicular liposome (MVL) formulations. In particular, embodiments of the invention relate to multivesicular liposome compositions comprising zinc meloxicam complex microparticles, and one or more pH adjusting agents in the first aqueous phase of the MVLs. Methods of making zinc meloxicam complex microparticles, MVL and non-MVL formulations containing zinc meloxicam complex microparticles, and their use as medicaments are also provided. Some implementations provide improved liposomal encapsulation of meloxicam, and may minimize the side effects of meloxicam while maintaining or improving efficacy. Further implementations provide extended release formulations of meloxicam. In addition, in some implementations the formulation can achieve efficacious drug levels at the site where inflammation is present without exposing the full body to a high concentration of meloxicam.

Embodiments of the present disclosure are directed to improved meloxicam multivesicular liposome formulations, in particular zinc meloxicam complex microparticle encapsulated multivesicular liposome formulations; formulations comprising zinc meloxicam complex microparticles; processes for making the same; and methods of treating pain and inflammation using the same.

Some embodiments disclosed herein are directed to formulations of MVLs, comprising zinc meloxicam complex microparticles, and one or more pH adjusting agents encapsulated in a first aqueous phase of the MVLs, and lipid components comprising at least one amphipathic lipid selected from phosphatidyl choline or salts thereof, phosphatidyl glycerol or salts thereof, or combinations thereof, or at least one neutral lipid, or combinations thereof. In some embodiments, the MVL particles are suspended in a suspending solution.

In some embodiments of the meloxicam MVL formulations described herein, the zinc meloxicam complex is formed by reacting meloxicam with a zinc salt, for example, zinc chloride. In some such embodiments, the zinc meloxicam complex includes a molar ratio of zinc to meloxicam about 1:4 to 4:1, about 1:3 to 3:1, about 1:2 to 2:1, or about 1:1. In one particular embodiment, the zinc to meloxicam ratio is 1:2 and the formula of such zinc meloxicam complex is $Zn(MLX)_2$. In some further embodiments, the zinc meloxicam complex may exist in its hydrate or solvate form. In one example, the zinc meloxicam complex is $Zn(MLX)_2 \cdot 4H_2O$. In some embodiments, the zinc meloxicam complex is partially or substantially insoluble in the first aqueous phase. In some embodiments, the zinc meloxicam complex is insoluble in the first aqueous phase. In some embodiments, the zinc meloxicam complex is in the form of microparticles having a median particle diameter of less than about 50 µm. In some further embodiments, the median particle diameter of the zinc meloxicam complex is less than about 5 µm, about 2 µm, about 1 µm, less than about 1 µm, about 0.5 µm, or less than about 0.2 µm. In some further embodiments, the median particle diameter is about 50 µm, about 45 µm, about 40 µm, about 35 µm, about 30 µm, about 25 µm, about 20 µm, about 15 µm, about 10 µm, about 5 µm, about 3 µm, about 2 µm, about 1 µm, about 0.5 µm, or about 0.2 µm, or is within a range defined by any two of the preceding values.

In some embodiments of the meloxicam MVL formulations described herein, the pH adjusting agents comprise one or more organic acids, one or more organic bases, or combinations thereof. In some embodiments, the one or more organic acids include tartaric acid. In some embodiments, the one or more organic bases include lysine or histidine or combinations thereof. In some embodiments, the pH of the first aqueous phase of the multivesicular liposomes is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0, or within a range defined by any two of the preceding pH values. In some embodiments, the pH of the first aqueous phase of the multivesicular liposomes is from about 5.6 to about 6.6. In one embodiment, the pH of the first aqueous phase of the multivesicular liposomes is about 5.8.

In some embodiments of the zinc meloxicam complex microparticle MVL formulations described herein, the first aqueous phase of the multivesicular liposomes further comprises one or more tonicity agents. In some embodiments, the one or more tonicity agents include an amino acid, a sugar, or combinations thereof. In some embodiments, the one or more tonicity agents include sorbitol, sucrose, lysine, or combinations thereof. In some embodiments, the osmolality of the first aqueous phase of the MVLs is about 150, 200, 230, 240, 250, 260, 270, 280, 290, 300, 310, 320, 330, 340, 350, 360, or 370 mOsm/kg, or within a range defined by any two of the preceding values. In some embodiments, the osmolality of the first aqueous phase of the MVLs is from about 250 mOsm/kg to about 350 mOsm/kg. In some further embodiments, the osmolality of the first aqueous phase of the MVLs is from about 280 mOsm/kg to about 320 mOsm/kg. In one embodiment, the osmolality of the first aqueous phase of the MVLs is about 290 mOsm/kg to about 300 mOsm/kg. In further embodiments, the first aqueous suspension may have an osmolality of about 370 to about 1000 mOsm/kg, for example, about 650 to about 800 mOsm/kg.

In some embodiments of the zinc meloxicam complex microparticle MVL formulations described herein, the lipid components of the multivesicular liposomes include at least one triglyceride. In some further embodiments, the lipid components include phosphatidyl choline or salts thereof, and at least one triglyceride. In some further embodiments of the meloxicam MVL formulations described herein, the lipid components of the multivesicular liposomes include phosphatidyl choline or salts thereof, phosphatidyl glycerol or salts thereof, and at least one triglyceride. In some embodiments, the phosphatidyl choline is dierucoyl phosphatidyl choline (DEPC). In some embodiments, the phosphatidyl glycerol is dipalmitoyl phosphatidyl glycerol (DPPG). In some embodiments, the triglyceride is tricaprylin. In some embodiments, the lipid components further comprise cholesterol.

In some embodiments of the zinc meloxicam complex microparticle MVL formulations described herein, the MVL particles are suspended in a suspending or buffer solution. For example, the second aqueous phase may be removed from a formulation of MVLs, and the MVLs may be placed in a suspending solution. The suspending solution may define the external pH of the MVL formulation. In some embodiments, the pH of the suspending solution is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, or 10.5, or within a range defined by any two of the preceding pH values. In some embodiments, the pH of the suspending solution is from about 6.0 to 8.0, or from about 5 to 8. In one embodiment, the pH of the suspending solution is about 6.1.

In some embodiments of the zinc meloxicam complex microparticle MVL formulations described herein, the meloxicam encapsulated multivesicular liposomes have a median particle diameter of about 5, 10, 15, 20, 25, 30, 35, 40, 45, 50, 55, 60, 65, 70, 75, 80, 85, 90, 95, or 100 µm, or within a range defined by any two of the preceding values.

In some further embodiments, the multivesicular liposomes have a median particle diameter ranging from about 10 µm to about 50 µm. In some further embodiments, the multivesicular liposomes have a median particle diameter ranging from about 25 µm to about 40 µm. In still some further embodiments, the multivesicular liposomes have a median particle diameter ranging from about 15 µm to about 30 µm. In further embodiments, the zinc meloxicam is a microcrystalline solid in a crystalline form exhibiting 2θ peaks in an XRPD spectrum comprising about 6.3, about 10.3, about 12.5, about 13.7, about 16.9, about 23.1, about 23.3, about 25.3, about 26.3, about 31.3, about 39.9, and about 42.4 degrees.

In some embodiments of the zinc meloxicam complex microparticle MVL formulations described herein, the concentration or potency of meloxicam in the final multivesicular liposome formulation is about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 16, 17, 18, 19, 20, or 25 mg/mL, or within a ranged defined by any two of the preceding values. In some such embodiments, the concentration of meloxicam in the multivesicular liposome formulation is from about 1.0 mg/mL to about 10.0 mg/mL. In some further embodiments, the concentration of the meloxicam in the multivesicular liposome formulation is from about 2.0 mg/mL to about 5.0 mg/mL. In some further embodiments, the concentration of the meloxicam in the multivesicular liposome formulation is from about 3.0 mg/mL to about 7.0 mg/mL. In some further embodiments, the concentration of the meloxicam in the multivesicular liposome formulation is from about 2.0 mg/mL to about 3.5 mg/mL. In still some further embodiments, the concentration of the meloxicam in the multivesicular liposome formulation is from about 2.4 mg/mL to about 3.3 mg/mL. In one embodiment, the concentration of the meloxicam in the multivesicular liposome formulation is about 3.0 mg/mL. In another embodiment, the concentration of meloxicam in the multivesicular liposome formulation is about 2.4 mg/mL. In some embodiments, the MVL formulation may further comprise unencapsulated meloxicam.

In some embodiments of the zinc meloxicam complex microparticle formulations described herein, for example, zinc meloxicam complex microparticle MVL formulations described herein, the formulation is pharmaceutically acceptable for administration by injection, such as subcutaneous injection, intraarticular injection, intramuscular, intraperitoneal, intraocular, intrathecal, or any other parenteral administration means such as those known in the pharmaceutical art. The composition or formulation can further be administered by infusion, instillation, or infiltration as known in the pharmaceutical art. In one embodiment, the formulation is suitable for administration by local injection into a surgical site. In another embodiment, the formation is suitable for administration by direct instilling into an open wound or a body cavity. In one further embodiment, the formulation is suitable for wound instillation. The composition or formulation can further be administered topically.

In all embodiments of the zinc meloxicam complex microparticle MVL formulations described herein, the formulation is cyclodextrin free.

Some embodiments of the present application are directed to methods of treating pain or inflammation, comprising administering a zinc meloxicam complex microparticle formulation as described herein, in particular, a zinc meloxicam complex microparticle encapsulated MVL formulation to a subject in need thereof. In some embodiments, the subject is suffering from postoperative pain from a surgical site. In some other embodiments, the subject is suffering from arthritis. In some other embodiments, the subject is suffering from pain from an injury. In some embodiments, the administration is by injection. In further embodiments, the administration is by parenteral injection. In some such embodiments, the injection is intramuscular, intraperitoneal or subcutaneous injection. In some other embodiments, the injection is intra-articular injection. In some embodiments, the injection is not intra-vascular injection. In some alternative embodiments, the administration of the zinc meloxicam complex microparticle MVLs is by infiltration, for example, postsurgical infiltration. In still some alternative embodiments, the administration of the zinc meloxicam complex microparticle MVLs is by wound instillation, or simply instilling a composition or formulation containing zinc meloxicam complex microparticle MVLs into a wound, body cavities, or a fluid filled compartment inside the body. In still some alternative embodiments, the administration of the zinc meloxicam complex microparticle MVLs is topical to the skin.

Some embodiments of the present application are directed to use of a zinc meloxicam complex microparticle encapsulated MVL formulation in the preparation of a medicament for the treatment of pain or inflammation. In some embodiments, the pain or inflammation to be treated is postoperative pain or inflammation from a surgical site. In some other embodiments, the pain or inflammation to be treated is from an injury. In some other embodiments, the pain or inflammation is caused by arthritis. In some embodiments, the medicament containing zinc meloxicam complex microparticle MVLs is formulated for administration by injection. In further embodiments, the injection is parenteral. In some such embodiments, the injection is intraperitoneal, intramuscular or subcutaneous injection. In some other embodiments, the injection is intra-articular injection. In some embodiments, the injection is not intra-vascular injection. In some alternative embodiments, the medicament containing zinc meloxicam complex microparticle MVLs is formulated for administration by infiltration, for example, postsurgical infiltration. In still some alternative embodiments, the medicament containing zinc meloxicam complex microparticle MVLs is formulated for administration by wound instillation, or simply a formulation or suspension for instilling into a wound, a body cavity, or a fluid filled compartment inside the body. In still some alternative embodiments, the administration of the medicament containing zinc meloxicam complex microparticle MVLs is topical.

Some embodiments of the present application are directed to processes for preparing a zinc meloxicam complex microparticle encapsulated MVL formulation as described herein. The process includes preparing a first aqueous suspension by steps comprising mixing meloxicam, a zinc salt, and one or more pH adjusting agents; preparing a first emulsion by mixing the first aqueous suspension with a volatile water-immiscible organic solvent phase; combining said first emulsion and a second aqueous phase to provide a second emulsion; and substantially removing the volatile water-immiscible organic solvent from the second emulsion. In some embodiments, the volatile water-immiscible organic solvent is substantially removed by dispersing the second emulsion into a circulating gas atmosphere or phase, for example, by using an atomizing nozzle. In further embodiments, the volatile water-immiscible organic solvent is removed by sparging the second emulsion with an inert gas.

In some embodiments of the processes for preparing zinc meloxicam complex microparticle MVL formulations, the zinc salt is zinc chloride. In some embodiments, the zinc meloxicam complex has a formula of $Zn(MLX)_2$. In some further embodiments, the zinc meloxicam complex has a formula of $Zn(MLX)_2(OH_2)_2$. In some further embodiments, the zinc meloxicam complex is in the form of microparticles having a median particle diameter of about 50 µm, about 45 µm, about 40 µm, about 35 µm, about 30 µm, about 25 µm, about 20 µm, about 15 µm, about 10 µm, about 5 µm, about 3 µm, about 2 µm, about 1 µm, about 0.5 µm, or about 0.2 µm. In some further embodiments, the zinc meloxicam complex is in the form of microparticles having a median particle diameter of less than about 5 µm, less than about 2 µm, less than about 1 µm, less than about 0.5 µm, or less than about 0.2 µm. In some embodiments, the zinc meloxicam complex microparticles are microcrystalline. In some embodiments, there are no detectable levels of zinc meloxicam complex microparticles are not microcrystalline. In some embodiments, the zinc meloxicam complex microparticles are at least partially microcrystalline. In further embodiments, the microcrystalline zinc meloxicam complex is present as $Zn(MLX)_2 \cdot 4(H_2O)$.

In some embodiments of the processes for preparing zinc meloxicam complex microparticle MVL formulations as described herein, the pH adjusting agents that are used for the preparation of the first aqueous suspension comprise one or more organic acids, one or more organic bases, or combinations thereof. In some embodiments, the one or more organic acids include tartaric acid. In some embodiments, the one or more organic bases include lysine or histidine or combinations thereof. In some embodiments, the pH of the first aqueous suspension is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0, or within a range defined by any two of the preceding pH values. In some embodiments, the pH of the first aqueous suspension is from about 5.6 to about 6.6. In one embodiment, the pH of the first aqueous phase of the multivesicular liposomes is about 5.8.

In some embodiments of the processes for preparing zinc meloxicam complex microparticle MVL formulations as described herein, the second aqueous phase comprises one or more organic or inorganic acids, one or more organic or inorganic bases, or combinations thereof. In some such embodiments, the one or more organic acids comprise tartaric acid. In some such embodiments, the one or more organic bases comprise histidine and/or lysine. In some embodiments, the pH of the second aqueous phase is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, or 10.5, or within a range defined by any two of the preceding pH values. In some embodiments, the pH of the second aqueous phase is from about 4.8 to about 7.2. In some further embodiments, the pH of the second aqueous phase is from about 5.5 to about 7.0. In one embodiment, the pH of the second aqueous phase is about 6.1. The second aqueous phase can contain additional components such as tonicity agents, pH adjusting agents, metal sequestering agents, or combinations thereof.

In some embodiments, the MVLs are further subject to an exchange of the second aqueous phase. The exchange may be, for example, through cross-flow filtration, or through batch exchange. The second aqueous phase may be partially or completely replaced by a suspending solution. The suspending solution may comprise a buffer. In some embodiments, the external pH of the final MVL formulations is from about 6.0 to about 8.0.

In any embodiment of the processes for preparing zinc meloxicam complex microparticle MVL formulations as described herein, each step of the processes may be performed under a sterile or aseptic condition. In some further embodiments, some or all steps of the processes may be performed in a continuous fashion.

Some embodiments described herein are directed to zinc meloxicam complex microparticle encapsulated multivesicular liposomes formulations prepared by the processes described herein.

Some embodiments described herein are directed to zinc meloxicam complex microparticles. In some embodiments, the zinc meloxicam complex microparticles have a median particle diameter of about 5 µm or less, about 2 µm or less, 1 µm or less, about 0.5 µm or less, or about 0.2 µm or less. In some further embodiments, the zinc meloxicam complex microparticles have a median particle diameter of about 50 µm, about 45 µm, about 40 µm, about 35 µm, about 30 µm, about 25 µm, about 20 µm, about 15 µm, about 10 µm, about 5 µm, about 3 µm, about 2 µm, about 1 µm, about 0.5 µm, or about 0.2 µm. In one embodiment, the zinc meloxicam complex has the formula $Zn(MLX)_2$.

Some embodiments described herein are directed to non-MVL formulations. In particular, some embodiments are directed to pharmaceutical formulations comprising zinc meloxicam complex microparticles, and a pharmaceutically acceptable carrier. In some embodiments, the zinc meloxicam complex microparticles are unencapsulated. In further embodiments, the formulation does not include liposomal particles. In some other embodiments, the formulation further comprises one or more lipids or surfactants. The lipids and/or surfactants may be at least partially in the form of unilamellar or multilamellar vesicles. In some such embodiments, at least a portion of the zinc meloxicam complex microparticles is encapsulated in the lipids or surfactants, for example, the unilamellar or multilamellar vesicles. In some such embodiments, at least a portion of the zinc meloxicam complex microparticles is encapsulated in the lipids or surfactants in the form of multivesicular liposomes. In one embodiment, the zinc meloxicam complex has the formula $Zn(MLX)_2$.

Some embodiments described herein are directed to methods of treating pain or inflammation comprising administering a zinc meloxicam complex microparticle formulation described herein. For example, some embodiments are directed to methods of treating pain or inflammation comprising administering zinc meloxicam complex microparticles and a pharmaceutically acceptable carrier. In some embodiments, the formulations are administered by injection. The injection may be parenteral. The injection may be, for example, intraocular, intrathecal, intraarticular, intramuscular, subcutaneous, intravenous or intraperitoneal injection. In some other embodiments, the formulations are administered by wound infusion, infiltration or instillation, or injection into a body cavity or a fluid-filled compartment. In some other embodiments, the formulations are administered topically to the skin.

Some embodiments described herein are directed to processes of making a zinc meloxicam complex microparticle as described herein, comprising mixing a first solution comprising a zinc salt and a second solution comprising meloxicam, wherein the pH of the first solution is from about 4.5 to about 6.0, and wherein the pH of the second solution is from about 7.5 to about 10.0. In some embodiments, the zinc salt is zinc chloride. In some embodiments, the pH of the first solution is from about 5.0 to about 5.5. In one embodiment, the pH of the first solution is about 5.3. In another embodiment, the pH of the first solution is about 5.5. In some embodiments, the pH of the second solution is from about 8.0 to about 9.0. In one embodiment, the pH of the second solution is about 8.2. In another embodiment, the pH of the second solution is about 8.5. In some embodiments, the pH of the mixture of the first solution and the second solution is about 6.6. In some embodiments, zinc meloxicam complex microparticles have a median particle diameter of about 50 µm or less, for example, about 5 µm or less, about 2 µm or less, 1 µm or less, about 0.5 µm or less, or about 0.2 µm or less or within a range defined by any two of the preceding values. In some embodiments, the zinc meloxicam complex microparticles are microcrystalline. In one embodiment, the zinc meloxicam complex has the formula $Zn(MLX)_2$. In another embodiment, the zinc meloxicam complex microparticles are at least partially microcrystalline.

Some further embodiments of the present application are directed to methods of treating pain or inflammation, comprising administering a zinc meloxicam complex microparticle formulation as described herein to a subject in need thereof. In some embodiments, the subject is undergoing or has undergone a surgical procedure. In some embodiments, the subject is suffering from postoperative pain from a surgical site. In some other embodiments, the subject is suffering from arthritis. In some other embodiments, the subject is suffering from pain from an injury. In some embodiments, the administration is by injection. In some such embodiments, the injection is intraocular, intrathecal, intravenous, intramuscular, subcutaneous, or intraperitoneal injection. In some other embodiments, the injection is intra-articular injection. In some embodiments, the injection of zinc meloxicam complex microparticle MVLs is not intravascular injection. In some alternative embodiments, the administration of the zinc meloxicam complex microparticle MVLs is by infiltration, for example, perisurgical or postsurgical infiltration. In still some alternative embodiments, the administration of the zinc meloxicam complex microparticle MVLs is by wound instillation, or simply instilling a formulation containing zinc meloxicam complex microparticle MVLs into a wound, body cavities, or a fluid filled compartment inside the body. In some further embodiments, the administration may be topical to the skin.

In any embodiments of the processes for preparing the zinc meloxicam complex microparticles as described herein, the processes may be performed under a sterile or aseptic condition. In some further embodiments, the processes may be performed in a continuous fashion.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments, and are not intended to be limiting in scope.

FIG. 11B is a sample in which the objective lens was not an oil-immersion lens.

FIG. 12A is a brightfield image with fluorescence overlayed to highlight zinc meloxicam microparticles, while the image of FIG. 12B includes phase contrast.

FIG. 20 also provides data for dissolved, uncomplexed meloxicam (diamonds—♦) and mass balance of dissolved and undissolved meloxicam (triangles—▲).

In FIG. 21A, the buffer is NaHPO$_4$, in FIG. 21B the buffer is 50 mM HisTA, while in FIG. 21C the buffer is 100 mM HisTA.

DETAILED DESCRIPTION

Figure 1A:
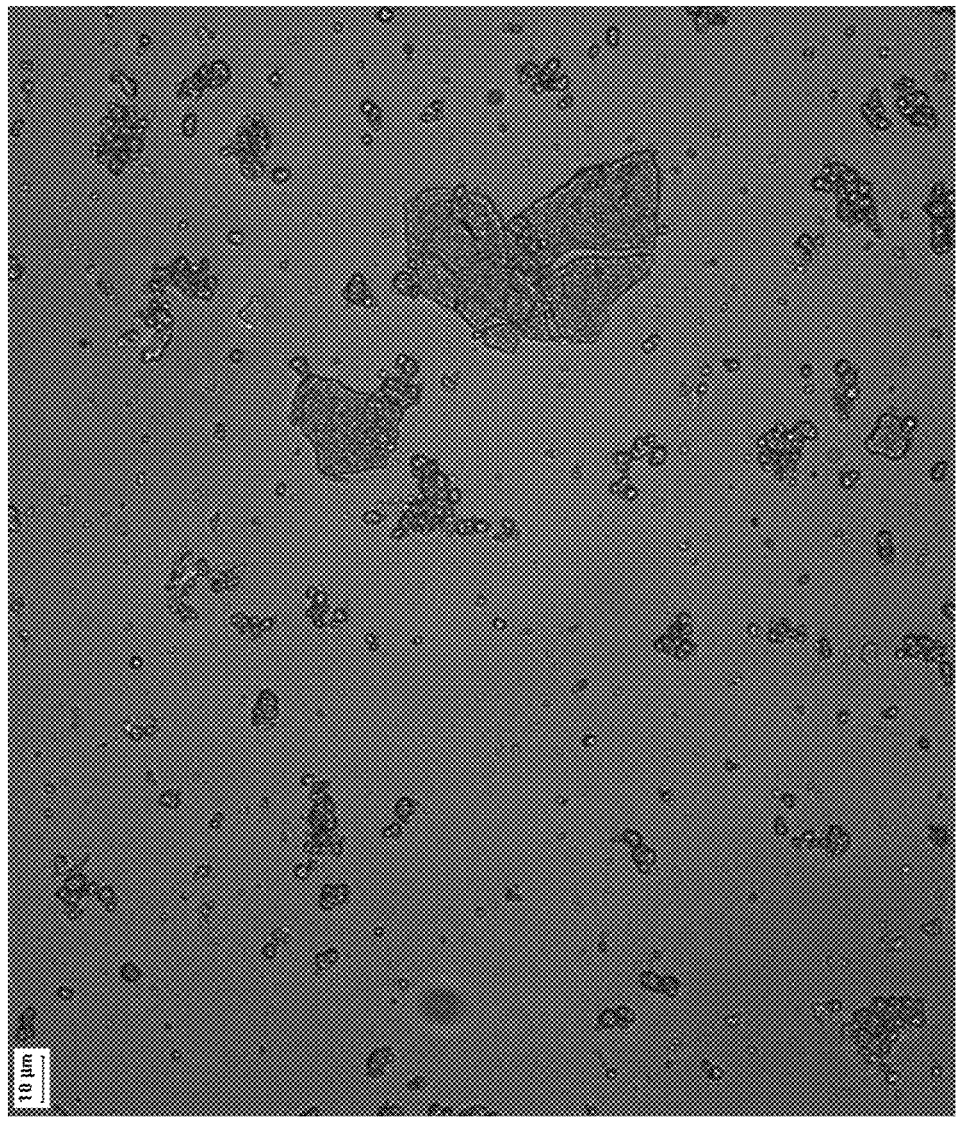
FIG. 1A and FIG. 1B depict an optical micrograph characterizing a microcrystalline form of zinc meloxicam complex $Zn(MLX)_2$ microparticles at two different scales.

The present embodiments provide formulations comprising multivesicular liposomes (MVL) encapsulating zinc meloxicam (MLX) complex microparticles. Some implementations minimize the side effects of MLX while maintaining or improving efficacy and lengthening the duration of the effect. The methods of using such formulations for treating, ameliorating, or preventing pain and inflammation, such as for use in managing inflammatory pain for arthritis and peri- and postsurgical pain are also disclosed. Also provided are methods of preparing formulations of multivesicular liposomes encapsulating meloxicam complex, in particular, zinc meloxicam complex microparticles.

Additional embodiments of the present disclosure relate to zinc meloxicam complex microparticles, the processes of preparing the same and non-MVL formulations comprising the zinc meloxicam complex microparticles and methods of treating using such formulations.

The physicochemical properties of MLX present challenges for traditional encapsulation of MLX into MVL formulations by known methods. MLX is a hydrophobic molecule and is poorly soluble in water at physiological pH ranges. Although solubility increases significantly at a pH above 8, due to the ionization of the molecule, solutions having a pH value greater than 8 to 8.5 and above are incompatible with MVL formulation development due to increased rate of lipid hydrolysis. Thus, using traditional methods of encapsulation results in a highly inefficient encapsulation of meloxicam into multivesicular liposomes.

It was unexpectedly found that the formation of a zinc MLX complex unexpectedly increases the efficiency of meloxicam incorporation into MVL formulations. Accordingly, provided herein are improved methods for encapsulation of meloxicam into multivesicular liposomes in a highly efficient manner. Furthermore, the methods described herein may be scaled up for large scale continuous production of MVL formulations encapsulating zinc meloxicam complex, in particular zinc meloxicam complex microparticles. Zinc is an essential mineral of exceptional biological and public health importance. It is biocompatible and promotes wound healing. See, for example, Sallit, J., "Rationale for Zinc Supplementation in Older Adult with Wounds," *Annals of Long-Term Care: Clinical Care and Aging.* 2012; 20(1):39-41. Therefore, a zinc meloxicam complex for use in the treatment of pain and inflammation provides additional benefits.

Accordingly, MVL formulations encapsulating zinc meloxicam complex microparticles as provided herein address all of the above-mentioned shortcomings of current meloxicam therapy by providing an high encapsulation yield of meloxicam into multivesicular liposomes with desired release profiles. Furthermore, local administration may include, for example, intraarticular administration, local infiltration, instillation, or infusion, topical, ocular, intraocular, nasal, and otic delivery. Local administration, for example, intraarticular administration, of zinc meloxicam complex microparticle MVL formulations allow for delivery of meloxicam directly to the site of action. Thus, local administration may reduce the plasma drug concentration and concentration-dependent side effects, and prolong the drug exposure of the affected joint from hours to days or weeks, to achieve increased therapeutic benefit. The instant embodiments are useful for acute treatment due to injury, flare-up, or surgery (peri- or post-surgical), as well as for chronic conditions such as rheumatoid arthritis or osteoarthritis. The instant controlled-release zinc meloxicam complex microparticle MVL formulations provide pain relief and reduce inflammation, while circumventing the side effects associated with current oral therapy. Using multivesicular liposome sustained-release technology, zinc meloxicam complex microparticle MVL formulations can be administered directly to the affected joint. The instant zinc meloxicam complex microparticle MVL formulations can also be administered by other routes of administration to treat local inflammation or pain. Local administration may reduce the dose requirement significantly, thereby reducing the potential for gastric and systemic toxicities associated with oral meloxicam administration. The instant zinc meloxicam complex microparticle MVL formulations release drug for up to two weeks, or under certain circumstances for up to ten weeks, and therefore, patients require infrequent dosing.

Subcutaneous, intramuscular or intraarticular administration of the instant zinc meloxicam complex microparticle MVL formulations also allow for systemic treatment of pain as an alternative to oral therapy. The advantage of this approach is that the MVL formulation can provide a controlled release pharmacokinetic profile as compared with oral immediate release dosage forms. Thus, subcutaneous, intraarticular or intramuscular administration provides longer duration and decreased plasma concentration-related side effects.

Alternatively, the zinc meloxicam complex microparticles may be formulated in other formulations that do not employ MVLs. For example, the zinc meloxicam complex microparticles can be formulated as other controlled release formulations such as unilamellar or multilamellar vesicle or liposome formulations. For further example, the zinc meloxicam complex microparticles can be coated with a phospholipid and/or a synthetic surfactant. These non-MVL formulations often do not possess all the advantages of the multivesicular liposome formulations.

Definitions

As used herein, the term "encapsulated" means that meloxicam is inside a liposomal particle, for example, the MVL particles, the unilamellar vesicles (ULVs) or multilamellar vesicles (MLVs). In some instances, meloxicam may also be on an inner surface, or intercalated in a membrane, of the MVLs.

As used herein, the term "median particle diameter" refers to volume weighted median diameter.

As used herein, the term "unencapsulated meloxicam" or "free meloxicam" refers to meloxicam outside the internal aqueous chambers of liposomal particles, for example the MVL, UVL or MLV particles. For example, unencapsulated meloxicam may reside in the suspending solution of these particles, or may be associated with the outer lipid membranes. Meloxicam which is associated with outer lipid membranes may adhere to a membrane surface. Unencapsulated or free meloxicam may exist either in the form of metal meloxicam complex (e.g., zinc meloxicam complex microparticles), or in an uncomplexed form. Unencapsulated zinc meloxicam complex microparticles may be associated with or stabilized by phospholipids and/or surfactants.

As used herein, "MLX-MVL" formulation refers to a multivesicular liposome formulation encapsulating meloxicam in the first aqueous phase of the MVL particles. "Zn-MLX-MVL" and "zinc meloxicam complex microparticle MVL" refers to a multivesicular liposome formulation encapsulating zinc meloxicam complex microparticles in the first aqueous phase of the MVL particles. In some embodiments, such formulation contains less than about 60%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.2% or 0.1% free meloxicam, or a range defined by any of the two preceding values.

As used herein, "DepoMLX" refers to zinc-meloxicam complex microparticles encapsulated in multivesicular liposomes. The DepoMLX may be characterized by a packed particle volume (PPV) measured in %. In some embodiments, such DepoMLX formulations contain from about 10% to about 80% (v/v), from about 10% to about 60% (v/v), or from about 20% to about 55% (v/v), or from about 30% to about 50% (v/v), or from about 40% to about 60% (v/v), multivesicular liposome particles. In one particular embodiment, DepoMLX formulations contain about 50% (v/v) multivesicular liposome particles. In a further embodiment, DepoMLX formulations contain about 40% (v/v) multivesicular liposome particles.

As used herein, "zinc meloxicam complex" and "Zn $(MLX)_2$," refer to zinc meloxicam complexes that may be partially or completely solvated, for example, partially or completely hydrated. "$Zn(MLX)_2$" and "zinc meloxicam complex microparticles" are intended to include all crystalline and amorphous forms thereof unless a particular form is specified. For example, in some embodiments, the $Zn(MLX)_2$ and the zinc meloxicam complex microparticles comprise amorphous zinc meloxicam. In other embodiments, the $Zn(MLX)_2$ and the zinc meloxicam complex microparticles comprise crystalline zinc meloxicam. In some embodiments, the $Zn(MLX)_2$ and the zinc meloxicam complex microparticles are partially or substantially crystalline.

In all instances, where the concentration of meloxicam in a zinc meloxicam complex and/or zinc meloxicam complex microparticles and/or in MVLs is provided (for example, in mg/mL) the mass refers to that of meloxicam alone.

As used herein, a "pH adjusting agent" refers to a compound that is capable of modulating the pH of an aqueous phase.

As used herein, the terms "tonicity" and "osmolality" are measures of the osmotic pressure of two solutions, for example, a test sample and water separated by a semi-permeable membrane. Osmotic pressure is the pressure that must be applied to a solution to prevent the inward flow of water across a semi-permeable membrane. Osmotic pressure and tonicity are influenced only by solutes that cannot readily cross the membrane, as only these exert an osmotic pressure. Solutes able to freely cross the membrane do not affect tonicity because they will become equal concentrations on both sides of the membrane. An osmotic pressure provided herein is as measured on a standard laboratory vapor pressure or freezing point osmometer.

As used herein, the term "sugar" as used herein denotes a monosaccharide or an oligosaccharide. A monosaccharide is a monomeric carbohydrate which is not hydrolysable by acids, including simple sugars and their derivatives, e.g. aminosugars. Examples of monosaccharides include sorbitol, glucose, fructose, galactose, mannose, sorbose, ribose, deoxyribose, neuraminic acid. An oligosaccharide is a carbohydrate consisting of more than one monomeric saccharide unit connected via glycosidic bond(s) either branched or in a chain. The monomeric saccharide units within an oligosaccharide can be the same or different. Depending on the number of monomeric saccharide units the oligosaccharide is a di-, tri-, tetra-, penta- and so forth saccharide. In contrast to polysaccharides the monosaccharides and oligosaccharides are water soluble. Examples of oligosaccharides include sucrose, trehalose, lactose, maltose and raffinose.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described. In addition, the materials, methods, and examples are illustrative only and not intended to be limiting.

Zinc Meloxicam Complex Microparticle Multivesicular Liposome Formulations

The instant embodiments are directed to MVLs encapsulating MLX, in particular embodiments, the zinc complex of MLX. MVLs, reported in Kim et al. (Biochim. Biophys. Acta, 728:339-348, 1983), are a group of unique forms of synthetic membrane vesicles that are different from other lipid-based delivery systems such as unilamellar liposomes (Huang, Biochemistry, 8:334-352, 1969; Kim, et al., Biochim. Biophys. Acta, 646:1-10, 1981) and multilamellar liposomes (Bangham, et al., J Mol. Bio., 13:238-252, 1965). The main structural difference between multivesicular liposomes and unilamellar liposomes (also known as unilamellar vesicles, "ULVs"), is that multivesicular liposomes contain multiple aqueous chambers per particle. The main structural difference between multivesicular liposomes and multilamellar liposomes (also known as multilamellar vesicles, "MLVs"), is that in multivesicular liposomes the multiple aqueous chambers are non-concentric. Multivesicular liposomes generally have between 100 to 1 million chambers per particle and all the internal chambers are interconnected by shared lipid-bilayer walls that separate the chambers. The structural differences between unilamellar, multilamellar, and multivesicular liposomes are illustrated in Sankaram et al., U.S. Pat. Nos. 5,766,627 and 6,132,766.

The structural and functional characteristics of multivesicular liposomes are not directly predictable from current knowledge of unilamellar vesicles and multilamellar vesicles. Multivesicular liposomes have a very distinctive internal morphology, which may arise as a result of the special method employed in the manufacture. Topologically, multivesicular liposomes are defined as having multiple non-concentric chambers within each particle, resembling a "foam-like" or "honeycomb-like" matrix; whereas multilamellar vesicles contain multiple concentric chambers within each liposome particle, resembling the "layers of an onion."

The presence of internal membranes distributed as a network throughout multivesicular liposomes may serve to confer increased mechanical strength to the vesicle. The particles themselves can occupy a very large proportion of the total formulation volume. The packed particle volume (PPV) of MVLs which is measured in a manner analogous to a hematocrit, representing the volume of the formulation that the particles make up and can approach as high as 80%. Typically the PPV is about 50%. At 50% PPV, the multivesicular liposome formulation typically consists of less than 5% w/w lipid. Thus, the encapsulated volume is approximately 50% while having a relatively low lipid concentration. The multivesicular nature of multivesicular liposomes also indicates that, unlike for unilamellar vesicles, a single breach in the external membrane of multivesicular vesicles will not result in total release of the internal aqueous contents.

Thus, multivesicular liposomes formulations consist of microscopic, spherical particles composed of numerous non-concentric aqueous chambers. The individual chambers are separated by lipid bilayer membranes composed of synthetic versions of naturally occurring lipids, resulting in a delivery vehicle that is both biocompatible and biodegradable. Thus, the zinc meloxicam complex microparticle MVL formulations consist of microscopic, spherical particles composed of numerous nonconcentric aqueous chambers encapsulating meloxicam in the form of a divalent metal meloxicam complex, for example, zinc meloxicam, for controlled release drug delivery. Such formulation is intended to prolong the local delivery of meloxicam, thereby enhancing the duration of action of the reduction of inflammation and pain. The instant zinc meloxicam complex microparticle MVL formulations comprising meloxicam provide either local site or systemic sustained delivery, and can be administered by a number of routes including subcutaneous, intra-articular into joints, intramuscular into muscle tissue, intraperitoneal, wound infusion, instillation or infiltration, or application to an open wound, or body cavities such as the nasal cavity.

Figure 11A:
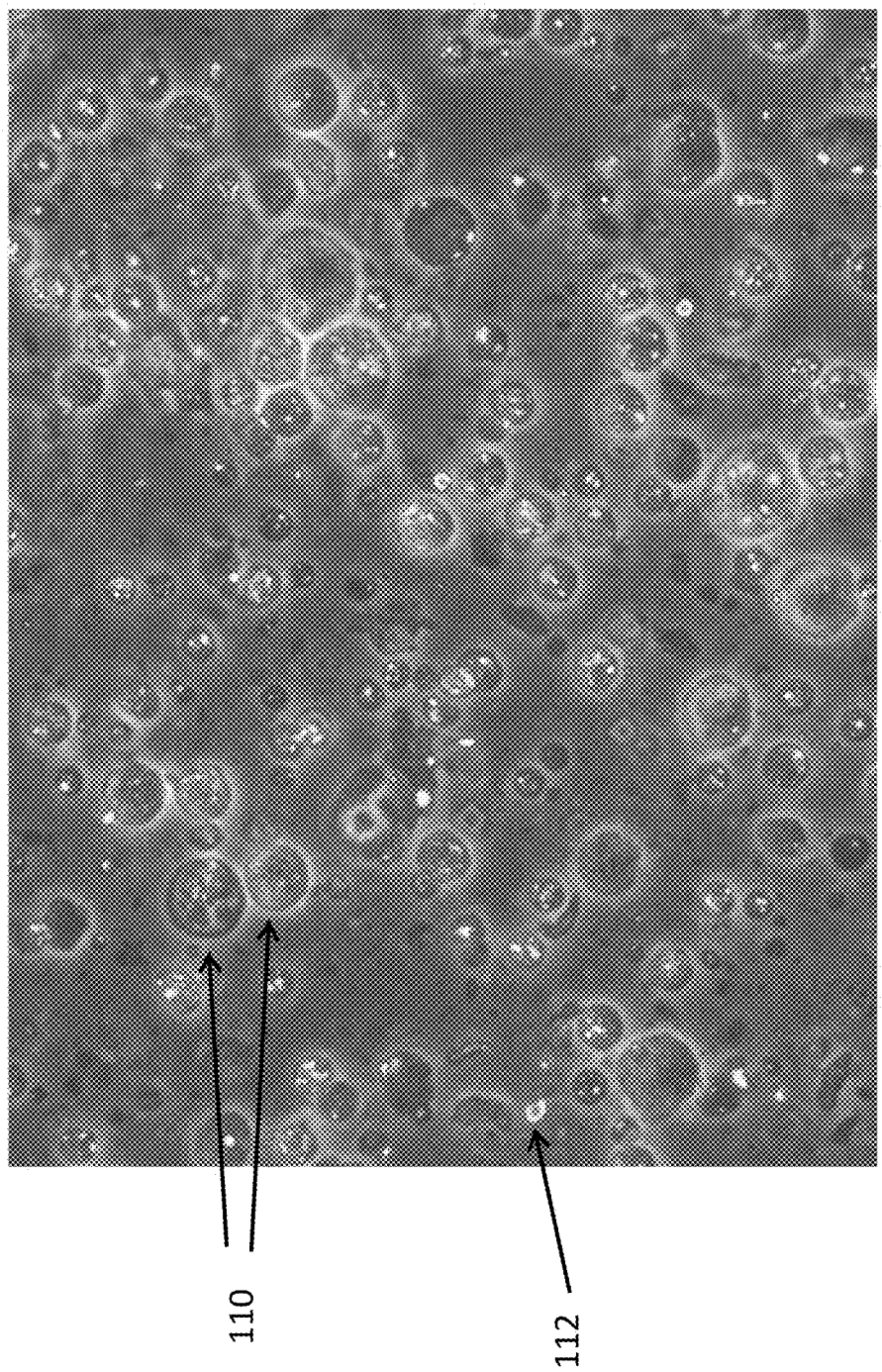
FIG. 11A and FIG. 11B depict a suspension of DepoMLX particles under phase contrast magnification using a 40× objective lense.
Figure 11B:
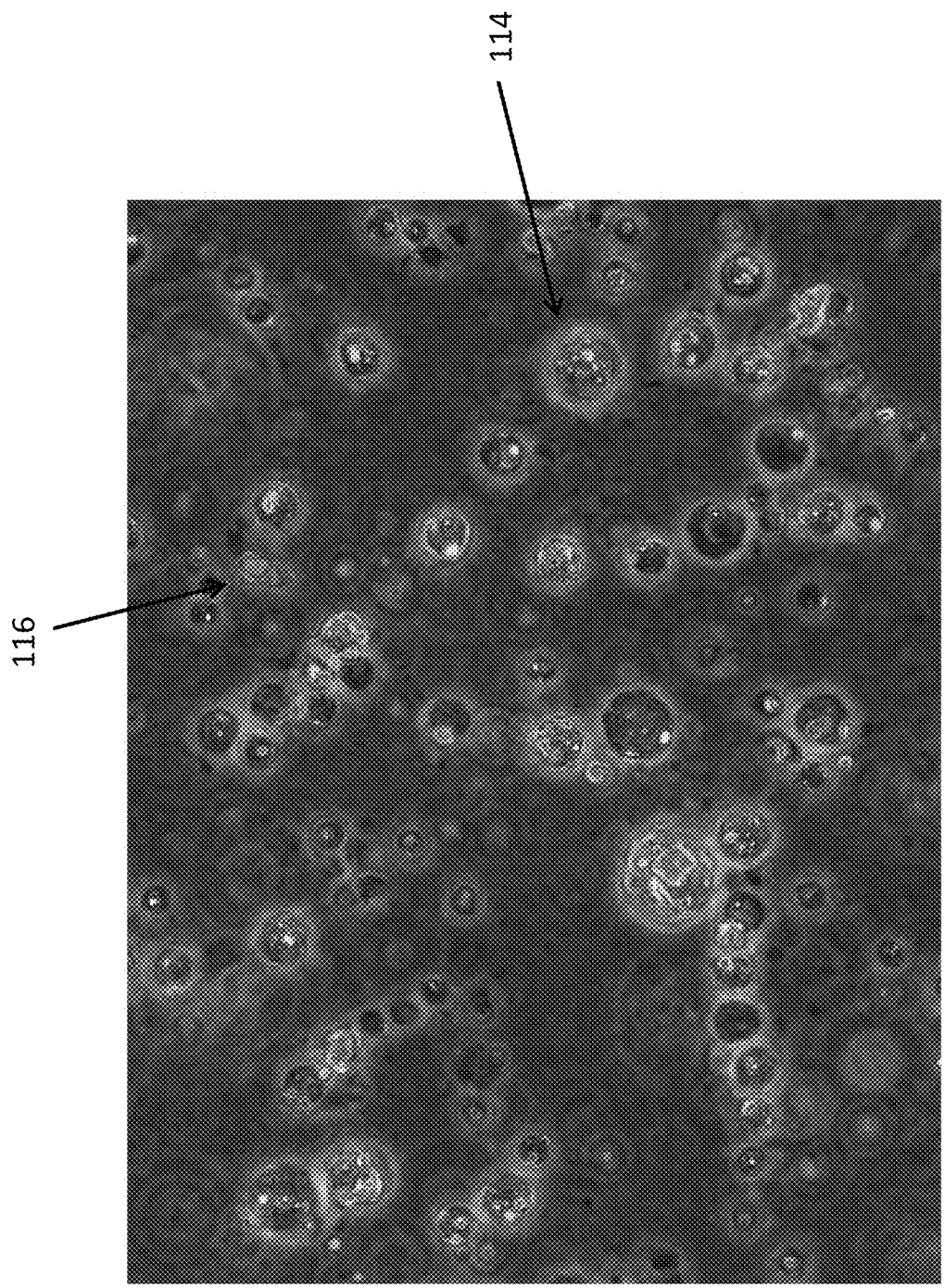
Figure 12:
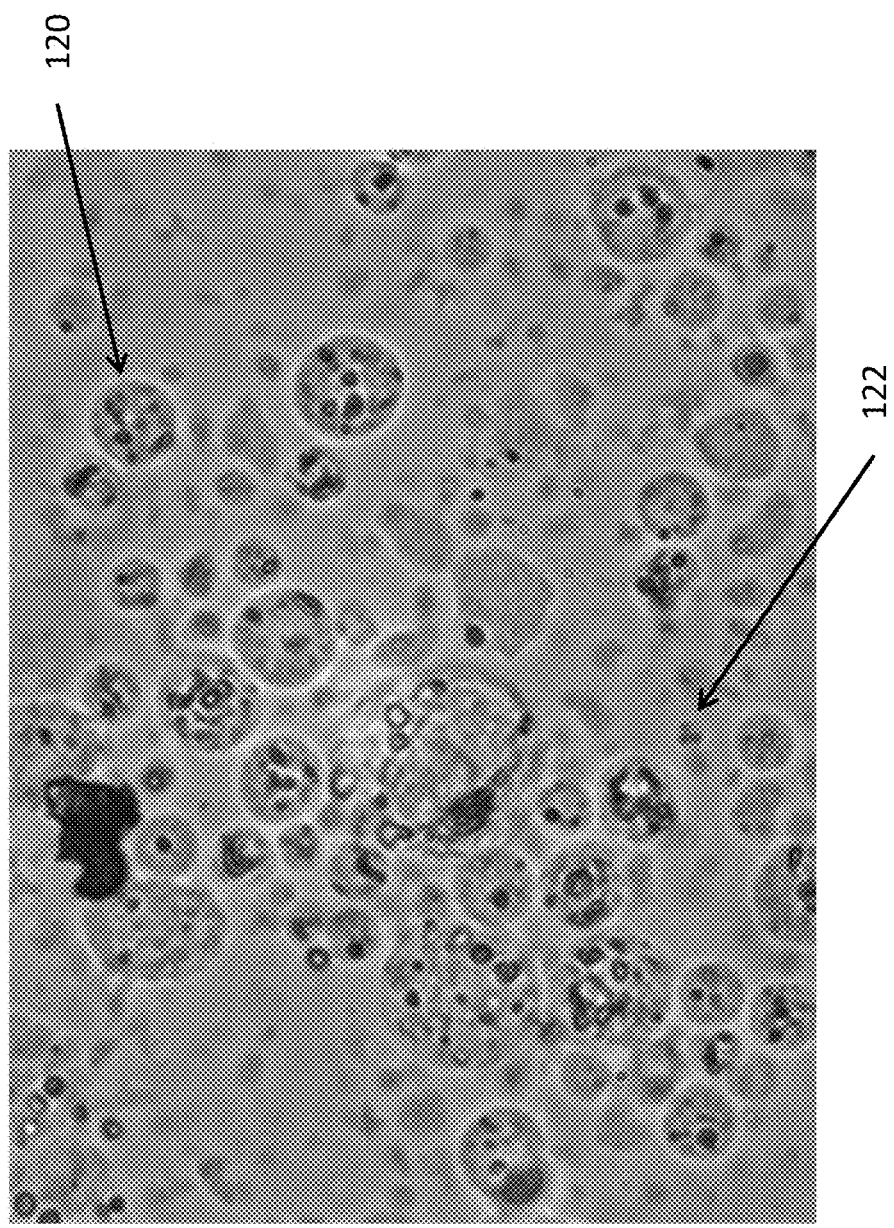
FIG. 12 depicts DepoMLX particles under magnification using a 100× objective lenses.
Figure 13:
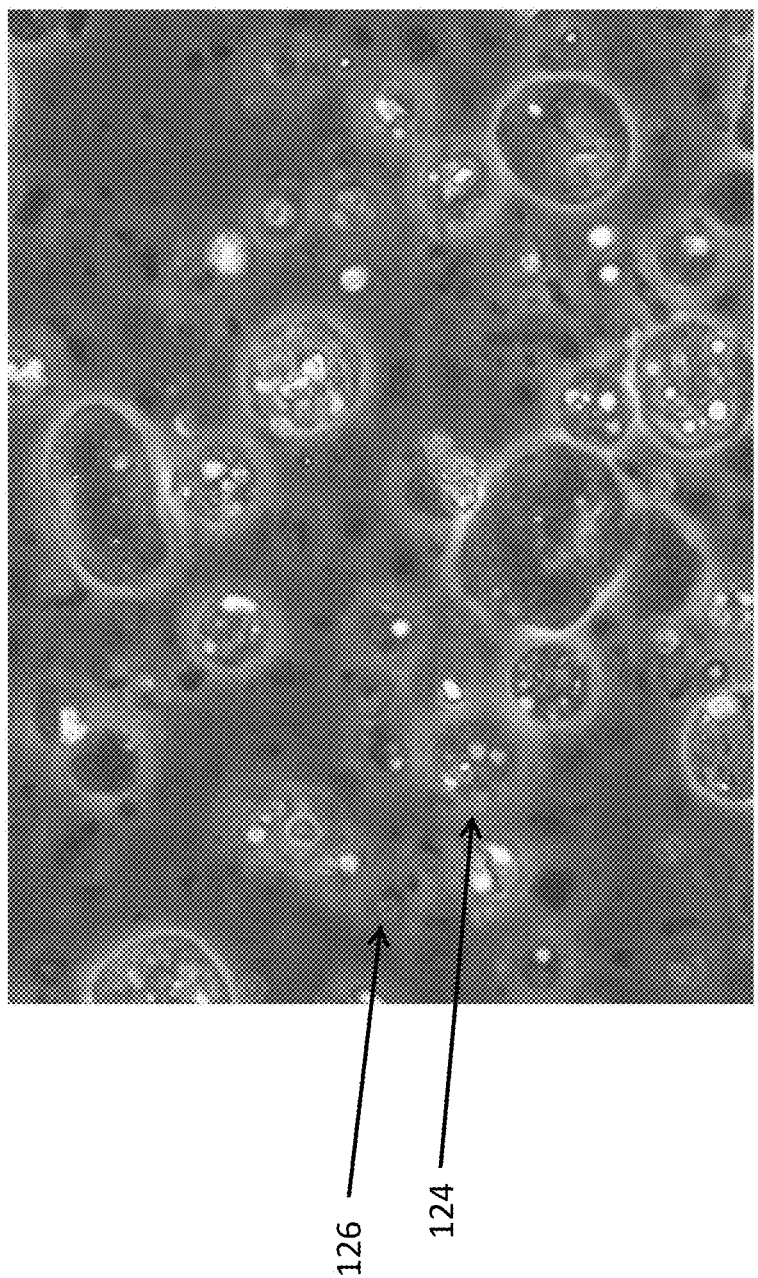
FIG. 13 depicts DepoMLX particles at 1000 times magnification. The image of FIG. 13 is a brightfield fluorescence image that includes phase contrast.

FIG. 11A and FIG. 11B depict DepoMLX particles at 400 times magnification. FIG. 11A and FIG. 11B are both microscope images of particle suspensions. FIG. 11A is an image acquired with an oil immersion lens, while FIG. 11B is an image in which the objective lens was not an oil-immersion lens. Structures 110 in FIG. 11A are MVL particles encapsulating $Zn(MLX)_2$, while structure 112 is unencapsulated $Zn(MLX)_2$. In FIG. 11B, structure 114 is an MVL particle encapsulating $Zn(MLX)_2$, while structure 116 is unencapsulated $Zn(MLX)_2$. FIG. 12 and FIG. 13 depict DepoMLX particles taken with 100× objective lenses. FIG. 12 is brightfield image with fluorescence overlay, while the image of FIG. 13 includes phase contrast. In FIG. 12, structure 120 is an MVL particle encapsulating $Zn(MLX)_2$, while structure 122 is unencapsulated $Zn(MLX)_2$. In FIG. 13, structure 124 is an MVL particle encapsulating $Zn(MLX)_2$, while structure 126 is unencapsulated $Zn(MLX)_2$.

Some embodiments disclosed herein are directed to formulations of MVLs, comprising a zinc meloxicam complex microparticles, and one or more pH adjusting agents encapsulated in a first aqueous phase of the MVLs. The MVLs also comprise lipid components. In some embodiments, the lipid components of the MVLs comprising at least one amphipathic lipid selected from phosphatidyl choline or salts thereof, phosphatidyl glycerol or salts thereof, or combinations thereof, and at least one neutral lipid. In some embodiments, the MVLs may optionally comprise additional therapeutic agent(s). In some other embodiments, MLX is the only therapeutic agent in the MVLs. In some embodiments, the MVL particles are suspended in a suspending solution.

Zinc-Meloxicam Complex

In some preferred embodiments of the zinc meloxicam complex microparticle MVL formulations described herein, the zinc salt used for forming a complex with meloxicam, including for example, zinc chloride. In some such embodiments, meloxicam forms a complex with the zinc salt to form a zinc meloxicam complex. In some further embodiments, such zinc meloxicam complex is in the form of microparticles. In some such embodiments, the zinc meloxicam complex includes a molar ratio of zinc to meloxicam about 1:4 to 4:1, about 1:3 to 3:1, about 1:2 to 2:1, about 2:1, or about 1:1. One of ordinary skill in the art would understand that in the context of the present description, both zinc and meloxicam bear formal charges in the zinc meloxicam complex. Zinc is in the cationic form $Zn^{2+}$, while meloxicam is negatively charged. In some embodiments, the complex as a whole does not bear any positive or negative charge.

In one particular embodiment, the zinc to meloxicam molar ratio is 1:2 and the zinc meloxicam complex is $Zn(MLX)_2$. In further embodiments, the zinc meloxicam complex has the formula $Zn(MLX)_2(OH_2)_2$. In some further embodiments, the zinc meloxicam complex may exist as a microcrystal in its hydrate or solvate form. In one example, the zinc meloxicam microcrystal has a formula $Zn(MLX)_2 \cdot 4H_2O$. A microcrystalline form of $Zn(MLX)_2$ was prepared and isolated for characterization.

Figure 1B:
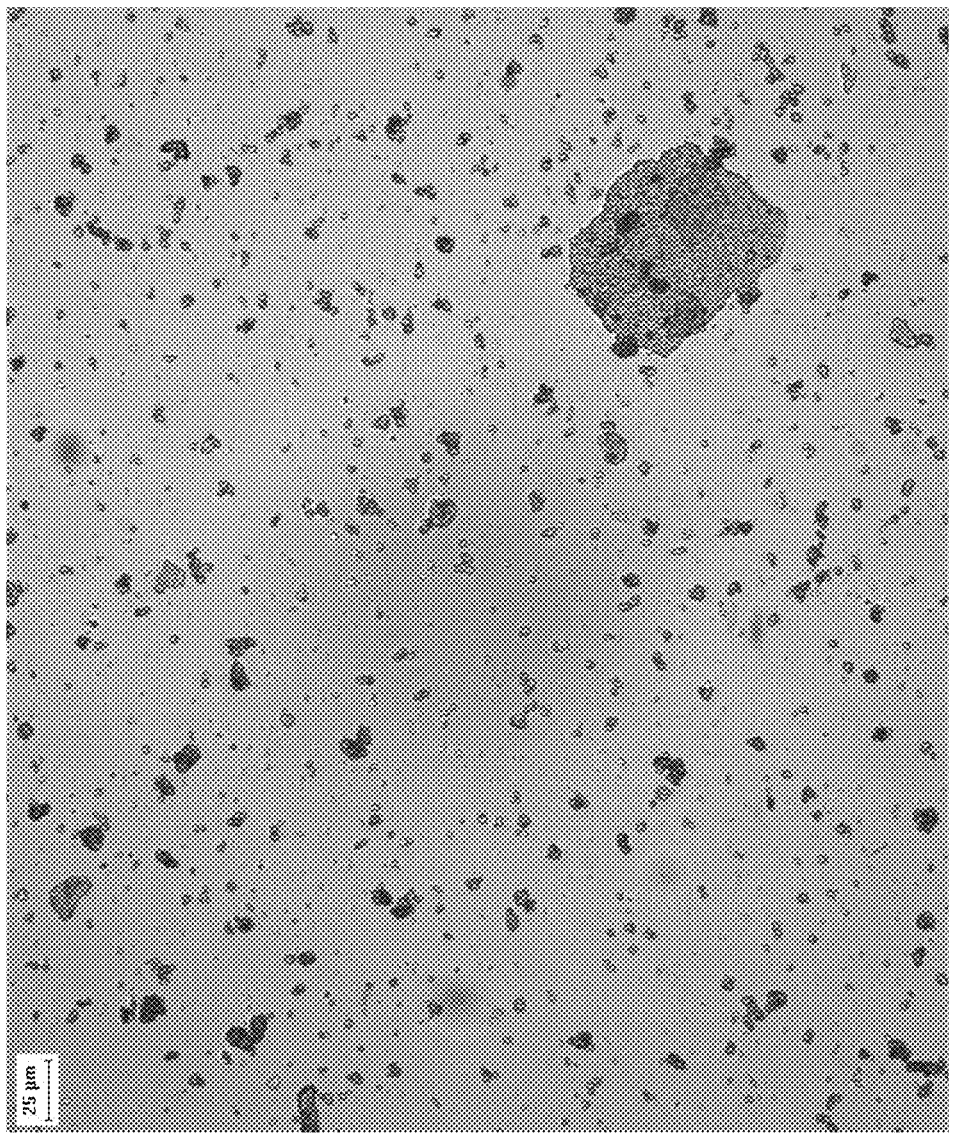
Figure 2:
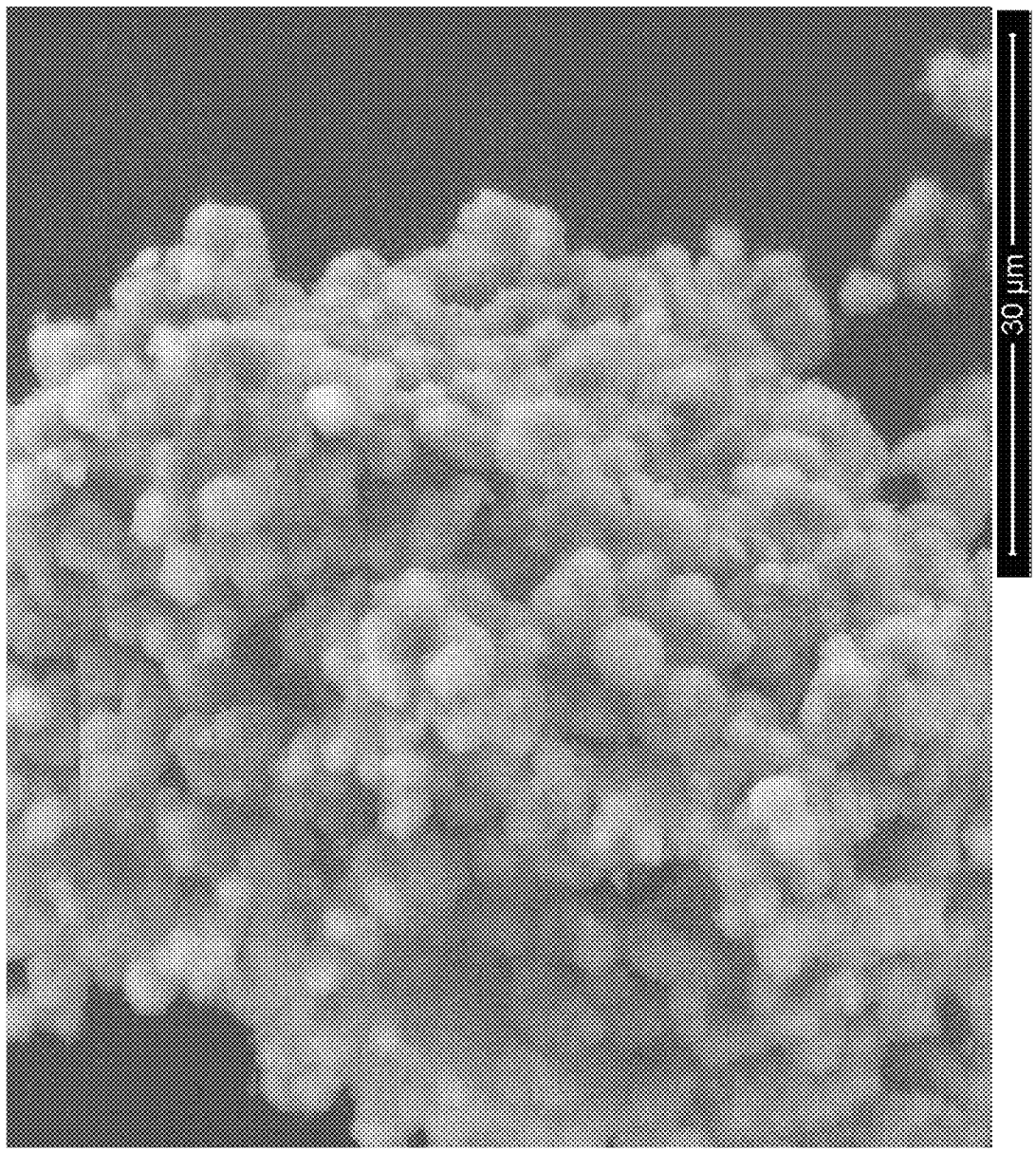
FIG. 2 is a scanning electron micrograph (SEM) of zinc meloxicam complex microparticles of the formula $Zn(MLX)_2$.
Figure 3:
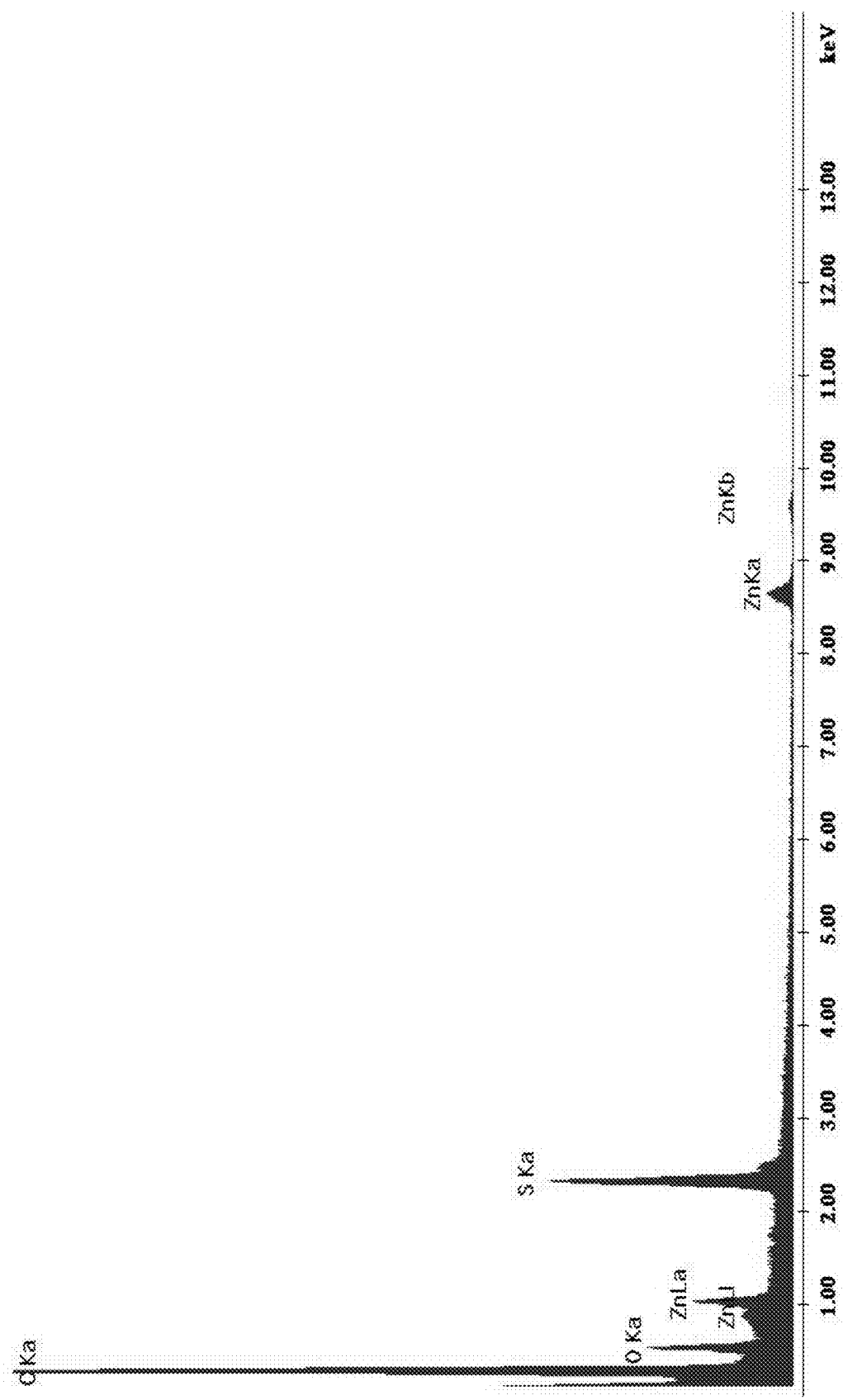
FIG. 3 is an Energy Dispersive X-ray (EDX) analysis of $Zn(MLX)_2$.
Figure 4A:
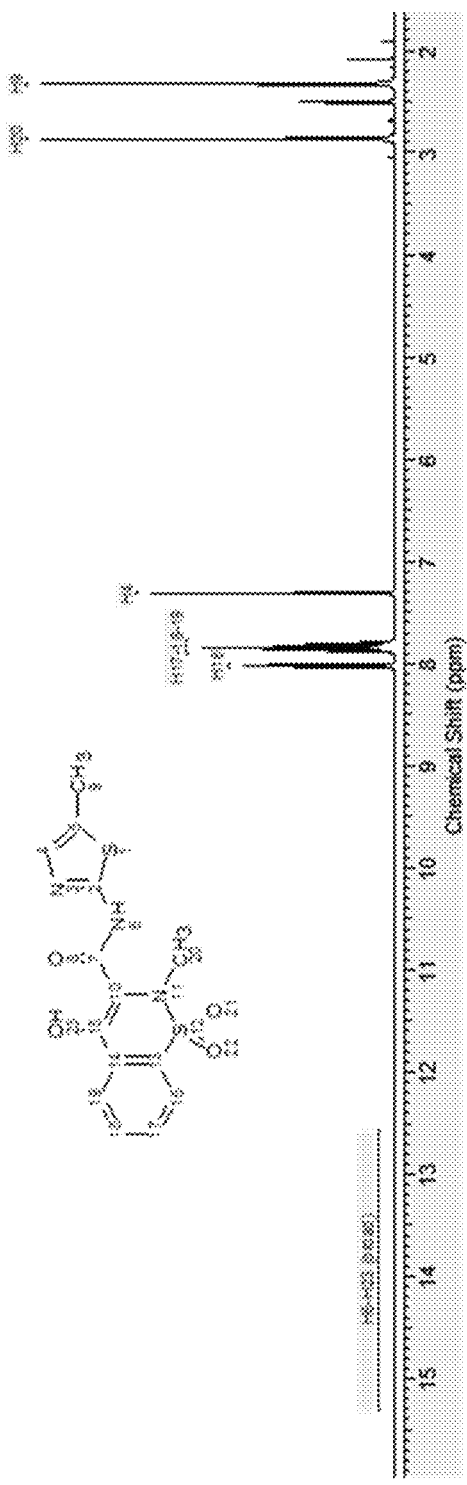
FIG. 4A is a proton nuclear magnetic resonance ($^1$H NMR) of meloxicam.
Figure 4B:
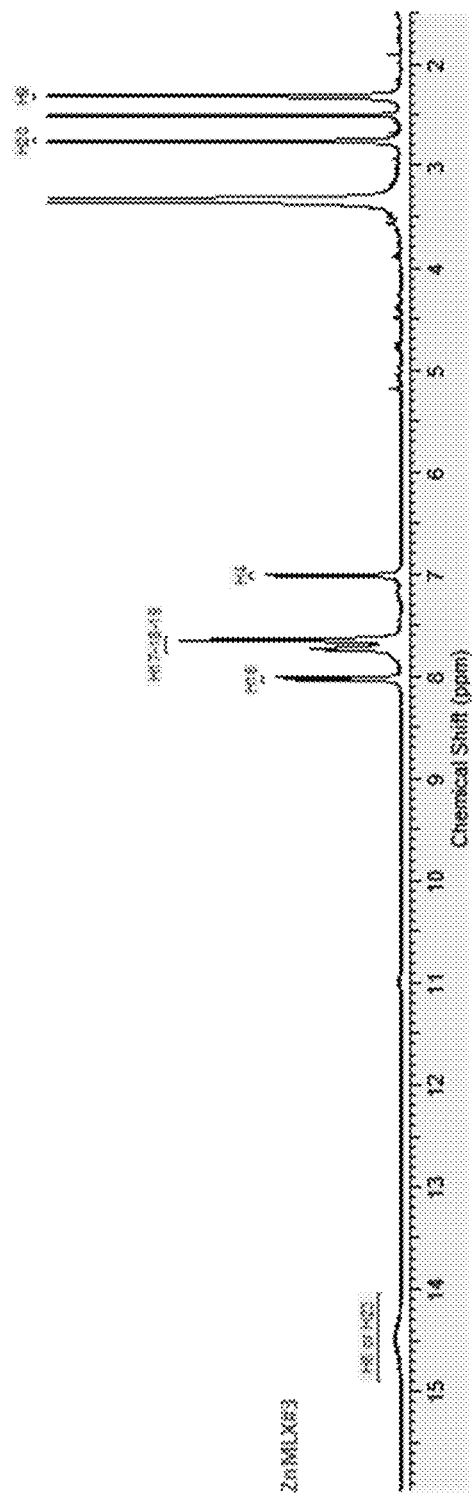
FIG. 4B is a $^1$H NMR of meloxicam in a zinc meloxicam complex of the formula $Zn(MLX)_2$.

FIGS. 1A and 1B depict an optical micrograph characterizing a microcrystalline form of $Zn(MLX)_2$ at two different scales 10 µm and 25 µm. The microcrystals are of irregular shapes with some large thin plate-like particles. A large presence of fines was observed. FIG. 2 is scanning electron micrograph (SEM) of a zinc meloxicam complex microparticle of the formula $Zn(MLX)_2$. FIG. 3 is the energy dispersive X-ray analysis (EDX) of $Zn(MLX)_2$, which confirms the presence of Zn in the sample. FIG. 4A is the $^1$H NMR of free unencapsulated meloxicam and FIG. 4B is the $^1$H NMR of meloxicam in $Zn(MLX)_2$. The NMRs were collected at 400 MHz in DMSO-d6. Free meloxicam was soluble while $Zn(MLX)_2$ was poorly soluble in DMSO-d6 and substantially insoluble in $CDCl_3$. Only one exchangeable proton was visible in the region>10 ppm for $Zn(MLX)_2$ (the second one might be very broad or in full exchange). In addition, broader resonance peaks were observed for $Zn(MLX)_2$ with respect to free meloxicam and a major shielding effect for H4 proton of the meloxicam was also observed as shown in FIG. 4B.

In some embodiments, the zinc meloxicam complex is partially or substantially insoluble in the first aqueous phase. $Zn(MLX)_2$ is insoluble below neutral pH, but readily solubilized at higher pH whereby zinc and MLX freely dissociate. The dissociation of $Zn(MLX)_2$ to MLX upon release from zinc meloxicam complex microparticle MVL has been also demonstrated in in vitro and in vivo studies described herein. In product analytical testing, upon dissolution in a water/solvent mixture, only fully dissociated MLX is seen on chromatograms.

Figure 5:
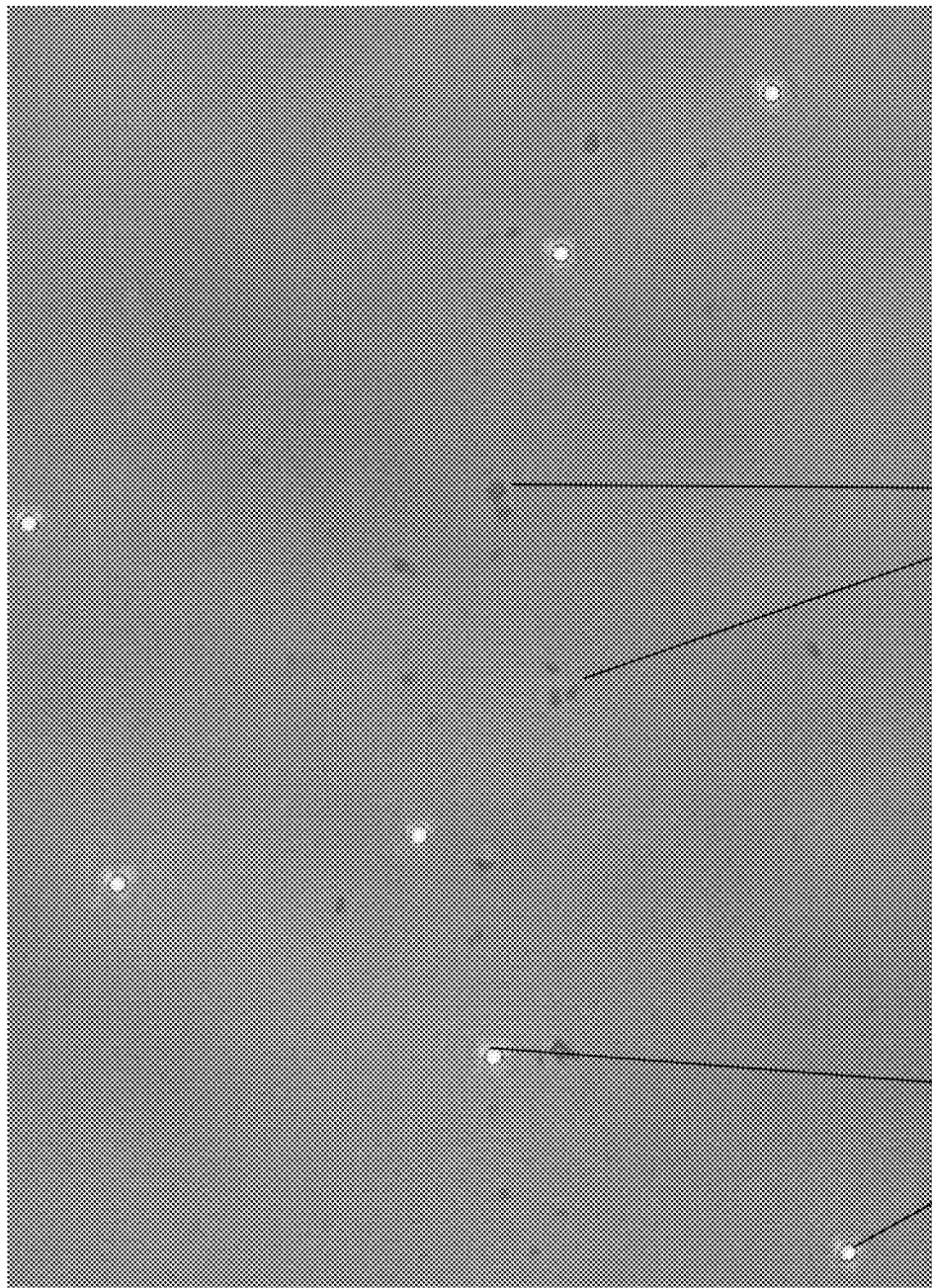
FIG. 5 is an optical micrograph of the zinc meloxicam complex microparticle $Zn(MLX)_2$ microcrystals with standard 1 micron polystyrene microspheres as reference.

FIG. 5 is an optical micrograph of the zinc meloxicam complex $Zn(MLX)_2$ microparticle microcrystals obtained from the suspension with standard polystyrene microspheres as reference. The polystyrene microspheres are Duke Standards Microsphere Size Standards (NIST Traceable Mean Diameter) polystyrene microspheres with certified mean diameter 1.030 µm±0.011 µm. The $Zn(MLX)_2$ microcrystals are the dark irregularly shaped particles and 1 µm Standard polystyrene microspheres are the white spherical particles. It was surprisingly found that some of the $Zn(MLX)_2$ microcrystals have a particle size of less than 1 µm according to the micrograph.

pH Modifying Agents

The pH modifying agents that may be used in the present MVL formulations are selected from organic acids, organic bases, inorganic acids, or inorganic bases, or combinations thereof. Suitable inorganic acids (also known as mineral acids) that can be used in the present application include, but are not limited to hydrochloric acid (HCl), sulfuric acid ($H_2SO_4$), phosphoric acid ($H_3PO_4$), nitric acid ($HNO_3$), etc. Suitable organic acids that can be used in the present application include, but are not limited to acetic acid, aspartic acid, citric acid, formic acid, glutamic acid, glucuronic acid, lactic acid, malic acid, tartaric acid, etc. Suitable organic bases that can be used in the present application include, but are not limited to histidine, arginine, lysine, tromethamine (Tris), etc. Suitable inorganic bases that can be used in the present application include, but are not limited to sodium hydroxide, calcium hydroxide, magnesium hydroxide, potassium hydroxide, etc.

In some embodiments of the formulations described herein, the pH adjusting agents further comprise one or more organic acids, one or more organic bases, or combinations thereof. In some embodiments, the one or more organic acids include tartaric acid. In some embodiments, the one or more organic bases include lysine or histidine or combinations thereof. In some embodiments, the internal pH of the MVLs is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0, or within a range defined by any two of the preceding pH values. In some embodiments, the internal pH of the MVLs is from about 5.6 to about 6.6. In one embodiment, the internal pH of the MVLs is about 5.8.

In some embodiments of the formulations described herein, the MVL particles are suspended in a suspending solution. The suspending solution may comprise a pH adjusting agent, and/or may perform a buffering function. The suspending solution defines the external pH of the MVL formulation. In some embodiments, the pH of the suspending solution is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, or 10.5, or within a range defined by any two of the preceding pH values. In some embodiments, the pH of the suspending solution is from about 5.5 to 8.0. In one embodiment, the pH of the suspending solution is about 6.1. In some embodiments, the suspending solution is the same as the second aqueous phase of the MVLs.

Tonicity Agents

In some embodiments of the formulations described herein, the first aqueous phase of the MVLs further comprises one or more tonicity agents. Tonicity agents sometimes are also called osmotic agents. Non-limiting exemplary osmotic agents suitable for the MVL formulation of the present application include monosaccharides (e.g., glucose, and the like), disaccharides (e.g., sucrose and the like), polysaccharide or polyols (e.g., sorbitol, mannitol, Dextran, and the like), or amino acids.

In some embodiments, the one or more tonicity agents may be selected from an amino acid, a sugar, or combinations thereof. In some further embodiments, the one or more tonicity agents are selected from dextrose, sorbitol, sucrose, lysine, or combinations thereof.

In some embodiments, the osmolality of the first aqueous phase of the MVLs is about 230, 240, 250, 260, 270, 280, 290, 300, 310, 320, 330, 340, 350, 360, or 370 mOsm/kg, or within a range defined by any two of the preceding values. In some embodiments, the osmolality of the first aqueous phase of the MVLs is from about 250 mOsm/kg to about 350 mOsm/kg. In some further embodiments, the osmolality of the first aqueous phase of the MVLs is from about 280 mOsm/kg to about 320 mOsm/kg. In one embodiment, the osmolality of the first aqueous phase of the MVLs is about 290 mOsm/kg. In further embodiments, the first aqueous suspension may have an osmolality of about 370 to about 1000 mOsm/kg, for example, about 650 to about 800 mOsm/kg.

Lipid Components

In some embodiments of the formulations described herein, the lipid components of the MVLs comprise at least one amphipathic lipid and at least one neutral lipid. In some further embodiments, the lipid components contain phosphatidyl choline or salts thereof, phosphatidyl glycerol or salts thereof, and at least one triglyceride. Non-limiting exemplary phosphatidyl cholines include dioleyl phosphatidyl choline (DOPC), dierucoyl phosphatidyl choline or 1,2-dierucoyl-sn-glycero-3-phosphocholine (DEPC), 1,2-didecanoyl-sn-glycero-3-phosphocholine (DDPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC). Non-limiting examples of phosphatidyl glycerols include dipalmitoylphosphatidylglycerol or 1,2-dipalmitoyl-sn-glycero-3-phospho-rac-(1-glycerol) (DPPG), 1,2-dierucoyl-sn-glycero-3-phospho-rac-(1-glycerol) (DEPG), 1,2-dilauroyl-sn-glycero-3-phospho-rac-(1-glycerol) (DLPG), 1,2-dimyristoyl-sn-glycero-3-phospho-rac-(1-glycerol)

(DMPG), 1,2-dioleoyl-sn-glycero-3-phospho-rac-(1-glycerol) (DOPG), 1,2-distearoyl-sn-glycero-3-phospho-rac-(1-glycerol) (DSPG), 1-palmitoyl-2-oleoyl-sn-glycero-3-phospho-rac-(1-glycerol) (POPG), or salts thereof, for example, the corresponding sodium salts, ammonium salts, or combinations of the salts thereof. Non-limiting exemplary triglycerides include triolein (TO), tripalmitolein, trimyristolein, trilinolein, tributyrin, tricaproin, tricaprylin, and tricaprin. The fatty chains in the triglycerides can be all the same, or not all the same (mixed chain triglycerides), or all different. In further embodiments, the phosphatidyl choline and the phosphatidyl glycerol are present in MVLs in a mass ratio of about 10:1 to about 3:1.

In some embodiments, the phosphatidyl choline is dierucoyl phosphatidyl choline (DEPC). In some embodiments, the phosphatidyl glycerol is dipalmitoyl phosphatidyl glycerol (DPPG). In some embodiments, the triglyceride is tricaprylin. In some embodiments, the lipid components further comprise cholesterol. In further embodiments, the DEPC and the DPPG are present in MVLs in a mass ratio of DEPC:DPPG of about 10:1 to about 1:1, or about 10:1 to about 3:1.

Particle Sizes

In some embodiments of the formulations described herein, the meloxicam encapsulated multivesicular liposomes have a median particle diameter of about 5, 10, 15, 20, 25, 30, 35, 40, 45, 50, 55, 60, 65, 70, 75, 80, 85, 90, 95, or 100 µm, or within a range defined by any two of the preceding values. In some further embodiments, the multivesicular liposomes have a median particle diameter ranging from about 10 µm to about 50 µm. In some further embodiments, the multivesicular liposomes have a median particle diameter ranging from about 25 µm to about 40 µm. In still some further embodiments, the multivesicular liposomes have a median particle diameter ranging from about 15 µm to about 30 µm.

Potency

In some embodiments of the formulations described herein, the concentration or potency of meloxicam in the final multivesicular liposome formulation is about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 16, 17, 18, 19, 20, or 25 mg/mL, or within a ranged defined by any two of the preceding values. In some such embodiments, the concentration of meloxicam in the multivesicular liposome formulation is from about 1.0 mg/mL to about 10.0 mg/mL. In some further embodiments, the concentration of the meloxicam in the multivesicular liposome formulation is from about 2.0 mg/mL to about 5.0 mg/mL. In some further embodiments, the concentration of the meloxicam in the multivesicular liposome formulation is from about 3.0 mg/mL to about 7.0 mg/mL. In some further embodiments, the concentration of the meloxicam in the multivesicular liposome formulation is from about 2.0 mg/mL to about 3.5 mg/mL. In still some further embodiments, the concentration of the meloxicam in the multivesicular liposome formulation is from about 2.0 mg/mL to about 3.3 mg/mL. In one embodiment, the concentration of the meloxicam in the multivesicular liposome formulation is about 2.4 mg/mL. In another embodiment, the concentration of the meloxicam in the multivesicular liposome formulation is about 3.0 mg/mL. In another embodiment, the concentration of the meloxicam in the multivesicular liposome formulation is about 5.0 mg/mL. In another embodiment, the concentration of the meloxicam in the multivesicular liposome formulation is about 7.0 mg/mL.

In some embodiments, the zinc meloxicam complex microparticle MVL formulations may further comprise unencapsulated meloxicam, for example, free meloxicam, free meloxicam complex, or free zinc meloxicam complex microparticles. In some such embodiments, the unencapsulated meloxicam is less than about 60% by weight, less than about 50% by weight, less than about 40% by weight, less than about 30% by weight, or less than about 25%, or less than about 20%, or less than about 15%, or less than about 10%, or less than about 5%, or less than about 2%, or less than about 1% of the total amount of meloxicam in the formulation, or in a range defined by any of the two preceding values. In some embodiments, a zinc meloxicam complex microparticle MVL formulation includes unencapsulated zinc meloxicam microparticles stabilized by phospholipids and/or surfactants. In further embodiments, a zinc meloxicam complex microparticle MVL formulation includes unencapsulated zinc meloxicam microparticles associated with surfaces of the MVL particles.

In any embodiments of the formulations described herein, the MVL formulation is substantially free of cyclodextrin, for example, containing less than about 1%, about 0.5%, about 0.1%, or about 0.01% cyclodextrin. In one embodiment, the MVL formulation is free of cyclodextrin.

Other Formulations of Zinc Meloxicam Complex Microparticles

Some alternative embodiments described herein are directed to non-MVL formulations comprising the zinc meloxicam complex microparticles described herein, for example, the zinc meloxicam complex microparticles having a median particle diameter of about 50 µm or less, about 5 µm or less, about 0.5 µm or less, about 0.2 µm or less, and a pharmaceutically acceptable carrier. In some embodiments, the zinc meloxicam complex microparticles are unencapsulated. The formulation containing the zinc meloxicam complex microparticles may provide a controlled or sustained release of meloxicam due to the poor solubility of the zinc meloxicam complex in water. In some other embodiments, the formulation comprises one or more surfactants, for example, phospholipids and/or synthetic surfactants. In some other embodiments, the formulation is a liposomal formulation comprising one or more lipids. In some such embodiments, at least a portion of the zinc meloxicam complex microparticles is encapsulated in the lipids or surfactants in the form of unilamellar or multilamellar vesicles, or stabilized by surfactants on their surfaces. Various surfactants may be used in the non-MVL formulations of the zinc meloxicam complex microparticle formulations, including phospholipids, anionic surfactants, cationic surfactants, zwitterionic surfactants or nonionic surfactants. Non-limiting examples of the anionic surfactants include sulfates, sulfonates, phosphate esters, and carboxylates, such as ammonium lauryl sulfate, sodium lauryl sulfate (sodium dodecyl sulfate, SLS, or SDS), and the related alkyl-ether sulfates such as sodium laureth sulfate (sodium lauryl ether sulfate or SLES), and sodium myreth sulfate. Non-limiting examples of the cationic surfactants include quaternary ammonium salts, such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Non-limiting examples of the zwitterionic surfactants including betaines, phosphatidylserine, phosphatidylethanolamine, phosphatidylcholine, and sphingomyelins. Non-limiting examples of nonionic surfactants include fatty alcohols (such as cetyl alcohol, stearyl alcohol, and cetostearyl alcohol, and oleyl alcohol), polyalkylene glycol alkyl ethers, glycerol alkyl esters, and sorbitan alkyl esters. In one embodiment, the zinc meloxicam complex has the formula $Zn(MLX)_2$.

In some embodiments, the MLX-MVL, zinc meloxicam complex microparticle MVL or other non-MVL zinc meloxicam complex microparticle formulations described herein optionally include a pharmaceutically acceptable carrier for injection.

In some embodiments of the various zinc meloxicam complex microparticle formulations described herein, the formulation is pharmaceutically acceptable for administration by injection, such as subcutaneous injection, intraarticular injection, intramuscular injection, intraperitoneal injection, or any other parenteral administration means such as those known in the pharmaceutical art. The composition can further be administered by infiltration, instillation or infusion as known in the pharmaceutical art. In one embodiment, the formulation is suitable for administration by local injection into a surgical site. In another embodiment, the formulation is suitable for wound instillation. In yet another embodiment, the formulation is suitable for direct instillation into an open wound, a fluid filled compartment or a body cavity. Non-MVL formulations, such as surfactant-stabilized formulations, can be administered intravenously or by infusion.

Methods of Manufacturing

Some embodiments provide methods for preparing formulations of meloxicam encapsulated within multivesicular liposomes which provide modulated and controlled release of meloxicam. In some embodiments, the process as described herein is a continuous manufacturing process. In some embodiments, certain steps or each step of the process may be performed under a sterile or aseptic condition. The instant zinc meloxicam complex microparticle MVL formulations are made by the following process. Generally, apparatuses and processes described in H. Hartounian et al., U.S. Pat. No. 9,585,838 (2017), which is incorporated by reference herein in its entirety, may be used in any stage of the preparation of MVLs. For example, an apparatus depicted in any of FIG. 1, 2, 4, 5, or 6 of U.S. Pat. No. 9,585,838, or a process carried out by such an apparatus, may be used.

Preparation of Zinc Meloxicam Complexes Microparticles and Formulations Thereof

First, an aqueous MLX solution and an aqueous solution containing a divalent metal cationic salt are prepared. The two solutions are mixed together to form a meloxicam metal complex. The mixture containing the meloxicam complex may be the first aqueous phase of MVLs. Preferably, the divalent cationic salt is a zinc salt. Non limiting examples of the zinc salts include zinc chloride ($ZnCl_2$), zinc nitrate ($Zn(NO_3)_2$), zinc chlorate ($Zn(ClO_3)_2$), zinc sulfate ($ZnSO_4$), zinc phosphate ($Zn_3(PO_4)_2$), or zinc acetate ($Zn(O_2CCH_3)_2$), or hydrates or combinations thereof. In one particular example, the zinc salt is zinc chloride.

It was observed that simply mixing a zinc salt aqueous solution with a meloxicam solution does not readily form a zinc meloxicam complex. As noted above, meloxicam is very lipophilic and has very low water solubility at neutral or acidic conditions. Therefore, the pH of the meloxicam aqueous solution must be adjusted to be basic to enable sufficient dissolution of the meloxicam. In contrast, zinc chloride forms zinc hydroxide precipitate under a basic pH. If the pH of the zinc salt aqueous solution is too high, zinc cation will precipitate out of the solution in the form of zinc hydroxide, therefore leaving little or no zinc cation in the solution phase for reaction with meloxicam. Therefore, the pH of the zinc chloride aqueous solution and the meloxicam solution must be optimized to enable the formation of the zinc meloxicam complex microparticles in good yields. In some embodiments, the pH of the zinc salt solution is from about 4.5 to about 6.0, and the pH of the meloxicam solution is from about 7.5 to about 10.0. In some further embodiments, the pH of the zinc salt solution is from about 5.0 to about 5.5. In one embodiment, the pH of the zinc salt solution is about 5.2. In another embodiment, the pH of the zinc salt solution is about 5.5. In some further embodiments, the pH of the meloxicam solution is from about 8.0 to about 9.0. In one embodiment, the pH of the meloxicam solution is about 8.2. In another embodiment, the pH of the meloxicam solution is about 8.5. In some embodiments, after mixing the zinc chloride solution and the meloxicam solution the pH of the resulting mixture is about 6.6. In some embodiments, the pH of the zinc meloxicam complex microparticle suspension is about 6.6.

It was found that the meloxicam solution and zinc salt solution formed the desired zinc meloxicam complex microparticles when conditions of osmolality and concentration were controlled. Thus, the meloxicam solution and/or zinc salt solution may include additional excipients. The additional excipients may be one or more of a tonicity agent, a solubilizing agent, an amino acid, an organic acid, an organic base, and combinations thereof. The additional excipients may be selected from tartaric acid, lysine, sucrose, histidine, and combinations thereof.

Upon mixing of the aqueous MLX solution with the zinc chloride aqueous solution in proper pH and other conditions, a complex of zinc meloxicam forms as a suspension due to the low aqueous solubility of the zinc meloxicam complex. The zinc meloxicam complex microparticle suspension can be used to form MVLs, as the first aqueous suspension, or can be subjected to further processing steps. It was found that it was important to ensure that the first aqueous suspension is within a proper pH range for subsequent processes. In some embodiments, the pH of the zinc meloxicam complex microparticle suspension after the zinc meloxicam complex microparticles are formed is from about 5.0 to about 8.0, or from about 6.2 to about 7.0, or preferably from about 6.55 to about 6.75. Selection of appropriate pH ensures that zinc and meloxicam ions are present to form the complex. It was surprisingly discovered that a narrow pH range was needed to form zinc meloxicam complex to completion. Under some conditions, zinc hydroxide or meloxicam would form and precipitate from the solution. In one embodiment, the zinc meloxicam complex microparticle suspension has a pH of about 6.6. In one embodiment, the first aqueous suspension or zinc meloxicam complex microparticle suspension has a pH of about 6.6. Subsequently, the first aqueous suspension or zinc meloxicam complex microparticle suspension may be titrated to a pH of about 5.8.

Generally, the zinc meloxicam complex can be in a MLX:zinc molar ratio of 2:1, 1:1, or 1:2. In one embodiment, the zinc meloxicam complex has the formula $Zn(MLX)_2$. In further embodiments, the zinc meloxicam complex has the formula $Zn(MLX)_2(OH_2)_2$. In some further embodiments, the zinc meloxicam complex may exist as a microcrystal in its hydrate or solvate form. In one example, the zinc meloxicam complex microcrystal has the formula $Zn(MLX)_2 \cdot 4H_2O$. $Zn(MLX)_2$ is an insoluble salt below neutral pH, but readily solubilizes at higher pH values, where zinc and MLX dissociate. It was also discovered that $Zn(MLX)_2$ dissociates at very low pH values. Upon release from the multivesicular liposomes, zinc meloxicam complex may dissociate to provide free meloxicam. Once the complexing is complete, the mixture can be titrated to a target pH and allowed to settle, for example, by gravity. After settling, the mixing vessel may be decanted to concentrate the zinc meloxicam complex microparticle suspension to the target meloxicam concentration. It was surprisingly found that controlling the pH of the zinc meloxicam complex suspension led to more rapid settling of the zinc meloxicam complex microparticles, enabling decantation of the supernatant to take place.

It was surprisingly discovered that, under processes described herein, the zinc meloxicam complex forms microparticles which require no further grinding and/or size reduction processing. The zinc meloxicam complex microparticles produced have sizes of one to a few microns median diameter, while some microparticles may form aggregates and may be seen as plates up to ~50 microns, as seen in FIGS. 1A, 1B, and 2. In some embodiments, zinc meloxicam complex microparticles having a median particle diameter of about 5 µm or less, about 2 µm or less, 1 µm or less, about 0.5 µm or less, or about 0.2 µm or less are formed. These spontaneously formed microparticles can readily be produced under sterile conditions in a sterilized container and easily encapsulated in the MVLs. In some embodiments, each of the zinc salt solution and the meloxicam solution is sterile or aseptic before mixing. In further embodiments, each of the zinc salt solution and the meloxicam solution is sterile filtered before combining.

It was also surprisingly observed that the zinc meloxicam complex $Zn(MLX)_2$ microparticles have low solubility in both aqueous solution and volatile organic solvents typically used in the MVL manufacturing processes (e.g., chloroform and methylene chloride). These microparticles are superior to the aqueous meloxicam solution used in the prior art processes for the manufacturing of meloxicam encapsulated multivesicular liposomes. As noted above, meloxicam is rather lipophilic and can readily pass through the lipid membranes of the MVLs once encapsulated, thus resulting in leaking from the internal aqueous chambers of the MVLs. Because of the low aqueous solubility of the zinc meloxicam complex microparticles, the leaking problem can be circumvented. Furthermore, the zinc meloxicam complex microparticles do not contribute to the osmolality of the MVL particles due to their substantial insolubility in the internal aqueous chambers of the MVLs. Therefore, they do not cause swelling of the MVL particles and allow for higher loading of the meloxicam. Finally, the biocompatibility of zinc and its additional benefits of promoting wound healing render the zinc meloxicam complex superior for the treatment of pain, in particular pain from injury or post-surgical sites.

In any embodiment of the processes for preparing the zinc meloxicam complex microparticles as described herein, the processes may be performed under a sterile or aseptic condition. In some further embodiments, the processes may be performed in a continuous fashion. In some still further embodiments, the processes may be performed by batch.

Additional pH adjusting agent may be added to the aqueous zinc meloxicam complex microparticle suspension. In some embodiments of the process described herein, the pH adjusting agents further comprise one or more organic acids, one or more organic bases, or combinations thereof. In some embodiments, the one or more organic acids include tartaric acid. In some embodiments, the one or more organic bases include lysine or histidine or combinations thereof. In some embodiments, the pH of the first aqueous suspension or the first aqueous phase of the multivesicular liposomes is from about 4.5 to about 7.0, preferably from about 5.6 to about 6.6. In one embodiment, the pH of the first aqueous phase of the multivesicular liposomes is about 5.8.

In some embodiments of the processes described herein, one or more tonicity agent is also added to the first aqueous suspension or the first aqueous phase of the MVLs. In some embodiments, the one or more tonicity agents include an amino acid, a sugar, or combinations thereof. In some embodiments, the one or more tonicity agents include sorbitol, sucrose, lysine, or combinations thereof. In some embodiments, the osmolality of the first aqueous phase of the MVLs is about 150 mOsm/kg to about 370 mOsm/kg, about 230 mOsm/kg to about 370 mOsm/kg, from about 250 mOsm/kg to about 350 mOsm/kg, or from about 280 mOsm/kg to about 320 mOsm/kg. In one embodiment, the osmolality of the first aqueous phase of the MVLs is about 290 mOsm/kg. In further embodiments, the first aqueous suspension may be hypertonic, having an osmolality of about 370 to about 1000 mOsm/kg, for example, about 650 to about 800 mOsm/kg. In such embodiments, the second aqueous phase may be exchanged for an isotonic suspending medium. Following such an exchange, the MVLs may swell to provide a zinc meloxicam complex microparticle MVL formulation as provided herein.

The first aqueous suspension and/or zinc meloxicam complex microparticle suspension may be further modified for use in preparing MVLs. For example, the first aqueous suspension and/or zinc meloxicam complex microparticle suspension may be allowed to settle, and the supernatant decanted. The suspending medium of the first aqueous suspension and/or zinc meloxicam complex microparticle suspension may be partially or completely exchanged. The suspending medium exchange may be such that conditions of osmolality, concentrations of one or more excipients, and concentration of meloxicam as zinc meloxicam complex microparticles, are adjusted. In some embodiments, the first aqueous suspension and/or zinc meloxicam complex microparticle suspension is suitable for preparation of a first aqueous phase of MVLs without further processing. In further embodiments, the first aqueous suspension and/or zinc meloxicam complex microparticle suspension is subject to a partial or complete suspending medium exchange. In further embodiments, the suspending medium comprises one or more of a pH adjusting agent, a surfactant, an amino acid, and a tonicity agent.

In some embodiments, one or more excipients in the zinc salt solution or the meloxicam solution is substantially removed from the zinc meloxicam complex microparticle suspension by exchange of the suspending medium. In further embodiments, the excipient substantially removed is zinc chloride, lysine, sucrose, histidine, or tartaric acid. In still further embodiments, the first aqueous suspension is substantially free of zinc chloride, lysine, sucrose, histidine, and/or tartaric acid, where substantially free is less than 20% of an amount in the zinc meloxicam complex microparticle suspension after the exchange.

The first aqueous suspension and/or zinc meloxicam complex microparticle suspension may be decanted to a selected level of meloxicam concentration. In various embodiments, the first aqueous suspension and/or zinc meloxicam complex microparticle suspension has a meloxicam concentration (in the form of zinc meloxicam complex microparticles) of about 0.5, 1.0, 1.5, 2.0, 2.5, 3.0, 3.5, 4.0, 4.5, 5.0, 6, 7, 8, 9, 10, 12, 14, 16, 18, 20, 25, 30, 35, or 40 mg/mL, or within a ranged defined by any two of the preceding values. In further embodiments, the first aqueous suspension and/or zinc meloxicam complex suspension has a meloxicam concentration (in the form of zinc meloxicam complex microparticles) of about 3 to about 15 mg/mL. In certain embodiments, the lipid concentrations in the lipid solution may be proportional to the concentration of meloxicam in the first aqueous suspension. In some embodiments, the first aqueous suspension and/or zinc meloxicam complex microparticle suspension may be concentrated by settling the zinc meloxicam complex microparticles, followed by decantation of supernatant. In further embodiments, a settled first aqueous suspension and/or zinc meloxicam complex microparticle suspension may be diluted to a desired concentration of meloxicam.

A "water-in-oil" type emulsion is produced by mixing a solution of lipids in an organic solvent, for example, chloroform or methylene chloride, and the first aqueous suspension of zinc meloxicam complex microparticles. The water-in-oil emulsion is formed from two immiscible phases, a lipid phase and the aqueous zinc MLX complex microparticle suspension. The lipid phase is made up of lipid components comprising at least one amphipathic lipid and at least one neutral lipid in a volatile organic solvent, and optionally cholesterol and/or cholesterol derivatives. The term "amphipathic lipid" refers to molecules having a hydrophilic "head" group and a hydrophobic "tail" group, which may, but need not, have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids are zwitterionic phospholipids, including phosphatidylcholines, phosphatidylethanolamines, sphingomyelins, lysophosphatidylcholines, and lysophosphatidylethanolamines. Also suitable are the anionic amphipathic phospholipids such as phosphatidylglycerols, phosphatidylserines, phosphatidylinositols, phosphatidic acids, and cardiolipins. Also suitable are the cationic amphipathic lipids such as acyl trimethylammonium propanes, diacyl dimethylammonium propanes, stearylamine, and the like. Preferred amphipathic lipids include dioleyl phosphatidyl choline (DOPC), dierucoylphosphatidylcholine or 1,2-dierucoyl-sn-glycero-3-phosphocholine (DEPC), and dipalmitoylphosphatidylglycerol or 1,2-dipalmitoyl-sn-glycero-3-phospho-rac-(1-glycerol) (DPPG). In certain embodiments, amphipathic lipids for the instant zinc meloxicam complex microparticle MVL formulations include DEPC and DPPG.

Suitable neutral lipids are triglycerides, propylene glycol esters, ethylene glycol esters, and squalene. Examples of triglycerides useful in the instant formulations and methods are triolein (TO), tripalmitolein, trimyristolein, trilinoelin, tributyrin, tricaproin, tricaprylin, and tricaprin. The fatty chains in the triglycerides useful in the present application can be all the same, or not all the same (mixed chain triglycerides), including all different. The propylene glycol esters can be mixed diesters of caprylic and capric acids.

In some embodiments of the processes described herein, the lipid components of the multivesicular liposomes include phosphatidyl choline or salts thereof, phosphatidyl glycerol or salts thereof, and at least one triglyceride. In some embodiments, the phosphatidyl choline is dierucoyl phosphatidyl choline (DEPC). In some embodiments, the phosphatidyl glycerol is dipalmitoyl phosphatidyl glycerol (DPPG). In some embodiments, the triglyceride is tricaprylin.

The concentrations of the amphipathic lipids, neutral lipids, and cholesterol present in the water-immiscible solvent used to make the MVLs typically range from 10-40 mM, 10-40 mM, and 10-60 mM, respectively. In some embodiments, the concentrations of the amphipathic lipids, neutral lipids, and cholesterol can be present in approximately a 1:1:1 molar concentration ratio. For example, the concentrations of the amphipathic lipids, neutral lipids, and cholesterol can be about 23 mM, about 24 mM, and about 24 mM, respectively, or about 37 mM, about 40 mM, and about 40 mM, respectively. If a charged amphipathic lipid is included, it is generally present in a lower concentration than the zwitterionic lipid.

Many types of volatile organic solvents can be used in the present process, including ethers, esters, halogenated ethers, hydrocarbons, halohydrocarbons, halocarbons, or freons. For example, diethyl ether, chloroform, methylene chloride, tetrahydrofuran, ethyl acetate, and any combinations thereof are suitable for use in making the formulations.

Optionally, other components are included in the lipid phase. Among these are antioxidants, antimicrobial preservatives, cholesterol, or plant sterols.

In certain embodiments, the first aqueous phase and/or first aqueous suspension includes a zinc meloxicam complex microparticle suspension, organic acids and bases, for example, tartaric acid, histidine, and a tonicity agent (e.g. sucrose). The lipid phase and first aqueous phase are mixed by mechanical turbulence, such as through use of rotating or vibrating blades, rotor/stator mixing, shaking, extrusion through baffled structures or porous pipes, or by ultrasound to produce a water-in-oil emulsion.

The water-in-oil emulsion can then be dispersed into a second aqueous phase by means described above, to form solvent spherules suspended in the second aqueous phase, a water-in-oil-in-water (w/o/w) emulsion ("second emulsion") is formed. For example, a three-fluid atomization nozzle as described in U.S. Patent Pub. No. 2011/0250264, which is incorporated by reference herein in its entirety, may be used. The term "solvent spherules" refers to a microscopic spheroid droplet of organic solvent, within which are suspended multiple smaller droplets of an aqueous phase. The second aqueous phase can contain additional components such as tonicity agents, pH adjusting agents, metal sequestering agents, or combinations thereof. For example, the second aqueous phase can comprise metal sequestering agents such as EDTA, tonicity agents such as sorbitol, dextrose, glucose, and/or sucrose, and one or more pH adjusting agents such as lysine, histidine, tartaric acid, etc. In some embodiments, the second aqueous phase does not include histidine.

In some embodiments of the zinc meloxicam complex microparticle MVL formulations described herein, the second aqueous phase used in the production, storage, or administration of the MVLs comprises one or more organic or inorganic acids, one or more organic or inorganic bases, or combinations thereof. In some such embodiments, the one or more organic acids comprise tartaric acid. In some such embodiments, the one or more organic bases comprise lysine or histidine. In some embodiments, the second aqueous phase pH is about 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9, or within a range defined by any two of the preceding pH values. In some embodiments, the pH of the second aqueous phase is from about 4.8 to about 7.2. In some further embodiments, the pH of the second aqueous phase is from about 6 to about 9. In some further embodiments, the pH of the second aqueous phase is from about 5.5 to about 7.0. In some further embodiments, the pH of the second aqueous phase is from about 6.4 to about 8.4. In further embodiments, the pH of the second aqueous phase is from about 7 to about 9. In one embodiment, the pH of the second aqueous phase is about 6.3. In one embodiment, the pH of the second aqueous phase is about 7.5. In one embodiment, the pH of the second aqueous phase is about 8.4. In one embodiment, the pH of the second aqueous phase is about 6.1.

The volatile organic solvent is then substantially removed from the spherules, for instance by surface evaporation from the suspension, or gas sparging. In some embodiments, the volatile water-immiscible organic solvent is removed from the water-in-oil-in-water emulsion by a spray process by dispersing or suspending the w/o/w droplets in a continuous gas phase using a three-fluid atomizing nozzle as described in U.S. Pub. No. 2011/0250264, which is incorporated by reference herein in its entirety. In some embodiments, the volatile water-immiscible organic solvent is substantially removed by dispersing the second emulsion into a circulating gas atmosphere, for example, through an atomizing nozzle or a nebulizer. When the solvent is substantially or completely evaporated, MVLs are formed. Gases which can be used for the evaporation include air, nitrogen, argon, helium, oxygen, hydrogen, and carbon dioxide. Alternately, the volatile solvent can be removed by sparging, rotary evaporation, diafiltration or with the use of solvent selective membranes, such as those described in WO 99/25319 and U.S. Pub. No. 2002/0039596, which are hereby incorporated by references in their entirety.

Using the process described herein, multivesicular liposomes comprising meloxicam can be manufactured with great efficiency. In some embodiments, the concentration of the meloxicam in the multivesicular liposome formulation ranges from about 0.5 mg/mL to about 25 mg/mL, from about 0.5 mg/mL to about 15.0 mg/mL, from about 1.0 mg/mL to about 10.0 mg/mL, from about 2.0 mg/mL to about 5.0 mg/mL, or from about 2.0 mg/mL to about 3.5 mg/mL. In some embodiments, the concentration of the meloxicam in the final MVL formulation is from about 2 mg/mL to about 8 mg/mL. In some preferred embodiments, the concentration of the meloxicam in the final MVL formulation is from about 2.2 mg/mL to about 3.3 mg/mL. In one embodiment, the concentration of the meloxicam in the final MVL formulation is about 2.4 mg/mL. In another embodiment, the concentration of the meloxicam in the final MVL formulation is about 3.0 mg/mL. In one embodiment, the concentration of the meloxicam in the final MVL formulation is about 7 mg/mL. In some embodiments, the formulation further comprises unencapsulated meloxicam, including but not limited to free meloxicam, free meloxicam complex, or free zinc meloxicam complex microparticles. For example, the final MVL formulation may include about 2.4 mg/mL meloxicam and have about 50% PPV. For further example, the final MVL formulation may include about 3 mg/mL meloxicam and have about 40% PPV.

In some embodiments of the processes described herein, the meloxicam encapsulated MVLs have a median particle diameter of from about 5 µm to about 100 µm, from about 10 µm to about 50 µm, or from about 25 µm to about 40 µm. In still some further embodiments, the multivesicular liposomes have a median particle diameter ranging from about 15 µm to about 30 µm.

Methods of Treatment and Administration

Some embodiments of the present disclosure are directed to methods of treating pain or inflammation, comprising administering a meloxicam encapsulated MVL formulation, in particular a zinc meloxicam complex microparticle MVL formulation as described herein to a subject in need thereof.

Some other embodiments of the present disclosure are directed to methods of treating pain or inflammation, comprising administering a formulation containing zinc meloxicam complex microparticles to a subject in need thereof. In some embodiments, the formulation does not include an MVL. In some such embodiments, the formulation is a sustained release formulation where the zinc meloxicam complex microparticles are not encapsulated. In some other embodiments, the formulation is a liposomal formulation encapsulating zinc meloxicam complex microparticles, such as a unilamellar liposome or multilamellar vesicle formulation. Such formulations also contain liposome-forming lipid(s) or surfactant(s). In unilamellar liposome and multilamellar vesicle formulations, free zinc meloxicam complex microparticles may also be present. Alternatively, the zinc meloxicam complex microparticles may be associated with one or more surfactants, for example, phospholipids, cationic, anionic or neutral surfactants.

In some embodiments, the subject is suffering from postoperative pain from a surgical site. In some other embodiments, the subject is suffering from arthritis. In still some other embodiments, the subject is suffering from pain from an injury. The instant zinc meloxicam complex microparticle MVL or non-MVL zinc meloxicam complex microparticle formulations can be administered by injection, e.g., subcutaneous injection, intraarticular injection, intramuscular injection, intradermal injection and the like. The instant zinc meloxicam complex microparticles MVL or non-MVL zinc meloxicam complex microparticle formulations can be administered by parenteral injection. In any of the embodiments, these formulations can be administered by bolus injection, e.g., subcutaneous bolus injection, intraarticular bolus injection, intramuscular bolus injection, intradermal bolus injection and the like. In some other embodiments, administration can be by infiltration, e.g., local infiltration at the postsurgical sites, and the like, such as wound instillation or infusion, or simply instilling into an open wound. The aforementioned formulations can also be administered by other routes of administration to treat local inflammation or pain including, but not limited to, topical, ocular, intraocular, nasal, intrathecal, brain, otic, intraperitoneal, or delivery into a body cavity. Non-MVL formulations, such as surfactant-stabilized formulations, can be administered intravenously or by infusion.

In some embodiments, the dose of MLX in the zinc meloxicam complex microparticle MVL or non-MVL zinc meloxicam complex microparticle formulations is about 5 mg to about 20 mg, for example, about 7.5 mg to about 17.5 mg, or about 10 mg to about 15 mg per day.

In some embodiments, the dose of MLX is about 0.01, 0.05, 0.10, 0.15, 0.20, 0.25, 0.30, 0.35, 0.40, 0.45, 0.5, 0.55, 0.60, 0.65, 0.70, 0.75, 0.80, 0.85, 0.90, 0.95, or 1.00 mg/kg per day, or a range defined by any of the two preceding values. In some further embodiments, the dose of MLX is from about 0.05 mg/kg to about 0.30 mg/kg, or from 0.10 mg/kg to about 0.25 mg/kg.

Administration of the instant zinc meloxicam complex microparticle MVL or non-MVL zinc meloxicam complex microparticle formulations is accomplished using standard methods and devices, e.g., pens, injector systems, needle and syringe, a subcutaneous injection port delivery system, and the like. See, e.g., Hall et al., U.S. Pat. No. 3,547,119, issued Dec. 15, 1970; Konopka et al., U.S. Pat. No. 4,755,173, issued Jul. 5, 1988; Yates, U.S. Pat. No. 4,531,937, issued Jul. 30, 1985; Gerard, U.S. Pat. No. 4,311,137, issued Jan. 19, 1982; and Fischell et al., U.S. Pat. No. 6,017,328 issued Jan. 25, 2000, each of which is herein incorporated by reference in their entirety.

In preferred embodiments, the zinc meloxicam complex microparticle MVL formulations or non-MVL zinc meloxicam complex microparticle formulations are administered intraocularly, intrathecally, subcutaneously, intramuscularly, or intraarticularly. Such administration can occur at about 1 to about 7 day intervals at a dose of from about 7.5 mg to about 200 mg for systemic use, and about 0.1 mg to about 10 mg for intraarticular use. Exact dosages will vary depending on patient factors such as age, sex, general condition, and the like. Those of skill in the art can readily take these factors into account and use them to establish effective therapeutic concentrations without resort to undue experimentation.

For systemic administration, the amount of MLX administered per day is preferably between about 7.5 mg and about 15 mg.

For intraarticular administration, the amount of MLX administered per dose will be significantly lower than for subcutaneous administration. For instance, the amount of MLX administered per day is preferably between about 0.075 mg and about 0.15 mg.

For administration by infiltration or instillation, the amount of MLX administered is preferably between about 0.1 mg and about 50 mg.

In some embodiments, the zinc meloxicam complex microparticle MVL or non-MVL zinc meloxicam complex microparticle formulations optionally include a pharmaceutically acceptable carrier. Effective injectable compositions containing the Zn-MLX liposomal particles such as MVLs, unilamellar liposomes and multilamellar vesicles may be in suspension form. A non-MVL sustained release formulation of zinc meloxicam complex microparticles may also be in suspension form for injection.

Injectable suspension compositions containing the instant formulations require a liquid suspending medium, with or without adjuvants, as a vehicle. The suspending medium can be, for example, aqueous solutions of sodium chloride, sucrose, polyvinylpyrrolidone, polyethylene glycol, or combinations of the above. The suspending medium can further include one or more surfactants.

Suitable physiologically acceptable adjuvants may be added to the suspension compositions. The adjuvants may be chosen from among thickeners such as carboxymethylcellulose, polyvinylpyrrolidone, gelatin and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

As used herein, the term "subject" includes animals and humans. In a preferred embodiment, the subject is a human.

In some embodiments, the instant zinc meloxicam complex microparticle MVL or non-MVL zinc meloxicam complex microparticle formulations are administered one, two, three, four, or more times per day. The zinc meloxicam complex microparticle MVL or non-MVL zinc meloxicam complex microparticle formulations can also be administered less than once per day or in a single dose, for example once every 2, 3, 4, 5, 6, 7, 8, 9, 10, 11, 12, 13, or 14 days, or every 1, 2, 3, or 4 weeks, or a range defined by any two of the preceding values. In some embodiments, the number of administrations per day is constant (e.g., one time per day). In other embodiments, the number of administrations is variable. The number of administrations may change depending on effectiveness of the dose, observed side effects, desire to titrate up to a desired dose, external factors (e.g., a change in another medication), or the length of time that the dosage form has been administered.

In some embodiments, a formulation provided herein, for example, a formulation comprising zinc meloxicam complex microparticles encapsulated in MVLs, maintains at least about 100 ng/mL, at least about 200 ng/mL, at least about 300 ng/mL, at least about 400 ng/mL, at least about 500 ng/mL, at least about 750 ng/mL, at least about 1000 ng/mL, at least about 2000 ng/mL, at least about 3000 ng/mL, at least about 4000 ng/mL, or at least about 5000 ng/mL plasma meloxicam concentration at 72 hours after administration to a subject. In further embodiments, a formulation provided herein, for example, a formulation comprising zinc meloxicam complex microparticles encapsulated in MVLs, maintains a therapeutic level of meloxicam in plasma, or at the site of action, for at least about 24 hours, at least about 48 hours, at least about 72 hours, at least about 96 hours, at least about 120 hours, at least about 144 hours, or at least about 168 hours following administration to a subject.

In some embodiments, a non-MVL formulation provided herein, for example, a formulation comprising zinc meloxicam complex microparticles encapsulated in unilamellar liposomes, in multilamellar vesicles, or stabilized by one or more surfactants, maintains at least about 100 ng/mL, at least about 200 ng/mL, at least about 300 ng/mL, at least about 400 ng/mL, at least about 500 ng/mL, at least about 750 ng/mL, at least about 1000 ng/mL, at least about 2000 ng/mL, at least about 3000 ng/mL, at least about 4000 ng/mL, or at least about 5000 ng/mL plasma meloxicam concentration at 72 hours after administration to a subject. In further embodiments, a non-MVL formulation provided herein, for example, a formulation comprising zinc meloxicam complex microparticles encapsulated in unilamellar liposomes, in multilamellar vesicles, or stabilized by one or more surfactants, maintains a therapeutic level of meloxicam in plasma, or at the site of action, for at least about 24 hours, at least about 48 hours, at least about 72 hours, at least about 96 hours, at least about 120 hours, at least about 144 hours, or at least about 168 hours following administration to a subject.

EXAMPLES

While certain therapeutic agents, compositions, formulations and methods of the present invention have been described with specificity in accordance with certain embodiments, the following examples serve only to illustrate the compositions and methods of the invention and are not intended to limit the same.

Example 1. Manufacturing Process of DepoMLX

DepoMLX is composed of multivesicular liposomal (MVL) particles that encapsulate zinc-meloxicam complex microparticles. The DepoMLX product was manufactured by a continuous process composed of processing steps that include the production of a first emulsion (water-in-oil emulsion), a second emulsion (water-in-oil-in-water), solvent removal, diafiltration, and concentration to final potency. Each step was performed under an aseptic condition. The composition for each step is summarized in Table 1 and Table 2. The general process is described in U.S. Pub. No. 2011/0250264, which is hereby incorporated by reference in its entirety.

Preparation of First Aqueous Suspension Containing MLX:

As noted above, the aqueous form of meloxicam readily diffuses across lipid membranes. Therefore, achieving high encapsulation of the meloxicam within the MVL particles was not possible. This challenge was overcome by precipitating meloxicam with a zinc chloride solution to form a zinc-meloxicam complex which has a low solubility in lipids and in aqueous solution. The neutral form of meloxicam establishes equilibrium inside and outside of the MVL particles. Due to the low concentration of solubilized meloxicam inside the particle, the amount of solubilized meloxicam outside of the particles is also low in concentration. An aqueous solution of MLX was prepared with lysine, tartaric acid, and sucrose, in amounts as shown in Table 1A. An equal volume of buffered MLX aqueous solution was mixed with a buffered aqueous solution of zinc chloride containing histidine, tartaric acid and sucrose in Formulation 1 ("1:1 process") and a 2:1 solution volume ratio of meloxicam solution to zinc chloride solution was used for Formulations 2 and 3 ("2:1 process"). The conditions for Formulations 1 to 3 are summarized in Table 1A. Each mixture resulted in the formation of a zinc meloxicam complex $Zn(MLX)_2$ in the form of suspended microparticles. Each mixture was titrated from pH of about 6.6 to a target pH of 5.8 and allowed to settle, and the composition of each post-reaction zinc meloxicam complex microparticle suspension is summarized in Table 1B. The $Zn(MLX)_2$ microparticles suspension was further concentrated by decanting to obtain a desired concentration of meloxicam of about 12 mg/mL, about 15 mg/mL, and about 9.5 mg/mL for Formulations 1, 2, and 3, respectively. The resulting compositions of the first aqueous suspensions of Formulations 1 and 3 is provided in Table 1C (after decantation and pH adjustment). Zinc meloxicam microparticle suspensions may be administered as is, or with addition of, for example, a buffer and/or surfactant, and/or after suspension medium exchange.

Preparation of the First Emulsion:

For each of Formulations 1 to 3, a lipid combination solution containing DEPC, DPPG, tricaprylin and cholesterol in organic solvent (chloroform for Formulations 1 and 2, and methylene chloride for Formulation 3) was mixed with the aqueous suspension containing the zinc-meloxicam suspension to produce a uniform emulsion of water-in-oil (w/o) droplets stabilized by a phospholipid monolayer composed of DEPC and DPPG as summarized in Table 2. For Formulation 3, the first emulsion was formed from approximately 20 L of each of the aqueous suspension and the lipid/organic phase.

Preparation of the Second Emulsion:

For Formulations 1 and 2, the first emulsion was mixed with a second aqueous phase containing sorbitol/histidine/tartaric acid using a three fluid spray nozzle to produce the second water-in-oil-in-water (w/o/w) emulsion in a continuous flow process. The second emulsion was dispersed into droplets in the spray chamber as a result of the nitrogen exiting the nozzle. Within the spray chamber or vessel, humidified nitrogen was introduced to reduce the amount of chloroform in the second emulsion droplets. The reduction of chloroform concentration allows the lipid molecules to self-assemble into the membrane structure of the MVL particles. The surfaces of the solvent removal chamber was rinsed with a continuous spray of rinse solution to facilitate the flow of the MVL particles to the bottom of the solvent removal vessel, and to help control the pH and osmolality of the MVL suspension collected from the exit orifice of the bottom of the solvent removal vessel.

For Formulation 3, the first emulsion was mixed in a batch process with a second aqueous phase containing sorbitol/histidine/tartaric acid/EDTA under stirring to produce the second water-in-oil-in-water (w/o/w) emulsion. The second emulsion was sparged with nitrogen to evaporate methylene chloride solvent, during which MVL particles formed.

Diafiltration:

For Formulations 1 and 2, the formed MVL suspension was subjected to tangential cross-flow filtration to afford a diluted suspension of stable MVL particles containing encapsulated meloxicam in a suspending solution. The system was first subject to a tangential crossflow filtration to obtain a target packed particle volume (PPV) value of the suspension. Then, it was subjected to diafiltration to replace the suspending solution with a saline solution containing histidine and tartaric acid, removing any unencapsulated MLX, residual chloroform, and sorbitol. Finally, the suspension was concentrated to a target PPV value by decantation.

For Formulation 3, the MVL suspension was subjected to batch diafiltration against a solution of saline/histidine/tartaric acid at a pH of 6. Finally, the suspension was concentrated to a meloxicam concentration value by decantation.

TABLE 1A

Compositions of meloxicam solution and zinc salt solution

| Solution ID | Component | Formulation 1 | Formulations 2 and 3 |
|---|---|---|---|
| Meloxicam Sol'n | Meloxicam, mg/mL | 7.0 | 10.5 |
| | L-Lysine, mM | 200 | 200 |
| | L-Tartaric Acid, mM | 82 | 73 |
| | Sucrose | 29 | 50 |
| | Osmolality, mOsm/kg | ~290 | ~293 |
| | pH | 8.2 | 8.5 |
| Zinc Sol'n | $ZnCl_2$, mM | 20 | 47 |
| | L-Tartaric Acid, mM | 5 | 20 |
| | L-Histidine, mM | 55 | 120 |
| | Sucrose, mM | 181 | 101 |
| | Osmolality, mOsm/kg | ~290 | ~285 |
| | pH | 5.5 | 5.3 |

TABLE 1B

Composition of Zinc meloxicam complex microparticle Suspension after Formation of Zinc Meloxicam Complex

| | Component | Formulation 1 | Formulations 2 and 3 |
|---|---|---|---|
| Zinc Meloxicam Complex Aqueous | Meloxicam, mg/mL as in $Zn(MLX)_2$ | 3.5 | 7.0 |
| | $Zn^{2+}$, mM as in $Zn(MLX)_2$ | 5.0 | 10 |
| | Residual Zinc Chloride, mM | 5.0 | 5.7 |
| | L-Lysine, mM | 100 | 133 |

TABLE 1B-continued

Composition of Zinc meloxicam complex microparticle Suspension after Formation of Zinc Meloxicam Complex

| | Component | Formulation 1 | Formulations 2 and 3 |
|---|---|---|---|
| Suspension | L-Tartaric Acid, mM | 44~47 | 67 |
| | L-Histidine, mM | 28 | 40 |
| | Sucrose, mM | 105 | 67 |
| | Osmolality, mOsm/kg | ~290 | ~290 |
| | pH | ~6.6 | ~6.6 |

TABLE 1C

Composition of First Aqueous Suspension

| | Component | Formulation 1 | Formulation 3 |
|---|---|---|---|
| First Aqueous Suspension | Meloxicam, mg/mL as in $Zn(MLX)_2$ | 12 | 9.5 |
| | L-Lysine Monohydrate (mg/ml) | 16.4 | 4.6 |
| | Sucrose (mg/ml) | 36.0 | 75.6 |
| | Tartaric Acid (mg/ml) | 6.5 | 2.2 |
| | Zn in ZnMLX (mg/ml) | 1.1 | 0.9 |
| | free zinc (mg/ml) | 0.3 | 0.1 |
| | free chloride (mg/ml) | 0.7 | 0.2 |
| | L-Histidine (mg/ml) | 4.3 | 1.3 |
| | PH | 5.8 ± 0.2 | 5.8 ± 0.2 |

TABLE 2

Compositions of zinc meloxicam complex microparticle MVL Formulations 1, 2, and 3

| Formulation | | Formulation 1 | Formulation 2 | Formulation 3 |
|---|---|---|---|---|
| First Aqueous Suspension MLX Concentration after decantation (mg/mL) | | ~12 | ~15 | ~9.5 |
| Lipid | Tricaprylin (mg/mL) | 18.8 | 18.8 | 18.8 |
| | Cholesterol (mg/mL) | 15.5 | 15.5 | 15.5 |
| | DPPG (mg/mL) | 8.3 | 8.3 | 8.3 |
| | DEPC (mg/mL) | 23.7 | 23.7 | 23.7 |
| Second Aqueous Phase | L-Tartaric Acid (mM) | 4 | 4 | 4 |
| | L-Histidine (mM) | 20 | 20 | 20 |
| | Sorbitol (% w/v) | 4.2 | 4.2 | 4.2 |
| | EDTA (mg/mL) | n/a | n/a | 2.2 |
| Storage Buffer (isotonic) | | 50 mM histidine 5.5mM tartaric acid NaCl | 50 mM histidine 5.5 mM tartaric acid NaCl | n/a |

TABLE 3

Final DepoMLX Particles Analyses

| | Formulation 1 | Formulation 2 | Formulation 3 |
|---|---|---|---|
| MLX concentration (mg/mL) | 2.4 | 3.1 | 2.4 |
| % free MLX (soluble form) | 1.8 | 1.1 | 1.8 |
| Unencapsulated Zinc MLX salt (%) | 25 | 5 | — |
| PPV (%) | 51 | 50 | 53 |
| Cholesterol (mg/mL) | 6.6 | 5.4 | 5.4 |
| DEPC (mg/mL) | 10.2 | 8.9 | 7.7 |
| DPPG (mg/mL) | 3.0 | 2.6 | 2.8 |
| Tricaprylin (mg/mL) | 8.3 | 6.9 | 6.4 |
| Osmolality (mOsm/kg) | 298 | 280 | 293 |

TABLE 3-continued

Final DepoMLX Particles Analyses

| | | Formulation 1 | Formulation 2 | Formulation 3 |
|---|---|---|---|---|
| External pH | | 6.1 | 6.1 | 6.1 |
| Particle Size Distribution (PSD) in μm | d10 | 10.2 | 9.2 | 11.0 |
| | d50 | 24.8 | 23.2 | 18.7 |
| | d90 | 48.0 | 49.5 | 30.0 |

Example 2. Optimization of First Aqueous Suspension

Zinc meloxicam complex $Zn(MLX)_2$ was formed as a microparticle suspension during the first aqueous preparation whereby a buffered MLX solution and buffered $ZnCl_2$ solution were prepared according to the description in Example 1 and sterile filtered into the first aqueous vessel. The solutions were mixed to aid in $Zn(MLX)_2$ microparticle formation. The mixer was turned off and the formed microparticles were allowed to settle. A decanting step was performed to remove supernatant to achieve the target first aqueous suspension volume with a pH of about 6.6. Titration of the first aqueous was then performed with 1M Tartaric acid to achieve a pH about 5.8. The suspension was fed directly into the emulsification system during the continuous manufacturing process.

Initially, the first aqueous suspension was made with a 1 to 1 volume ratio of MLX solution and zinc chloride solution. The final MLX concentration after the decant step was 12 mg/mL. This concentration was utilized to manufacture the toxicology study material (Formulation 1 in Example 1). The procedure was optimized further to allow for a larger volume of first aqueous to be made within the first aqueous preparation vessel and to achieve a higher MLX concentration in the first aqueous suspension. A 2-to-1 volume of MLX solution to zinc chloride solution as described in Example 1 was mixed, titrated and then settled and decanted. This resulted in a MLX concentration of about 15 mg/mL (Formulation 2 in Example 1). The equivalency of the zinc meloxicam complex at about 12 mg/mL and about 15 mg/mL was confirmed by performing PK studies, whereby the MLX release profile was identical for the two complex microparticle preparations.

In some instances, the formed zinc meloxicam complex microparticle encapsulated MVLs suspension was exposed to a low pH histidine buffer during the diafiltration process.

Example 3. Comparison of Various Meloxicam Metal Complexes

Various metal salts have been used in the preparation of a meloxicam complex microparticles using the 1-to-1 volume of MLX solution to metal divalent cationic salt solution as described in Example 1 (i.e., 1:1 process). 20 mM MLX solution at pH 8.2 was slowly added to 150 mL of 20 mM solution of $ZnCl_2$, $MgCl_2$, or $CuCl_2$ at pH 5.5 and the mixture was allowed to stir at 300 rpm for 3 hours at room temperature. It was observed that precipitate was formed in each solution mixture. The pH of the post-reaction supernatant for the reaction employing $ZnCl_2$, $MgCl_2$, and $CuCl_2$ were pH 6.65, pH 7.73 and pH 6.70 respectively. The precipitate in each reaction was isolated for further analysis and the results are summarized in the table below.

| Cation used | MLX not precipitated (% in Supernatant) | Does precipitate dissolve? | | |
|---|---|---|---|---|
| | | Isopropanol[1] | Chloroform[2] | Dichloromethane[2] |
| Zinc (II) | 2% | no | no | no |
| Magnesium (II) | 71% | yes | yes | yes |
| Copper(II) | 17% | yes | yes | yes |

[1]Dissolution in isopropanol confirmed through % transmission of light through sample on Laser Light Scattering Particle Sizer (LA-950)
[2]dissolution in chloroform and dichloromethane through a) visual observation (or disappearance) of precipitate within solvent; b) tinting of solvent phase When $ZnCl_2$ was used, only 2% free meloxicam was detected in the supernatant, as compared to 71% for $MgCl_2$ and 17% for $CuCl_2$. Therefore, $Zn^{2+}$ produced the highest yield of metal meloxicam complex.

The solubility of the isolated precipitates was tested in isopropanol, chloroform and dichloromethane. In isopropanol, dissolution was confirmed by the presence/disappearance of microcrystals under a microscope and by passing a green laser light through samples in glass vials to observe for microcrystal presence. Dissolution in chloroform and dichloromethane was confirmed through a) visual observation (or disappearance) of precipitate within solvent; b) tinting of solvent phase. In each of the three solvents, no dissolution of the zinc meloxicam complex microparticles was observed. In particular, zinc meloxicam complex microparticles were essentially insoluble in 100% isopropanol even at a large dilution (i.e. 300-fold). In contrast, the magnesium meloxicam or copper meloxicam complexes dissolved either partially or completely in the three test solvents. The solubility property of zinc meloxicam complex microparticles is unexpected because it does not substantially dissolve in either aqueous solution or organic solvents. It also provides superior advantage preparing MVLs by encapsulating zinc meloxicam complex microparticles because such complex will not dissolve in the lipid phase or the solvents used in the preparation of the MVLS, thereby causing the immediate release of meloxicam.

$CaCl_2$ solution was also attempted but it was not compatible with the method described as the buffered $CaCl_2$ solution formed precipitates before contacting the MLX solution.

The optical micrograph of the various metal meloxicam complex microcrystals were obtained with the addition of Duke Standards Microsphere Size Standards (NIST Traceable Mean Diameter) polystyrene microspheres with certified mean diameter 1.030 μm±0.011 μm. The zinc meloxicam complex is in the form of microparticles with the average particle size ranging between below 1 micron and 2 microns. In contrast, the particle size of the magnesium meloxicam complex ranges from about 8 micron to about 40 micron and the average maximum particle size is about 29 micron. The particle size of the copper meloxicam complex ranges from about 7 micron to about 15 micron and the average maximum particle size is about 14 micron. As such, neither $MgCl_2$ nor $CuCl_2$ was able to form the corresponding meloxicam complex in the form of microparticles. This evidence further demonstrates the uniqueness of the zinc (II) cation. The chambers within MVLs are about 1-3 μm in size, and thus only the zinc meloxicam complex microparticles were of the appropriate size range for encapsulation in MVLs.

Example 4. Comparative Pharmacokinetic Studies in Rats

In this example, several comparative pharmacokinetic studies were conducted to compare the bioavailability of meloxicam in various formulations. In each of the studies, a single 1.5 mg dose of a meloxicam formulation was subcutaneously injected into 3-6 rats.

Figure 6:
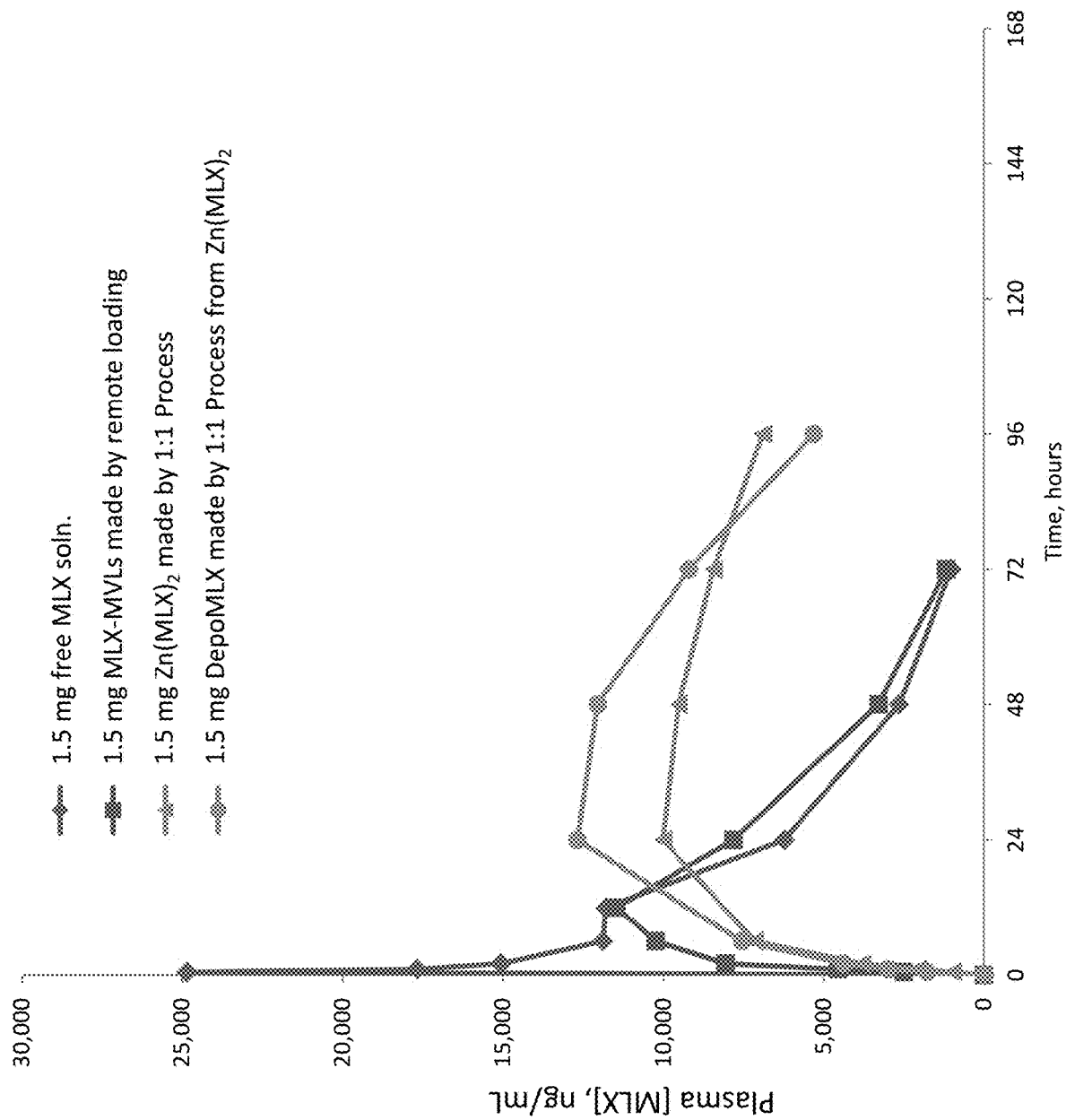
FIG. 6 illustrates the plasma meloxicam concentration of free MLX solution, the multivesicular liposome encapsulating MLX by a remoting loading method, DepoMLX encapsulating $Zn(MLX)_2$ and unencapsulated $Zn(MLX)_2$.

FIG. 6 compares the plasma meloxicam concentration of a free MLX solution (i.e., immediate release formulation), with three controlled release formulations of meloxicam including (a) multivesicular liposomes encapsulating MLX by a remoting loading method, (b) DepoMLX encapsulating $Zn(MLX)_2$ and (c) an unencapsulated $Zn(MLX)_2$ suspension. The multivesicular liposome formulation of MLX prepared by the remote loading method was prepared as follows: meloxicam was remote-loaded into the blank MVLs by incubating a pH-adjusted MLX solution with the blank MVL particle suspension under gentle agitation. To improve encapsulation, 10 mM $CaCl_2$ solution and 12.5% cyclodextrin were also added to the internal aqueous solution of the blank MVL particles. After meloxicam had partitioned into the blank MVLs using a pH gradient, the suspensions were washed in normal saline to remove unencapsulated or free meloxicam. The $Zn(MLX)_2$ suspension was prepared by the 2-to-1 volume of MLX solution to zinc chloride solution process as described in Example 1 (i.e., the 2:1 process) and was also used in the preparation of DepoMLX encapsulating $Zn(MLX)_2$.

It was observed that each of formulations (a), (b) and (c) provided better bioavailability and longer duration of drug potency compared to the immediate release formulation. Although $Ca^{2+}$ can also forms a metal complex with meloxicam, the multivesicular liposomes encapsulating zinc meloxicam complex microparticles demonstrated much superior sustained release properties compared to the meloxicam encapsulated multivesicular liposomes prepared by the remote loading method. In addition, it was unexpectedly discovered that when the $Zn(MLX)_2$ microparticle suspension that was unencapsulated, provided a better release profile than the MVL formulation obtained through a remote loading method.

Figure 7:
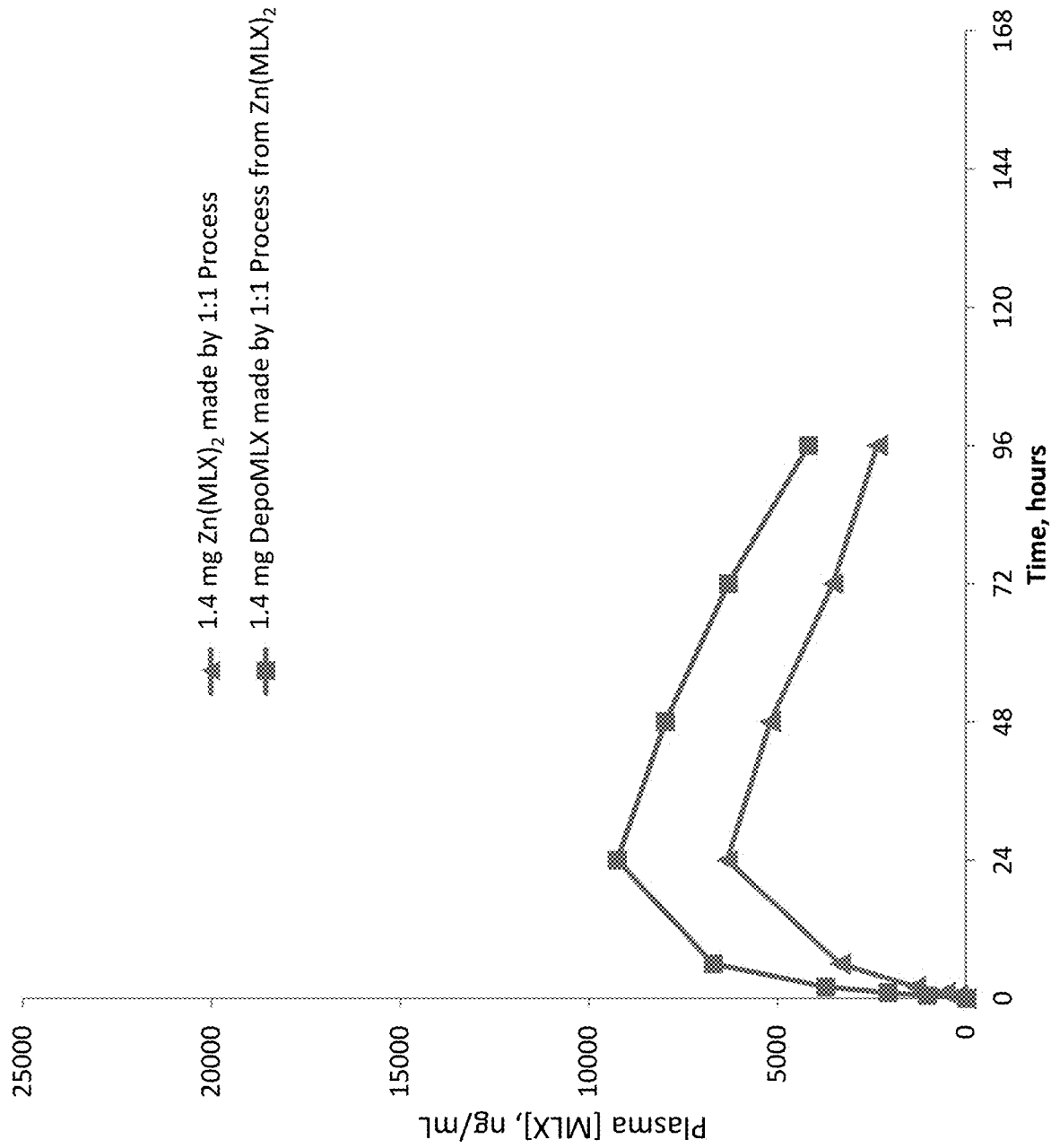
FIG. 7 illustrates the plasma meloxicam concentration of unencapsulated $Zn(MLX)_2$ suspension and the corresponding encapsulated $Zn(MLX)_2$ as DepoMLX.

FIG. 7 compares the plasma meloxicam concentration of 1.4 mg dose of an unencapsulated $Zn(MLX)_2$ suspension and 1.4 mg dose of the corresponding encapsulated $Zn(MLX)_2$ as DepoMLX where the zinc meloxicam complex microparticles were prepared by 1-to-1 volume of MLX solution to zinc chloride solution as described in Example 1 (i.e., 1:1 process). The DepoMLX formulation provided better plasma Cmax and AUC of meloxicam compared to the unencapsulated $Zn(MLX)_2$.

Figure 8:
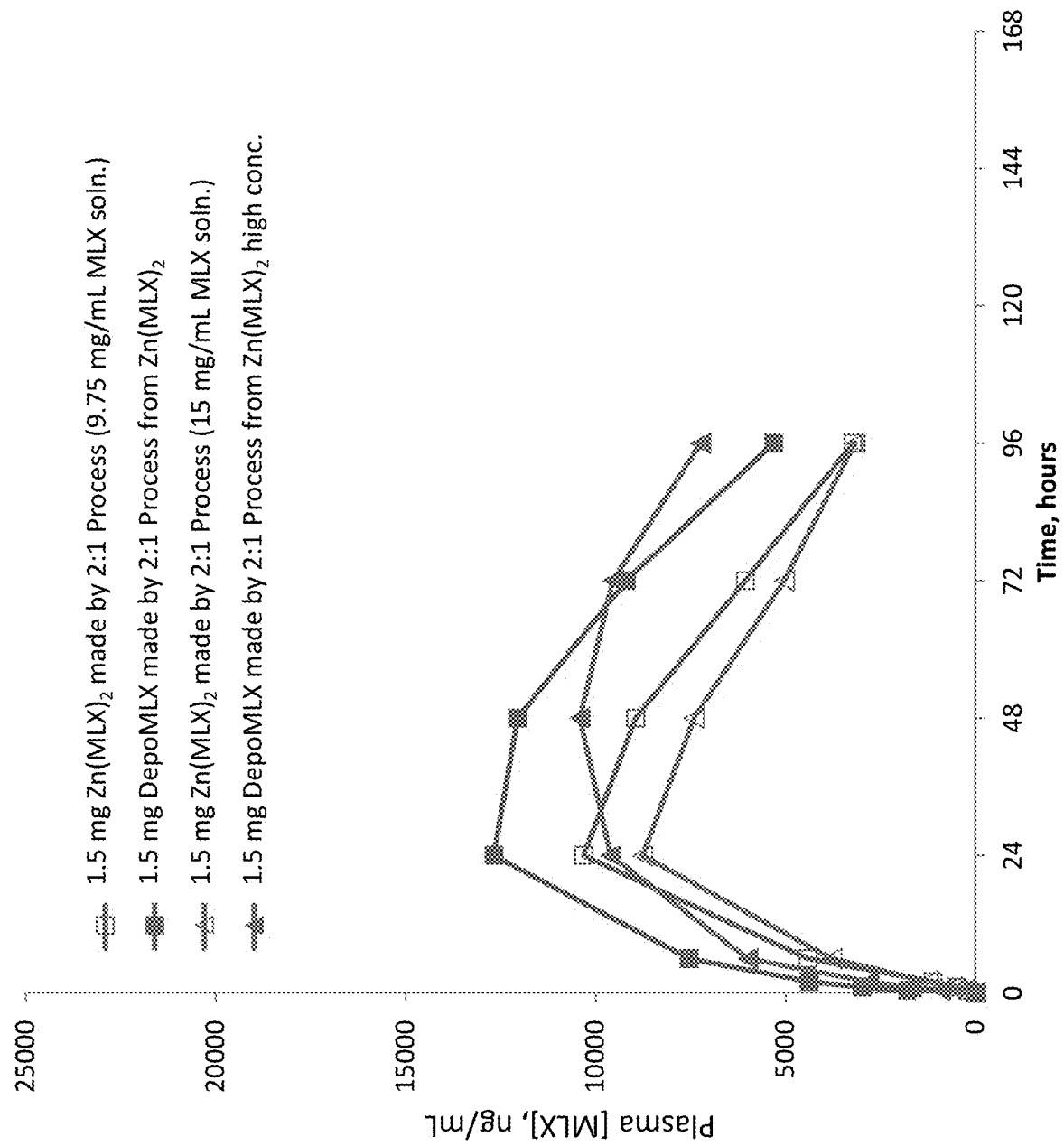
FIG. 8 illustrates the plasma meloxicam concentration of unencapsulated $Zn(MLX)_2$ suspension prepared from two different concentrations of MLX solution and the corresponding encapsulated $Zn(MLX)_2$ as DepoMLX.

FIG. 8 compares the plasma meloxicam concentration of unencapsulated $Zn(MLX)_2$ suspension prepared from the 2:1 process using two different concentrations of meloxicam (9.75 mg/mL and 15 mg/mL respectively) and DepoMLX encapsulating $Zn(MLX)_2$ with a dose of 1.5 mg meloxicam in each formulation. It was observed that the DepoMLX encapsulating $Zn(MLX)_2$ prepared from the high concentration of meloxicam solution provided the best sustained release properties. Both DepoMLX formulations had improved bioavailability and plasma concentrations at 96 hours, indicating a longer duration of effect.

Example 5. Toxicological Studies in Rats

A single-dose subcutaneous toxicity pilot study was conducted in male rats to evaluate the local tolerance and toxicity of DepoMLX formulations. Groups of 10 male Sprague-Dawley rats were subcutaneously injected with meloxicam (reference), unencapsulated zinc meloxicam complex microparticles with the formula $Zn(MLX)_2$, or DepoMLX at equivalent doses of 2 mg/kg. Mortality checks, clinical signs, and body weights were monitored. The rats were euthanized on Days 4 (N=5) and 18 (N=5) post injection and examined macroscopically and microscopically. No clinical signs related to the administration of MLX, $Zn(MLX)_2$, or DepoMLX were observed, with no apparent effect on body weight.

At necropsy, there were no gross changes upon macroscopic examination of tissues. Upon microscopic examination on Day 4, post injection, animals administered MLX or unencapsulated zinc meloxicam complex microparticles with the formula $Zn(MLX)_2$ had mixed cell inflammation (minimal to mild) at the injection sites as well as minimal to mild necrosis ($Zn(MLX)_2$ only), due to local irritation by meloxicam. This was fully reversed by Day 18.

In animals administered DepoMLX and terminated on Day 4 post injection, granulomatous inflammation, primarily composed of sheets of macrophages containing foamy cytoplasmic material that was consistent with lipid was noted at the injection sites. This was considered likely due to the lipid-based MVL component of the formulation, which requires macrophages for clearance. In rats terminated on Day 18 following a 17-day post-dose observation period, minimal to mild mixed cell inflammation only was noted at the injection sites, suggesting an ongoing reversal of the earlier granulomatous changes.

In view of the above, administration of a single subcutaneous injection of either reference MLX or unencapsulated zinc meloxicam complex microparticles with the formula $Zn(MLX)_2$ in male rats produced evidence of discomfort upon injection. Any inflammatory changes were either fully or partially reversed over the 17-day post-dose observation period.

Figure 9:
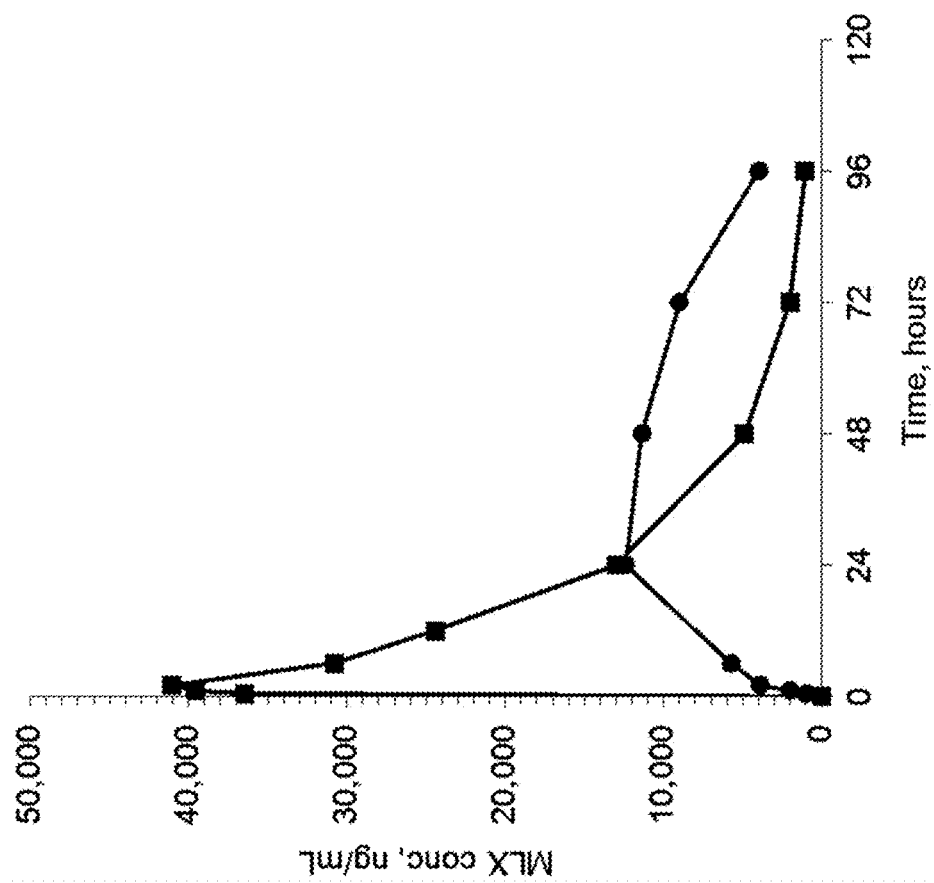
FIG. 9 illustrates the plasma meloxicam concentration as a function of time of DepoMLX (circles—●) versus unencapsulated meloxicam (squares—■) following a single subcutaneous injection in rats.
Figure 10:
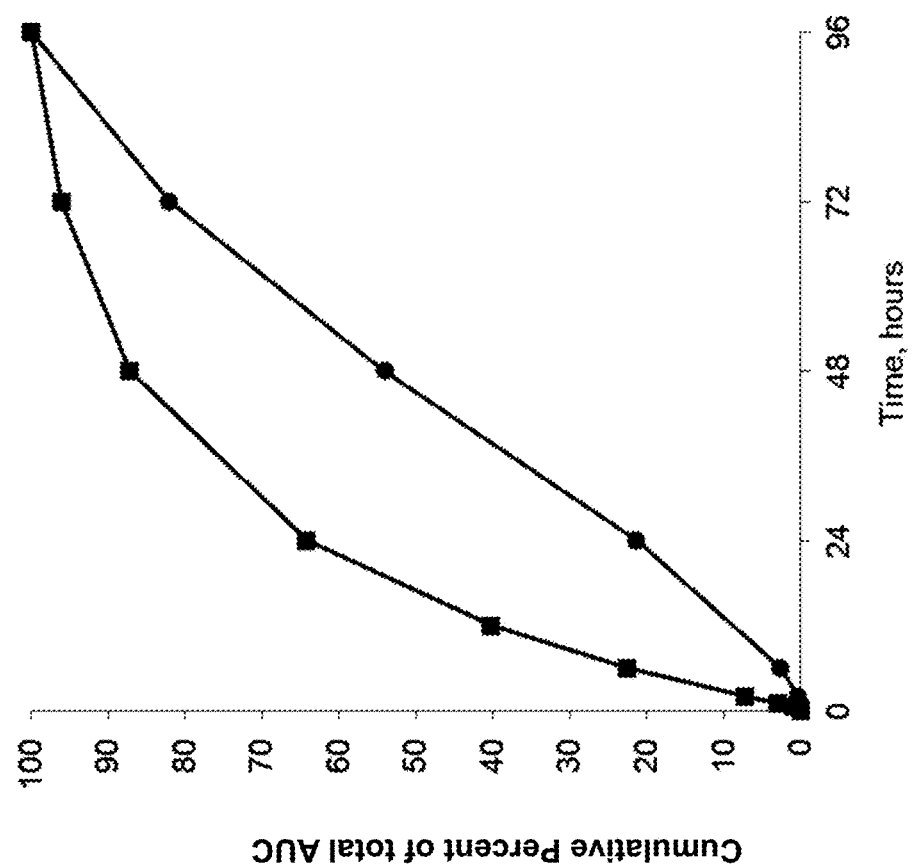
FIG. 10 illustrates the cumulative percent of total AUC of meloxicam in plasma as a function of time following the administration of DepoMLX (circles—●) versus unencapsulated MLX (squares—■) following a single subcutaneous injection in rats.

In addition, the pharmacokinetics of the DepoMLX was evaluated and compared to free MLX. The results are summarized in FIG. 9 and FIG. 10. FIG. 9 compares the duration of unencapsulated MLX vs DepoMLX following subcutaneous injection in rats. FIG. 10 compares the time distribution of accumulative percent of total AUC of plasma MLX following subcutaneous injection of DepoMLX vs unencapsulated MLX. The unencapsulated MLX PK curve is first order, and almost 87% of the MLX has been delivered after only 2 days. In contrast, the DepoMLX PK curve is nearly linear, and the MLX was delivered over a period of at least 4 days.

Example 6. Toxicokinetics (TK) Studies in Dogs by Subcutaneous Injection

The TK characteristics of repeated-dose subcutaneous (SC) injections of DepoMLX were determined and compared with reference MLX (Metacam® for injection diluted with saline) as a component of the 4-week, repeat-dose, subcutaneous toxicology study in beagle dogs. The dogs (n=5/sex/groups) were given once weekly, subcutaneous doses of saline control, DepoMLX at 0.2, 0.6, or 1 mg/kg/week, or an equivalent high dose of reference MLX at 1 mg/kg/week. Blood samples were collected up to 72 hours after dosing for determination of plasma concentrations of MLX on study Day 1 and after the last dose on Day 22. TK sampling was extended up to 240 hours post dosing on Day 22 for the recovery animals. Plasma samples were analyzed for levels of MLX using a validated, GLP-compliant LC-MS/MS assay. For DepoMLX- and MLX-treated animals, plots of plasma concentration versus time and resulting kinetics for males and females demonstrated no gender differences. Thus, mean TK parameter estimates for the combined genders were used.

Mean toxicokinetic parameters are shown in Table 4 for day 1 following administration and in Table 5 for 22 days following administration. TK analysis clearly demonstrated that following subcutaneous injection, high levels of MLX contained in the DepoMLX dosing material were absorbed into the peripheral circulation. For both DepoMLX and reference MLX, there was no significant difference between genders. Plasma exposures (Cmax and area under the curve [AUC]) were equivalent on Days 1 and 22 confirming the absence of accumulation. For DepoMLX on both Day 1 and Day 22, the increase in AUC was dose proportional. MLX plasma concentrations in recovery animals showed a longer exposure time for the 1.0 mg/kg/week DepoMLX group compared to the 1.0 mg/kg/week MLX group.

Comparing mean exposures between the 1.0 mg/kg DepoMLX group and the 1.0 mg/kg reference free MLX group, mean peak (Cmax) exposures were 1.5- to 1.6-fold higher for the free MLX group after a single dose (Day 1) or multiple doses (Day 22). Mean overall systemic exposures ($AUC_{0-72}$) were also slightly greater for the free MLX group. However, both half-life and mean residence time (MRT) were markedly greater for the 1.0 mg/kg DepoMLX group versus the 1.0 mg/kg free MLX group, with MRT being approximately 1.5 times greater for DepoMLX (51.0 versus 30.3 hours on Day 22).

TABLE 4

Plasma toxicokinetic parameters on Day 1 following subcutaneous administration of MLX and DepoMLX in dogs

| Parameter | MLX 1 mg/kg | DepoMLX 0.2 mg/kg | DepoMLX 0.6 mg/kg | DepoMLX 1 mg/kg |
|---|---|---|---|---|
| $T_{max}$ (hr) | 7.6 | 40.8 | 44.4 | 43.2 |
| $C_{max}$ (ng/mL) | 2451 | 311 | 895 | 1648 |
| $C_{max}/D$ (kg * ng/mL/mg) | 2451 | 1554 | 1492 | 1648 |
| $AUC_{0-24}$ (ng * hr/mL) | 46564 | 3192 | 9071 | 15980 |
| $AUC_{0-48}$ (ng * hr/mL) | 74725 | 9575 | 28196 | 52562 |
| $AUC_{0-72}$ (ng * hr/mL) | 88851 | 15448 | 46136 | 83270 |
| $AUC_{0-72}/D$ (hr * kg * ng /mL/mg) | 88851 | 77240 | 76893 | 83272 |
| $AUC_{0-inf}$ (ng * hr/mL) | 103794 | $NR^a$ | NR | NR |

TABLE 4-continued

Plasma toxicokinetic parameters on Day 1 following subcutaneous administration of MLX and DepoMLX in dogs

| Parameter | MLX 1 mg/kg | DepoMLX 0.2 mg/kg | DepoMLX 0.6 mg/kg | DepoMLX 1 mg/kg |
|---|---|---|---|---|
| $T_{1/2elim}$ (hr) | 24.7 | 61.7 | NR | 44.6 |
| MRT (hr) | 26.5 | 41.0 | 41.5 | 41.4 |

$NR^a$ = not reported. For $AUC_{0-inf}$ the data were not reported if values for % extrap were >25%. For $T_{1/2}$, data were not reported if regression values for the terminal phase were <0.90.

TABLE 5

Plasma toxicokinetic parameters on Day 22 following subcutaneous administration of MLX and DepoMLX in dogs

| Parameter | MLX 1 mg/kg | DepoMLX 0.2 mg/kg | DepoMLX 0.6 mg/kg | DepoMLX 1 mg/kg |
|---|---|---|---|---|
| $T_{max}$ (hr) | 4.8 | 42.0 | 48.0 | 39.6 |
| $C_{max}$ (ng/mL) | 2.743 | 340 | 949 | 1757 |
| $C_{max}$/D (kg * ng/mL/mg) | 2.743 | 1670 | 1582 | 1757 |
| $AUC_{0-24}$ (ng * hr/mL) | 52573 | 4030 | 11487 | 18485 |
| $AUC_{0-48}$ (ng * hr/mL) | 81649 | 11152 | 31877 | 56326 |
| $AUC_{0-72}$ (ng * hr/mL) | 108217 | 18409 | 49403 | 89084 |
| $AUC_{0-72}$/D (hr * kg * ng /mL/mg) | 108217 | 92045 | 82338 | 89084 |
| $AUC_{0-inf}$ (ng * hr/mL) | 104170 | 22278 | 62914 | 113484 |
| $T_{1/2elim}$ (hr) | 25.4 | 34.2 | 55.6 | 41.2 |
| MRT (hr) | 30.3 | 49.7 | 50.2 | 51.0 |

Example 7. Toxicokinetics (TK) Studies in Dogs by Wound Instillation

A 14-day toxicity study following single surgical wound instillation in beagle dogs were completed. Metacam solution, the reference listed drug for this example, is an oral product but was used in this study as Metacam solution for injection. The TK characteristics of single dose administration of DepoMLX were determined and compared with the reference MLX (reference, Metacam® 0.5% Solution for Injection) as a component of the single dose (hernia repair) wound instillation toxicology study in dogs. In this study, dogs (n=5/sex/groups) were anesthetized and the skin incised to expose the inguinal canal that was instilled over a targeted 1 minute with a single administration of DepoMLX at the doses of 0 (saline), 0.3 or 1.5 mg/kg or with an equivalent dose of the reference MLX at 0.3 mg/kg.

Blood samples were collected for the determination of plasma concentrations of MLX beginning at 0.5 hours post-instillation and extended out for 72 hours for animals scheduled at termination on Day 4. TK bleeds were extended up to 240 hours after dosing for the recovery animals scheduled for termination on Day 14. Plasma samples were analyzed for levels of MLX using a validated, GLP-compliant LC-MS/MS assay.

Results of the TK analysis clearly demonstrated that high levels of the MLX contained in the DepoMLX dosing material were absorbed into peripheral circulation following the dose instillation. There were no marked differences between the genders and for DepoMLX, and the increase in AUC was dose proportional. Mean TK parameters at the end of treatment are shown in Table 6 and Table 7 for male and females respectively. Since main study animals were necropsied after the 72-hour time point and had not yet entered the terminal elimination phase, values for $AUC_{0-last}$, $AUC_{0-inf}$ and mean terminal elimination half-life ($t_{1/2}$) were reported only in recovery animals that were bled up to 240 hours after dosing.

TABLE 6

Mean Plasma Toxicokinetic Parameters on Day 1 Following Surgical Instillation of DepoMLX and Free MLX to Male Dogs (n = 5/gender unless indicated)

| Parameter | Units | DepoMLX 0.3 mg/kg Male | DepoMLX 1.5 mg/kg Male | Free MLX 0.3 mg/kg Male |
|---|---|---|---|---|
| $T_{max}$ | Hr | 18.4 ± 7.8 | 31.0 ± 6.6 | 5.6 ± 3.3 |
| $C_{max}$ | ng/mL | 797 ± 149 | 4554 ± 1467 | 1190 ± 211 |
| $C_{max}$/D | kg * ng/mL/mg | 2657 | 3036 | 3967 |
| $AUC_{0-24}$ | ng * hr/mL | 13924 ± 2203 | 62371 ± 12688 | 23714 ± 4931 |
| $AUC_{0-48}$ | ng * hr/mL | 29281 ± 5607 | 160965 ± 43607 | 37864 ± 9306 |
| $AUC_{0-72}$ | ng * hr/mL | 38959 ± 8263 | 228124 ± 66269 | 46612 ± 12052 |
| $AUC_{0-72}$/D | hr * kg * ng/mL/mg | 129863 | 152083 | 155373 |
| $AUC_{0-inf}$ | ng * hr/mL | 49284 ± 19312$^a$ | 242646 ± 36778$^a$ | 56961 ± 23274$^a$ |
| % extrap | % | 1.1 ± 0.1$^a$ | 0.4 ± 0.3$^a$ | 1.1 ± 0.1$^a$ |
| $AUC_{last}^a$ | ng * hr/mL | 48734 ± 19035$^a$ | 241614 ± 37278$^a$ | 56355 ± 23076$^a$ |
| $T_{1/2}$ | Hr | 26.1 ± 3.21$^a$ | 29.1 ± 4.42$^a$ | 23.0 ± 4.25$^a$ |
| MRT | Hr | 39.1 ± 790 | 45.1 ± 10.6 | 31.2 ± 5.40 |

$^a$TK parameters from N = 2 (Recovery animals only), animals were bled up to 240 hours after dosing to include the terminal elimination phase in the calculation.

TABLE 7

Mean Plasma Toxicokinetic Parameters on Day 1 Following Surgical Instillation of DepoMLX and Free MLX to Female Dogs (n = 5/gender unless indicated)

| Parameter | Units | DepoMLX 0.3 mg/kg Female | DepoMLX 1.5 mg/kg Female | Free MLX 0.3 mg/kg Female |
|---|---|---|---|---|
| $T_{max}$ | Hr | 19.2 ± 6.6 | 26.4 ± 5.5 | 4.00 ± 2.0 |
| $C_{max}$ | ng/mL | 1094 ± 245 | 4720 ± 870 | 1274 ± 159 |
| $C_{max}$/D | kg * ng/mL/mg | 3646 | 3147 | 4247 |
| $AUC_{0-24}$ | ng * hr/mL | 20249 ± 3224 | 70669 ± 9.374 | 23336 ± 4225 |
| $AUC_{0-48}$ | ng * hr/mL | 40021 ± 7163 | 171556 ± 20383 | 37582 ± 8538 |
| $AUC_{0-72}$ | ng * hr/mL | 53433 ± 9824 | 245716 ± 33371 | 45578 ± 11212 |
| $AUC_{0-72}$/D | hr * kg * ng/mL/mg | 178110 | 163811 | 151927 |
| $AUC_{0-inf}$ | ng * hr/mL | 76198 ± 17052$^a$ | 303739 ± 15735$^a$ | 55105 ± 14130 |
| % extrap | % | 0.7 ± 0.2$^a$ | 0.2 ± 0.03$^a$ | 11 ± 10 |

TABLE 7-continued

Mean Plasma Toxicokinetic Parameters on Day 1 Following Surgical Instillation of
DepoMLX and Free MLX to Female Dogs (n = 5/gender unless indicated)

| | | DepoMLX | | Free MLX |
|---|---|---|---|---|
| Parameter | Units | 0.3 mg/kg Female | 1.5 mg/kg Female | 0.3 mg/kg Female |
| $AUC_{last}{}^a$ | ng * hr/mL | 75649 ± 16790$^a$ | 303099 ± 15614$^a$ | 66812 ± 15676$^a$ |
| $T_{1/2}$ | Hr | 28.6 ± 6.26$^a$ | 22.9 ± 3.0$^a$ | 27.9 ± 4.0 |
| MRT | Hr | 40.4 ± 11.2 | 43.3 ± 8.7 | 31.3 ± 7.9 |

$^a$TK parameters from N = 2 (Recovery animals only), animals were bled up to 240 hours after dosing to include the terminal elimination phase in the calculation.

Comparing the 0.3 mg/kg dose level of DepoMLX to the same dose level of free MLX, the time to mean peak exposures ($T_{max}$) were very much delayed by the expected action of the liposomal formulation. Following DepoMLX treatment, $T_{max}$ in males and females was reached at approximately 18-19 hours (range was 8-24 hours with 6 dogs/10 reaching $T_{max}$ at 24 hours) whereas mean $T_{max}$ in free MLX-treated animals was approximately 4-5 hours (range was 2-8 hours).

Mean $C_{max}$ was slightly lower following DepoMLX treatment vs. free MLX treatment. This result was expected given the anticipated action of DepoMLX. Mean $C_{max}$ in DepoMLX-treated males was 33% lower than peak levels in free MLX treated males, and peak levels were 14% lower in females. Mean systemic exposures (AUC) were slightly lower in males and slightly greater in females for the DepoMLX group vs. free MLX. However, the differences in Cmax and AUC between DepoMLX and MLX groups may be attributed to the variability of the data. $AUC_{last}$ is a more representative measure of systemic exposure since it includes the terminal elimination phase in the calculation (DepoMLX groups are not yet in the terminal elimination phase between 24 and 72 hours), and the $AUC_{last}$ for DepoMLX and MLX groups given the same dose are comparable, as expected. Mean values for half-life were equivalent for DepoMLX and free MLX in males (26.1 vs. 23.0 hours) and females (28.6 vs. 27.9 hours) between the two treatments, respectively. When comparing values for MRT between these two groups, DepoMLX had a somewhat longer residence time at 39.1 and 40.4 hours in males and females, respectively, vs. 31.2 and 31.3 hours for the free MLX group (approximately +25% longer).

Example 8. Toxicokinetics (TK) Studies in Dogs by Intraarticular Injection

In this study, the TK characteristics of repeated intra-articular administration of a 2.4 mg/mL DepoMLX solution were determined and compared with the reference free MLX (reference, Metacam® 0.5% Solution for Injection) as a component of the 4 cycle intra-articular toxicology study in dogs. The dogs (n=5/sex/groups) were anesthetized and given twice weekly (on study Days 1, 4, 8 and 12), single intra-articular injection to the right femoro-tibial joint of 0 (saline control), DepoMLX at 1.2 or 2.4 mg (0.5 and 1 mL, respectively) or an equivalent high dose of the reference MLX at 2.4 mg. The dose volume of 1 mL is the maximum feasible volume for the intra-articular space in beagles and the approximate dose by weight for the high doses is therefore 0.24 mg/kg based on a 10 kg beagle weight. Blood samples were collected following Day 1 and Day 12 dose administrations for the determination of plasma concentrations of MLX beginning at 0.5 hours and extending out for 72 hours relative to the Days 1 and 12 dose administrations. Since main study animals were necropsied after the 72-hour time point and had not yet entered the terminal elimination phase, TK bleeds were extended up to 240 hours after dosing on Day 12 for the recovery animals. Plasma samples were analyzed for levels of MLX using a validated, GLP-compliant LC-MS/MS assay.

The plot of plasma concentration vs. time for males and females at 1.2 and 2.4 mg (Groups 2 and 3, respectively) and results of TK analysis demonstrated no gender differences. Following intra-articular injection, high levels of MLX contained in the DepoMLX dosing material were absorbed into the peripheral circulation. Plasma exposures ($C_{max}$ and area under the curve [AUC]) were equivalent on Days 1 and 12 confirming the absence of accumulation. For DepoMLX, both peak and overall systemic exposures increased proportionately when the dose increased from 1.2 to 2.4 mg/dose.

Mean TK parameters at the end of treatment for the combined genders are shown in Table 8. Since Main study animals were necropsied after the 72-hour time point and had not yet entered the terminal elimination phase, values for $AUC_{0-last}$, mean terminal elimination half-life ($t_{1/2}$) and mean residence time (MRT) were also reported in Recovery animals that were bled up to 240 hours after dosing.

TABLE 8

Plasma Toxicokinetic Parameters on Day 12 Following Intraarticular Administration
of MLX or DepoMLX In Beagle Dog (Genders Combined) (Mean (±St. Dev.)
Parameter (n = 10; 5M/5F, unless indicated).

| | | DepoMLX | | Free MLX |
|---|---|---|---|---|
| Parameter | Units | 1.2 mg | 2.4 mg | 2.4 mg |
| $T_{max}$ | hr | 27.2 ± 11 | 26.4 ± 7.6 | 1.75 ± 0.98 |
| $C_{max}$ | ng/mL | 363 ± 114 | 686 ± 160 | 1197 ± 238 |
| $C_{max}/D$ | kg * ng/mL/mg | 302 | 286 | 499 |
| $AUC_{0-24}$ | ng * hr/mL | 6600 ± 2766 | 11724 ± 3406 | 19876 ± 4423 |

TABLE 8-continued

Plasma Toxicokinetic Parameters on Day 12 Following Intraarticular Administration of MLX or DepoMLX In Beagle Dog (Genders Combined) (Mean (±St. Dev.) Parameter (n = 10; 5M/5F, unless indicated).

| | | DepoMLX | | Free MLX |
|---|---|---|---|---|
| Parameter | Units | 1.2 mg | 2.4 mg | 2.4 mg |
| $AUC_{0-48}$ | ng * hr/mL | 13130 ± 3958 | 24952 ± 5389 | 31004 ± 7707 |
| $AUC_{0-72}$ | ng * hr/mL | 17479 ± 4635 | 33522 ± 6402 | 37647 ± 10092 |
| $AUC_{0-72}/D$ | hr * kg * ng/mL/mg | 14566 | 13968 | 15686 |
| $T_{1/2}$ | hr | 41.7 ± 7.6 (n = 9) | 38.1 ± 18 | 34.8 ± 7.5 |
| MRT | hr | 33.3 ± 3.6 | 33.7 ± 2.0 | 26.6 ± 1.9 |
| $AUC0\text{-}last^a$ | ng * hr/mL | 25716 ± 5351 | 50707 ± 8083 | 37526 ± 5363 |
| $T_{1/2}{}^a$ | hr | 29.2 ± 1.6 | 28.2 ± 1.6 | 25.4 ± 1.9 |
| $MRT^a$ | hr | 50.8 ± 6.9 | 52.7 ± 2.8 | 36.5 ± 2.0 |

$^a$TK parameters from N = 2 (Recovery animals only), animals were bled up to 240 hours after dosing to include the terminal elimination phase in the calculation.

The $T_{max}$ was markedly delayed for both DepoMLX groups when compared to the free MLX group. On both Day 1 and Day 12, the mean $T_{max}$ values ranged from 26-29 hours for DepoMLX vs. 2 hours for free MLX, which was a desired effect of the DepoMLX formulation. Comparing mean exposures between the 2.4 mg DepoMLX group and the 2.4 mg free MLX group, mean peak ($C_{max}$) exposures were 1.7- to 1.8-fold higher for the free MLX group after a single dose (Day 1) or multiple doses (Day 12). Mean overall systemic exposures ($AUC_{last}$) were also slightly greater for the free MLX group, but the difference is not significant and is attributed to the variability of the data. Half-life was slightly greater in the DepoMLX-treated animals vs. free MLX when the 0-72 window was used for its estimation, but due to the fact that the Main Study blood sampling period did not fully encompass the terminal phase for the DepoMLX and free MLX groups, it was a poor estimate of actual half-life. On Day 12, although the half-life in Recovery animals was comparable for the DepoMLX and free MLX, the mean residence time was greater by 1.4-fold for the 2.4 mg DepoMLX group vs. the free MLX group (on Day 12 recovery animals, 52.7 vs 36.5 hours).

Example 9. Crystal Data for Encapsulated and Unencapsulated $Zn(MLX)_2$ Complex

Figure 14A:
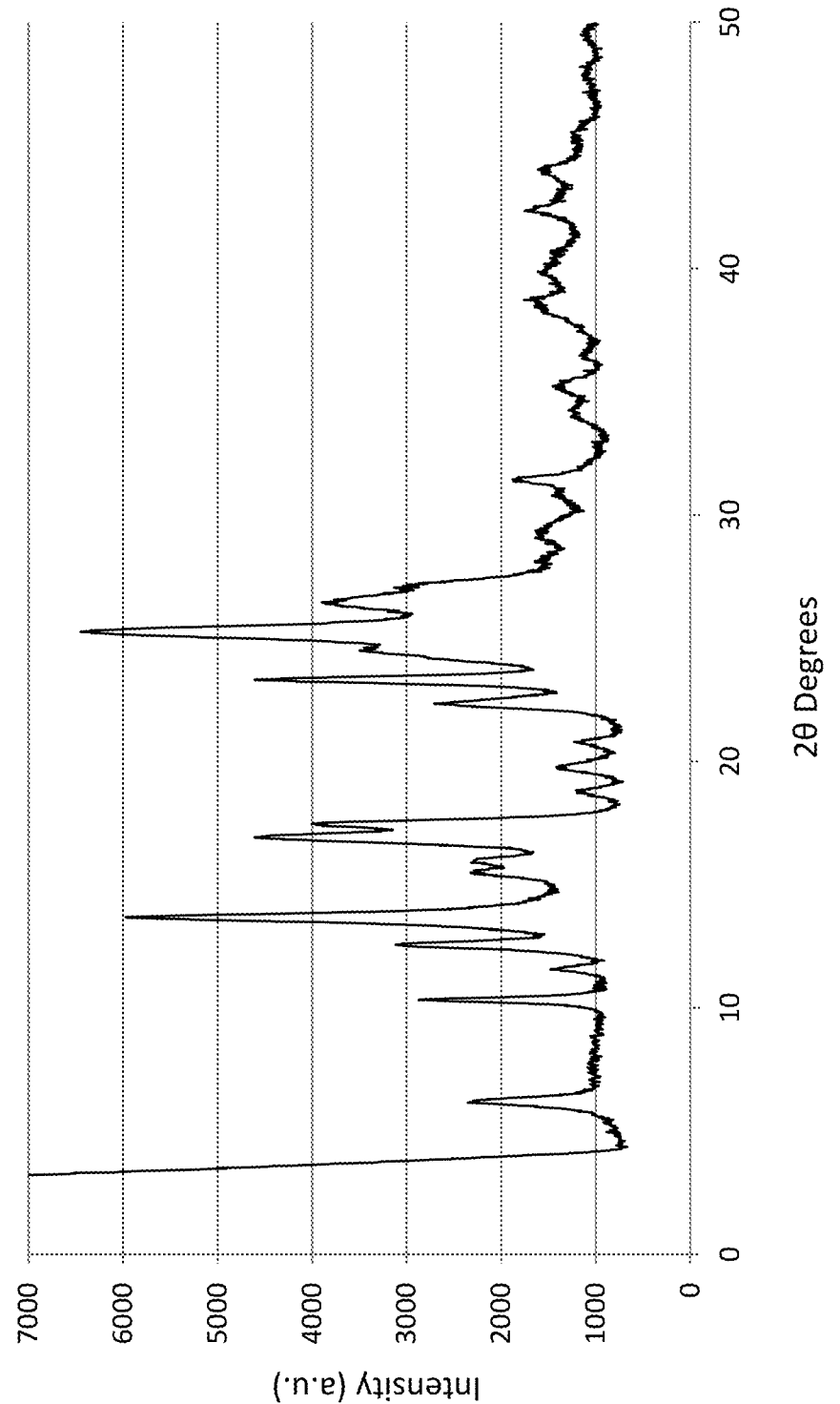
FIG. 14A and FIG. 14B illustrate X-ray powder diffraction (XRPD) spectra for microcrystalline $Zn(MLX)_2$ prepared by a 1:1 process (FIG. 14A) and 2:1 process (FIG. 14B) respectively.
Figure 14B:
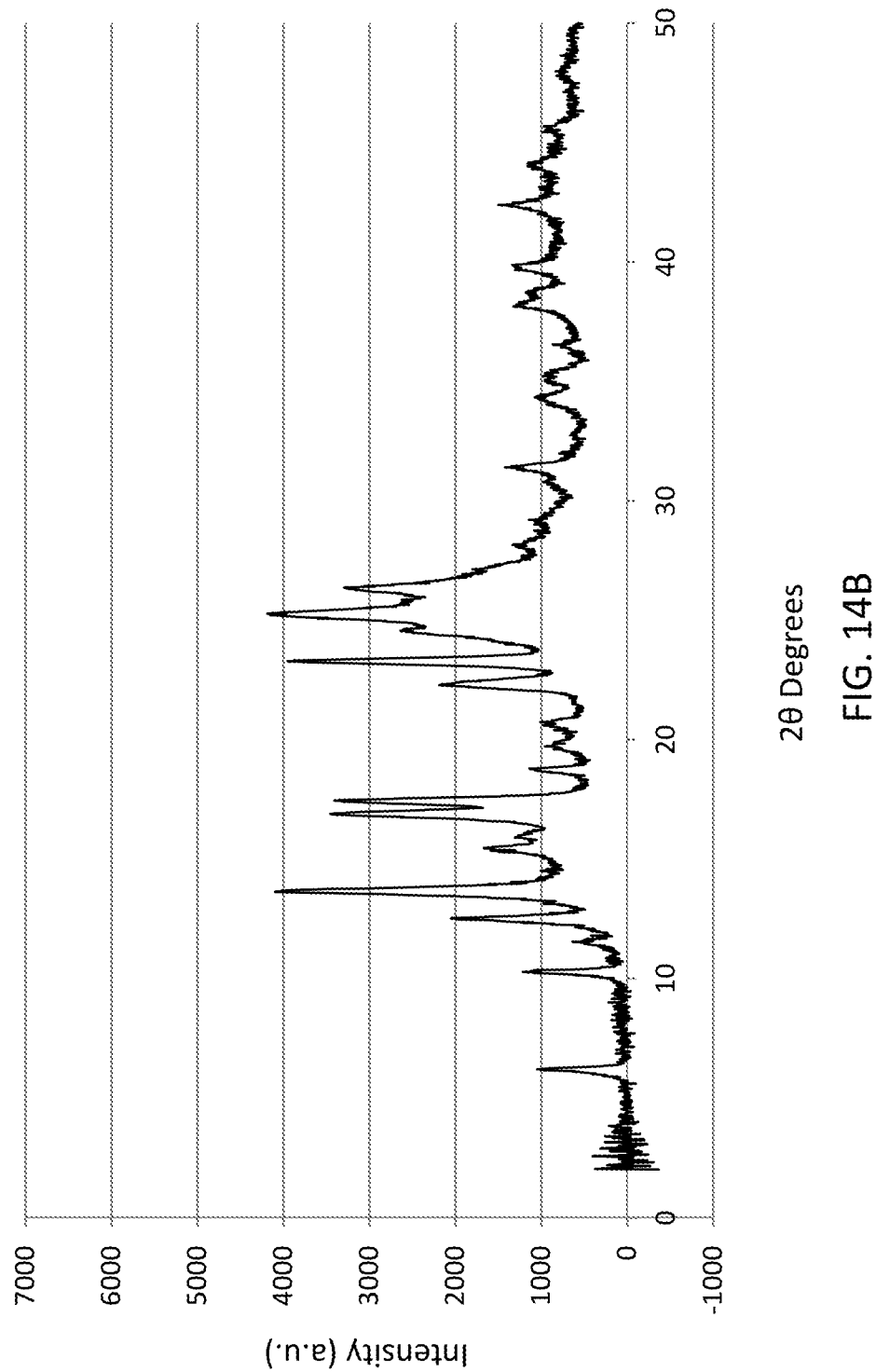
Figure 15:
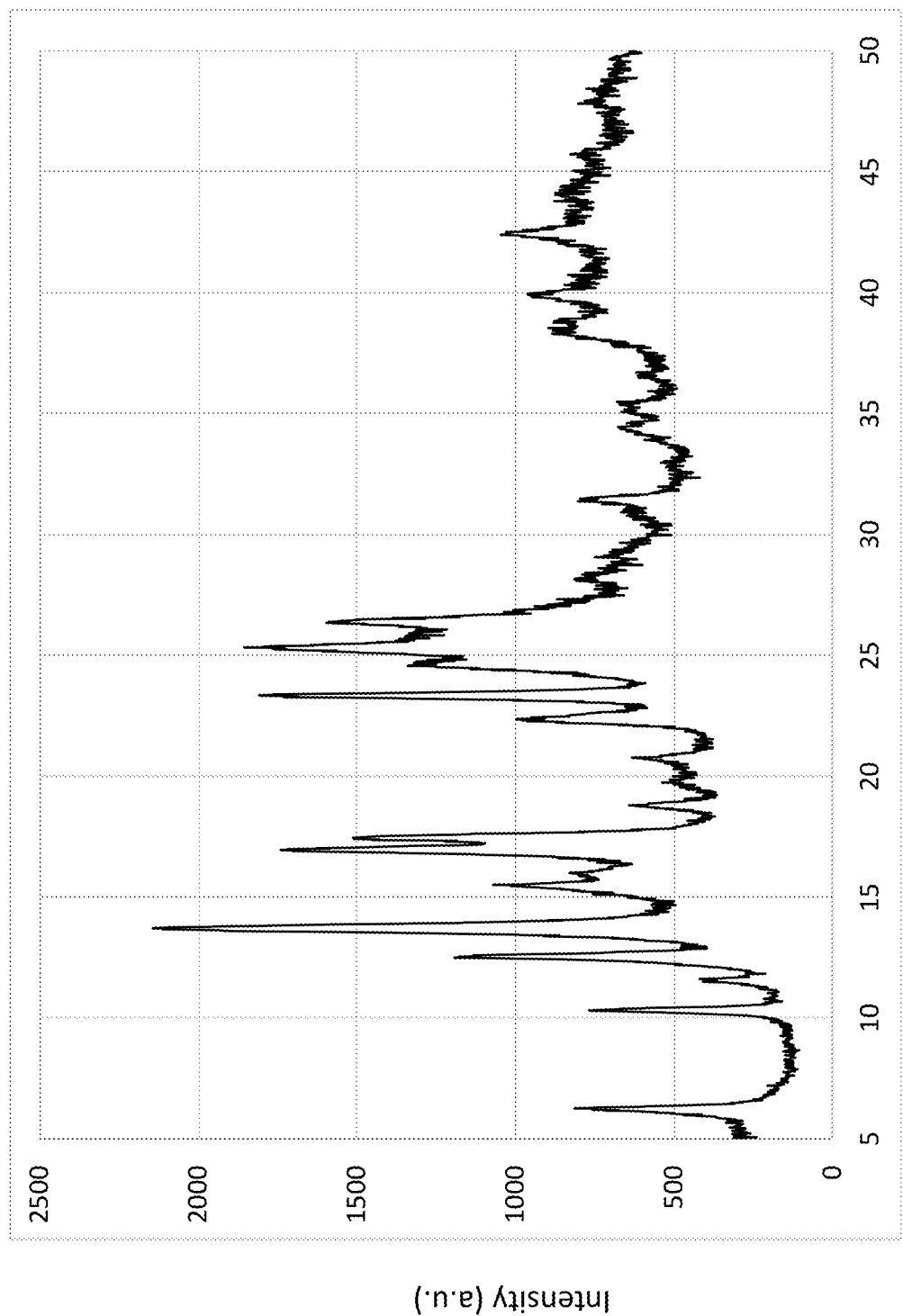
FIG. 15 illustrates the XRPD spectrum for microcrystalline $Zn(MLX)_2$ extracted from the MVL particles of a DepoMLX formulation.
Figure 16:
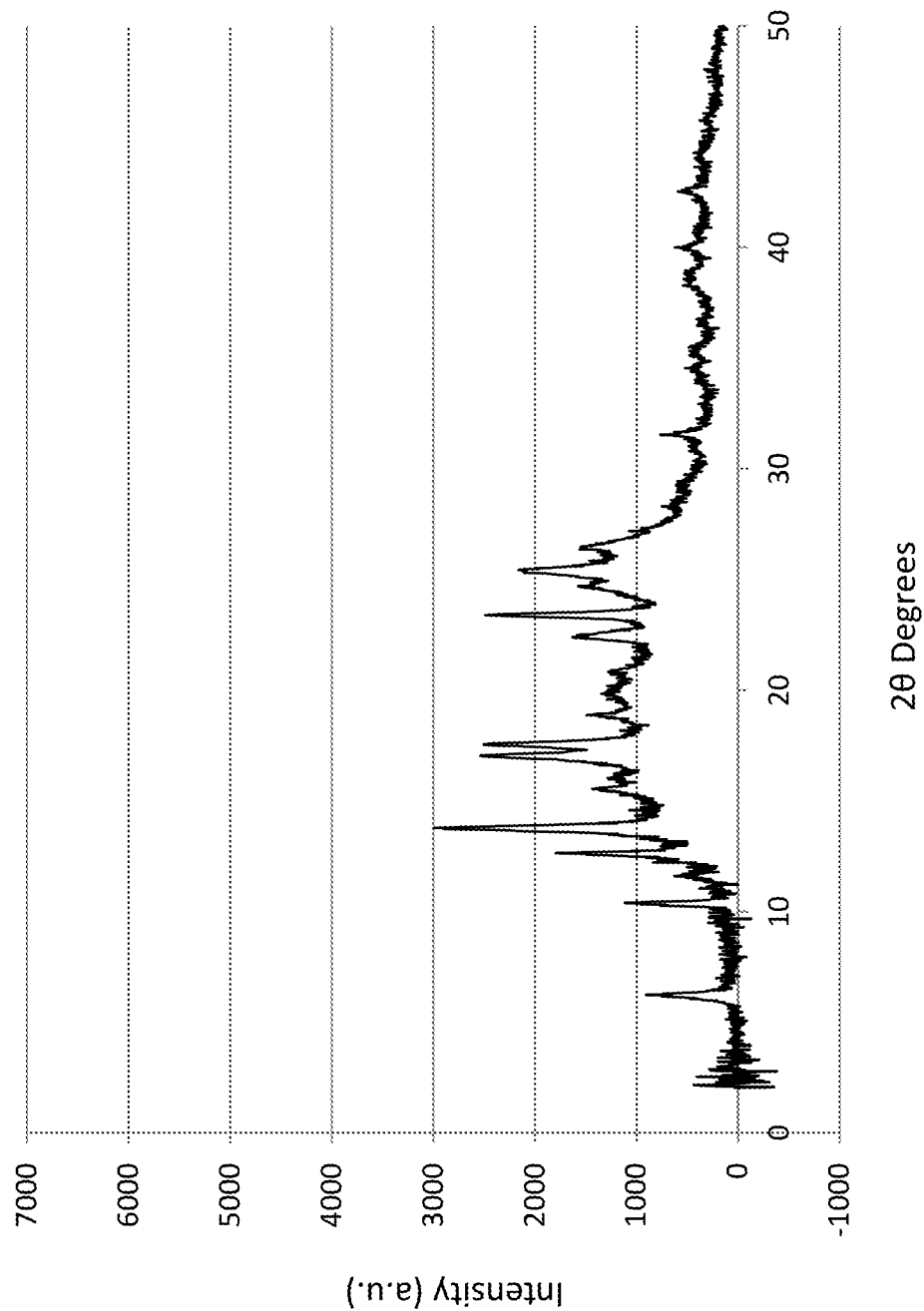
FIG. 16 illustrates the XRPD spectrum for microcrystalline $Zn(MLX)_2$ sediment representing unencapsulated zinc meloxicam complex microparticles obtained from a sample of DepoMLX.

FIG. 14A and FIG. 14B illustrate XRPD spectra for microcrystalline $Zn(MLX)_2$ microparticles prepared by a 1:1 process (FIG. 14A) and 2:1 process (FIG. 14B) as provided in Example 1, respectively. FIG. 15 illustrates the XRPD spectrum for microcrystalline $Zn(MLX)_2$ extracted from the MVL particles of a DepoMLX formulation prepared according to Formulation 1 of Example 1. In preparing the sample from which FIG. 15 was obtained, a formulation of DepoMLX was allowed to settle overnight, at which time the bottom-most sediment was drained off the bottom of the sample. The MVL particles were then subjected to a freeze-thaw cycle, and the resulting zinc meloxicam complex microparticles were washed in water, then washed in methanol, then washed in water, and finally freeze dried. The sediment was washed with water and freeze dried before being analyzed. FIG. 16 provides the XRPD spectrum for the bottom-most $Zn(MLX)_2$ sedimented microparticles. It is believed that the sediment represented the unencapsulated $Zn(MLX)_2$ in the sample. The XRPD spectrum of FIG. 16 included the same peaks as that of $Zn(MLX)_2$ that was encapsulated in MVLs (see FIG. 15). Thus, the crystalline form of the $Zn(MLX)_2$ was the same in the unencapsulated $Zn(MLX)_2$ and the MVL-encapsulated $Zn(MLX)_2$. The XRPD spectrum of the $Zn(MLX)_2$ sample corresponding to FIG. 15 included at least the peaks identified in Table 9.

Figure 17:
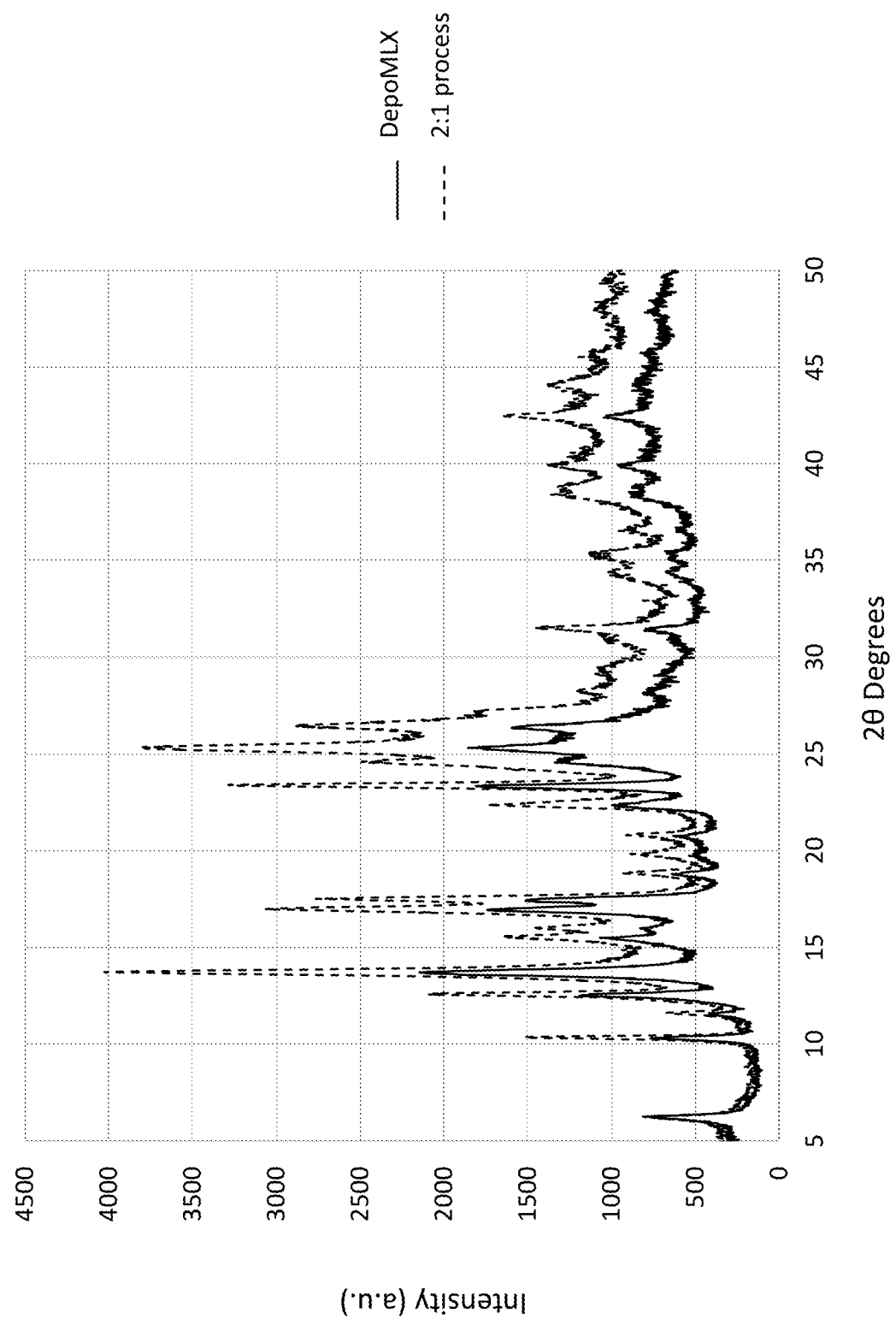
FIG. 17 provides comparative XRPD spectra for microcrystalline $Zn(MLX)_2$ extracted from the MVL particles of a DepoMLX formulation (solid line) and microcrystalline $Zn(MLX)_2$ prepared by a 2:1 process (dashed line).

FIG. 17 provides comparative XRPD spectra for microcrystalline $Zn(MLX)_2$ extracted from the MVL particles of a DepoMLX formulation (solid line) and microcrystalline $Zn(MLX)_2$ which was not encapsulated in MVLs (dashed line). As can be seen in FIG. 17, the XRPD spectra of $Zn(MLX)_2$ is the same before and after encapsulation in MVLs. Thus, the crystalline form of the $Zn(MLX)_2$ was not altered by encapsulated in MVLs.

The XRPD analyses were run in transmission mode on an X'pert Pro instrument with X'celerator detector using a standard XRPD method. The data were evaluated using the Highscore Plus software. Samples were mounted using a transmission sample holder. Samples were mounted as a thick film, to minimise preferred orientation effects, between Kapton film (Polyimide or other suitable film, e.g. Spectromembrane Cat. No. 3021) using a tin plated stainless steel spacer to afford a compact of 1 mm thickness and up to 1 cm in diameter. The conditions and parameters used in acquiring the XRPD spectra are listed in Table 10.

Figure 18A:
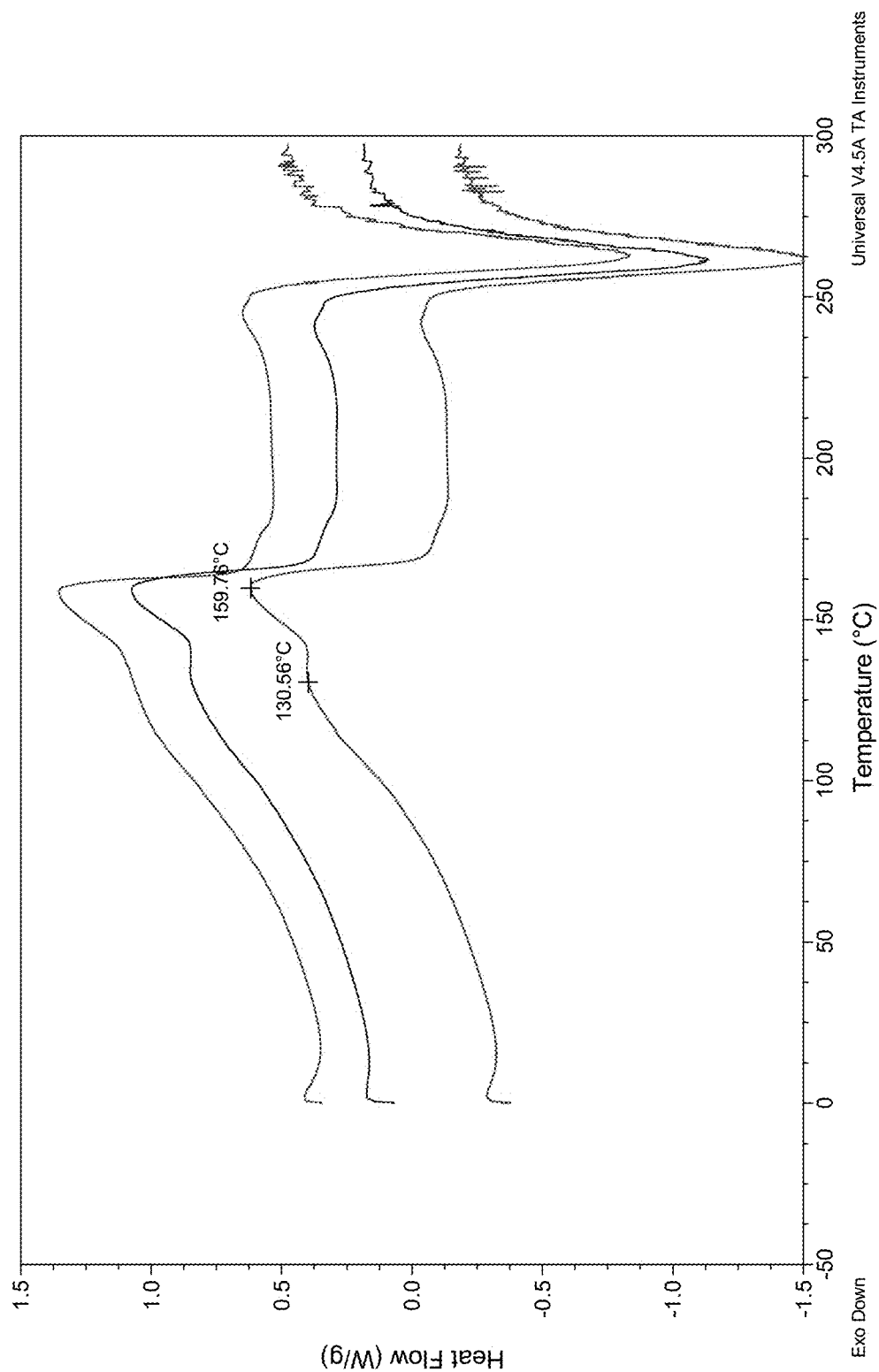
FIG. 18A, FIG. 18B, and FIG. 18C illustrate differential scanning calorimetry (DSC) and thermogravimetric analysis (TGA) data for microcrystalline $Zn(MLX)_2$.
Figure 18B:
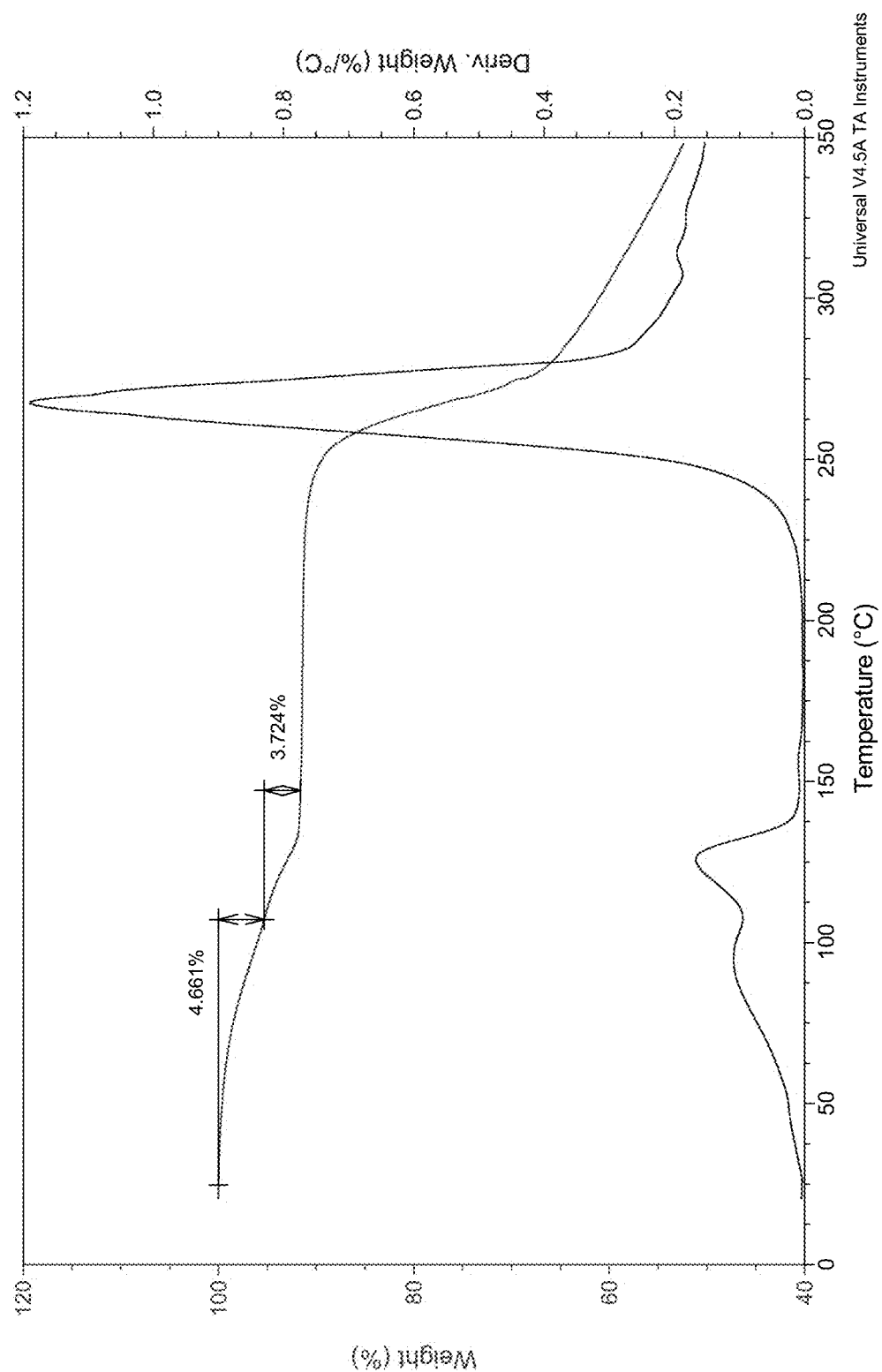
Figure 18C:
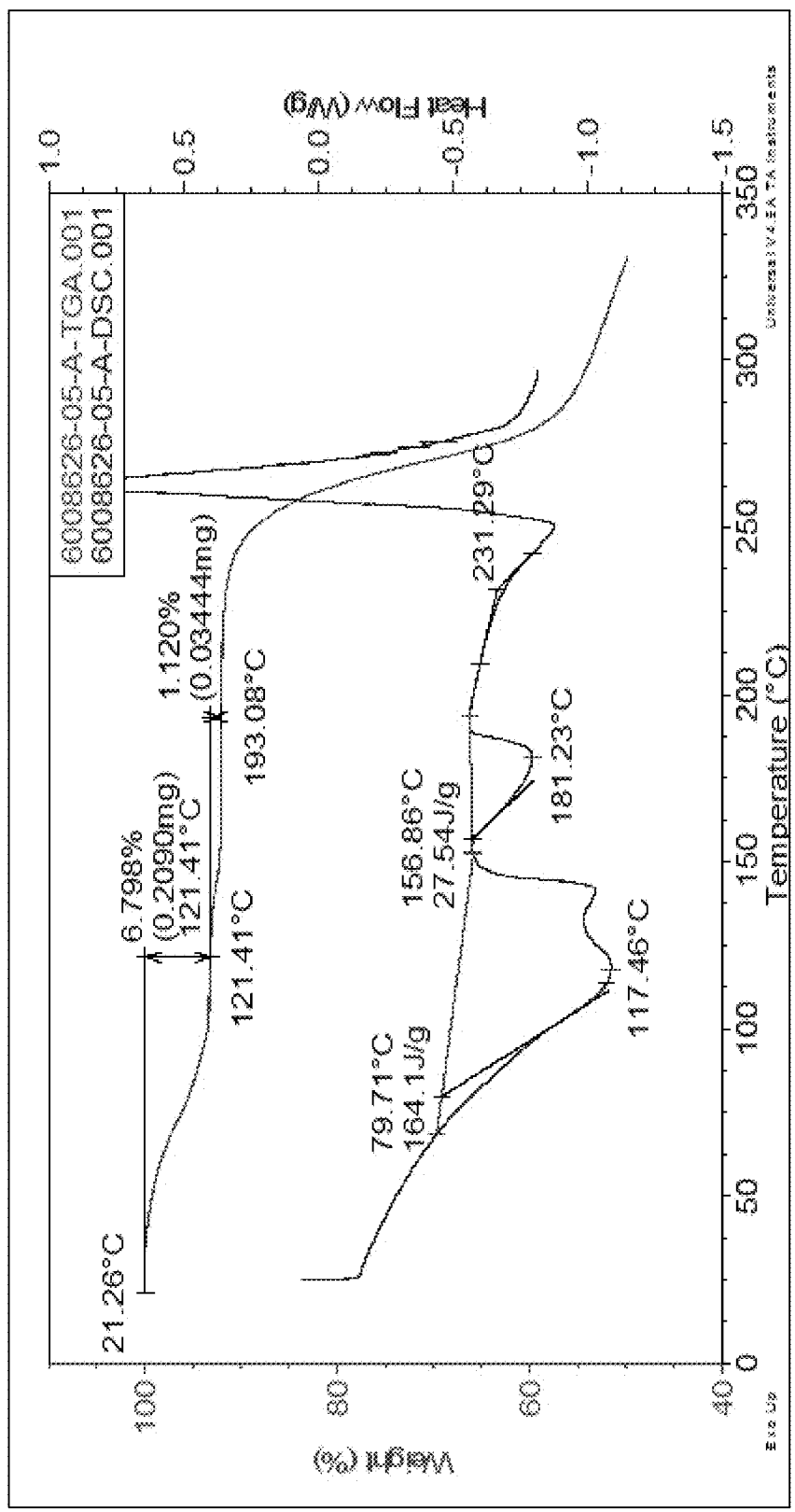

$Zn(MLX)_2$ and uncomplexed MLX showed distinct endotherms and gravimetric losses using differential scanning calorimetry (DSC) and thermogravimetric analysis (TGA), respectively. FIG. 18A, FIG. 18B, and FIG. 18C illustrate DSC and TGA data for microcrystalline $Zn(MLX)_2$ prepared by a 1:1 process according to Example 1. FIG. 18A provides three overlaid graphs illustrating DSC data for three samples, FIG. 18B provides a graph of TGA data including total weight lost upon heating, and the derivative of weight loss. FIG. 18C is a graph showing DSC and TGA data. The TGA/DSC overlay for $Zn(MLX)_2$ suggests that the two endotherms observed are most likely associated with water desorption and dehydration, respectively.

The TGA analyses were run on a TA Q5000 instrument using a standard TGA method. The data were evaluated using the Universal Analysis software. TGA method was as follows: heating rate was 10° C./min, balance purge gas at 10 mL/min, sample purge gas at 25 mL/min, temperature range was Amb ° C. to 350° C., the gas was nitrogen, sample amount was 2-20 mg, and the pan was Al (punched) non-hermetic. The DSC analyses were run on a TA Q2000 MDSC instrument. A standard DSC method was carried out and the method details were as follows: equilibration T 0° C., heating rate was 10° C./min, temperature range was 0° C.-300° C., gas was nitrogen, sample amount was typically 1-2 mg, and the pan type was TA non-hermetic.

Figure 19:
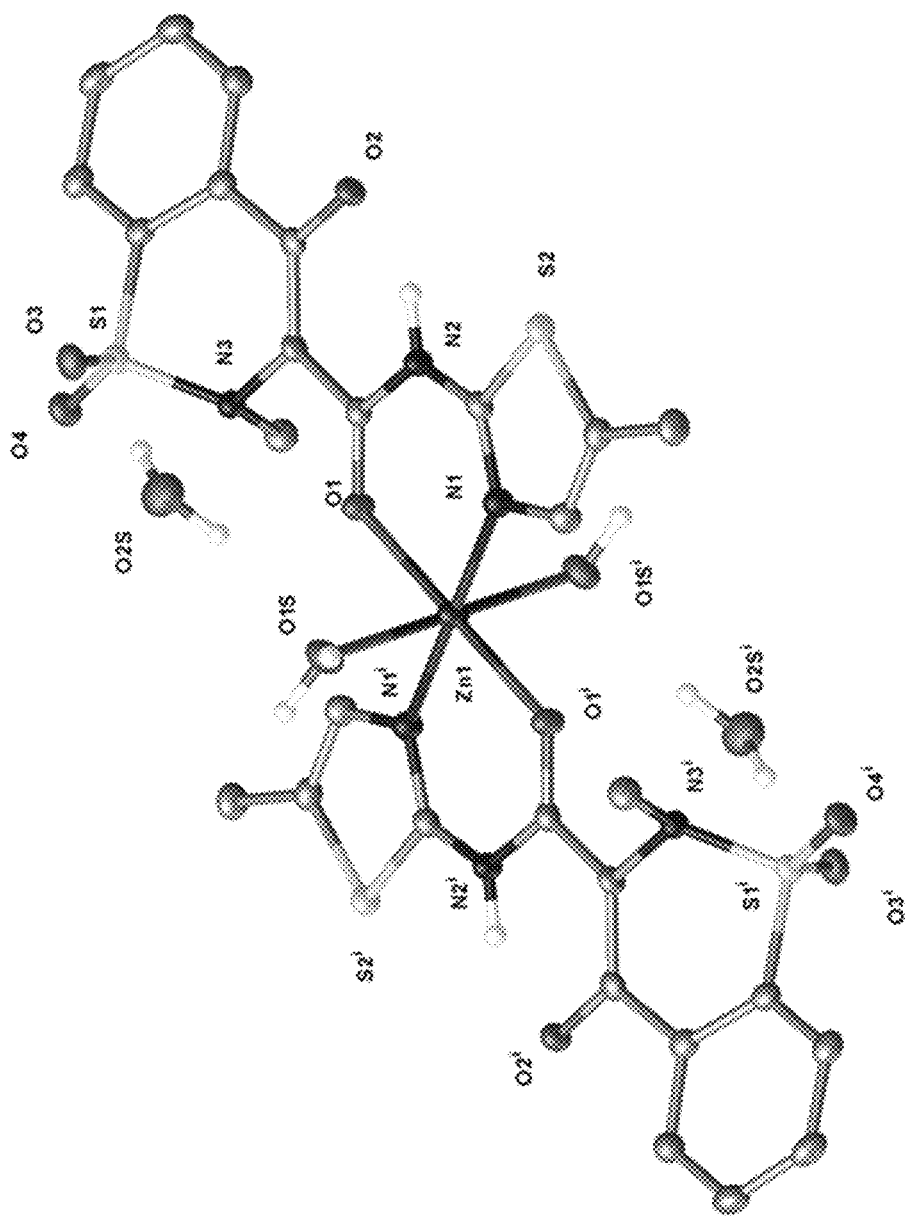
FIG. 19 depicts the crystal structure for $Zn(MLX)_2$ as microcrystalline $Zn(MLX)_2.4(H_2O)$ obtained using single crystal X-ray crystallography.

X-ray crystallography was performed on a single $Zn(MLX)_2$ microcrystal. Crystallography revealed that the $Zn(MLX)_2$ microcrystal consisted of a hydrated coordination compound containing two meloxicam molecules coordinated to one Zn. The $Zn(MLX)_2$ crystal contained four water molecules: two bound to zinc and two associated. FIG. 19 depicts the crystal structure for microcrystalline $Zn(MLX)_2$ as $Zn(MLX)_2.4(H_2O)$, as determined by X-ray crystallography.

TABLE 9

Subset of peaks in the XRPD spectrum of a sample of $Zn(MLX)_2$ extracted from the MVL particles of a DepoMLX formulation according to Example 9 and FIG. 15.

| Peak | 2θ (deg.) | Relative intensity (%) | Intensity (a.u.) |
|---|---|---|---|
| 1 | 6.3 | 38 | 813 |
| 2 | 10.3 | 36 | 768 |
| 3 | 12.5 | 56 | 1192 |
| 4 | 13.7 | 100 | 2144 |
| 5 | 16.9 | 81 | 1741 |
| 6 | 23.1 | 47 | 1007 |
| 7 | 23.3 | 84 | 1809 |
| 8 | 25.3 | 87 | 1856 |
| 9 | 26.3 | 74 | 1596 |
| 10 | 31.3 | 37 | 803 |
| 11 | 39.9 | 45 | 962 |
| 12 | 42.4 | 49 | 1046 |

TABLE 10

Instrumental conditions and parameters used in acquiring the XRPD spectra.

| Description | Value |
|---|---|
| 2-theta range | 2-45° |
| Step size [°2-theta] | 0.0167 |
| Time per step [sec] | 59.690 sec |
| Scan Mode | Continuous |
| Sample Movement | Spinning, 1.0 sec rotation time |
| Wavelength [nm] | Cu $K\alpha_1$ = 1.54060 $K\alpha_2$ = 1.54443 |
| X-ray Mirror | Inc. Beam Cu W/Si focusing MPD, Acceptance Angle 0.8° C., Length 55.3 mm |
| Slits Divergence/Antiscatter/Mask | Slit Fixed 1/2°/Slit Fixed 1/2°/10 mm Inc Beam Mask |
| Temperature/RH | Room temperature |
| Fixed Slits | Soller slits 0.02 rad on Incident and Diffracted beam |
| Detector type | X'Celerator (active length 2.122 degree) |
| Scanning mode | Transmission |
| Configuration | Transmission |
| Generator voltage/current | 40 Kv/40 mA |

Example 10. Dissolution Data for Unencapsulated $Zn(MLX)_2$ and DepoMLX

Figure 20:
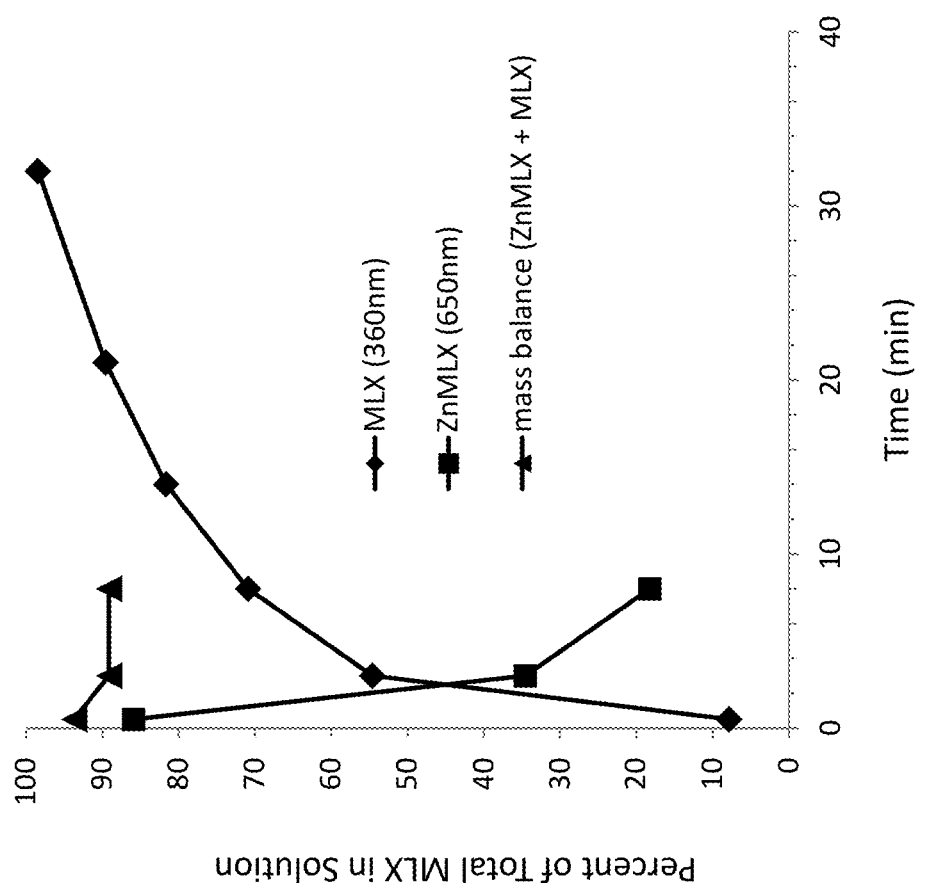
FIG. 20 illustrates data for dissolution in dog plasma of zinc meloxicam complex microparticles (squares—■).

A $Zn(MLX)_2$ suspension was diluted to 42 µg/mL in dog plasma (pH 7.4). The plasma was maintained at 37° C., under gentle agitation. The UV absorbances of the plasma at 360 nm and 660 nm were measured to determine the amount of dissolved MLX and undissolved $Zn(MLX)_2$, respectively. Standard absorption curves were used to quantitate the disappearance of undissolved $Zn(MLX)_2$ complex and the appearance of dissolved MLX. FIG. 20 shows the dissolution of the $Zn(MLX)_2$ and appearance of dissolved MLX during the plasma incubation. FIG. 20 provides graphs for the dissolution of zinc meloxicam complex microparticles (squares—■), dissolved and uncomplexed meloxicam (diamonds—♦), and the mass balance of dissolved and undissolved meloxicam (triangles—▲). $Zn(MLX)_2$ dissolved rapidly during the first 3 minutes, followed by a slower dissolution phase between 3 min to 35 min. The $Zn(MLX)_2$ dissolution was accompanied by an increase in the amount of free MLX in the solution. There was good mass balance between the amounts of starting $Zn(MLX)_2$ in the plasma and the changes in $Zn(MLX)_2$ and MLX concentrations in the plasma over time.

A second dissolution study was designed to compare the rates of dissolution of $Zn(MLX)_2$ suspension and DepoMLX. The DepoMLX sample was prepared according to Formulation 3 of Example 1. Suspensions of $Zn(MLX)_2$ complex microparticles, and DepoMLX, respectively, were diluted into three different buffers, each adjusted to pH 7.4 to simulate physiological pH. The final concentration in each buffer was between 60-100 µg/mL (below the solubility limit for MLX at pH 7.4). Each mixture was incubated in buffer at 37° C. with gentle agitation by rocking. At various times, samples were removed and filtered through 5000 molecular weight cutoff (MWCO) spin filters. The filtrates were assayed to determine the amount of dissolved MLX present in the supernatants. The appearance of dissolved MLX from suspended, unencapsulated $Zn(MLX)_2$ was rapid, whereas only about 30% to 50% of the MLX appeared over 2-4 days from DepoMLX.

Figure 21A:
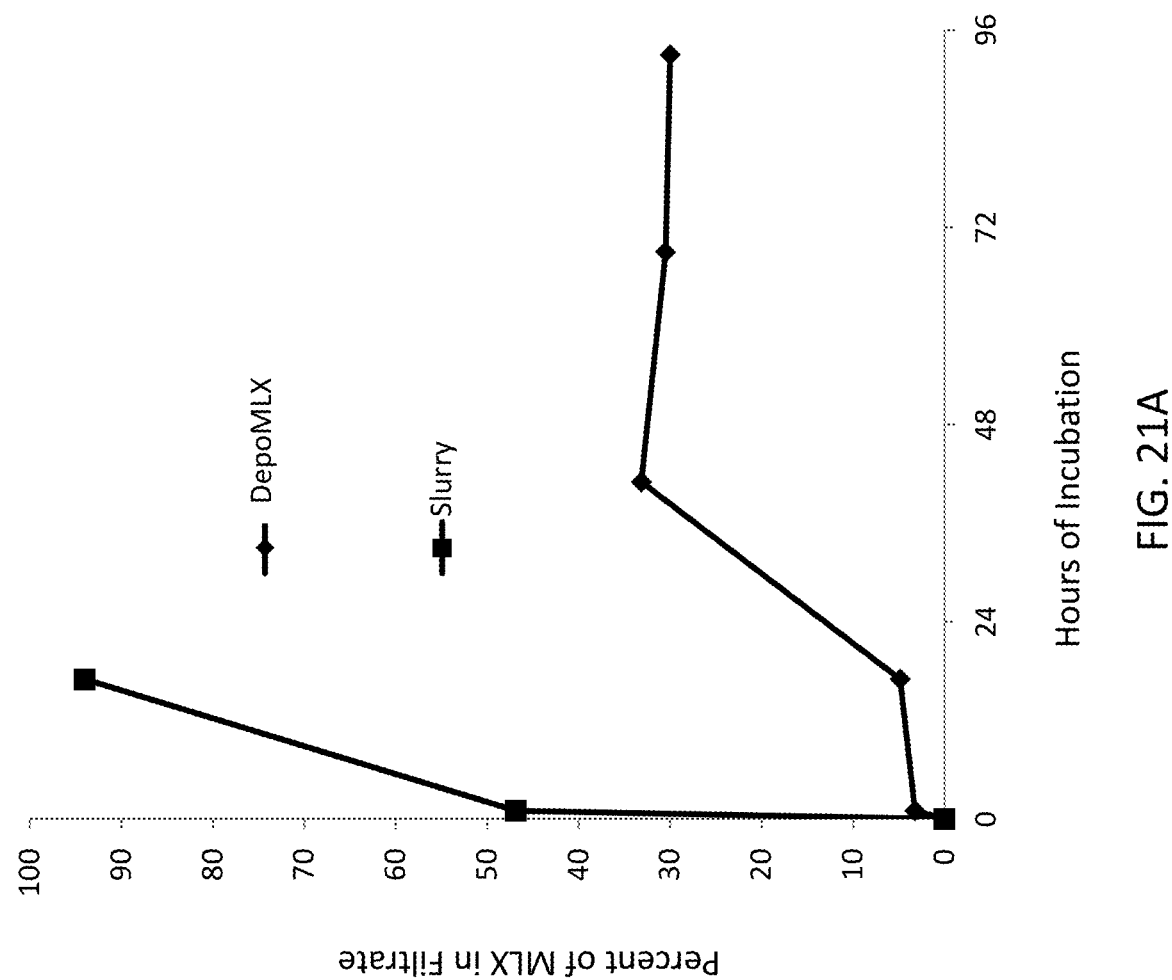
FIG. 21A, FIG. 21B, and FIG. 21C illustrate comparative data for dissolution of zinc meloxicam complex microparticle as DepoMLX (diamonds—♦) and as an unencapsulated suspension (squares—▲) into various buffers at pH 7.4.
Figure 21B:
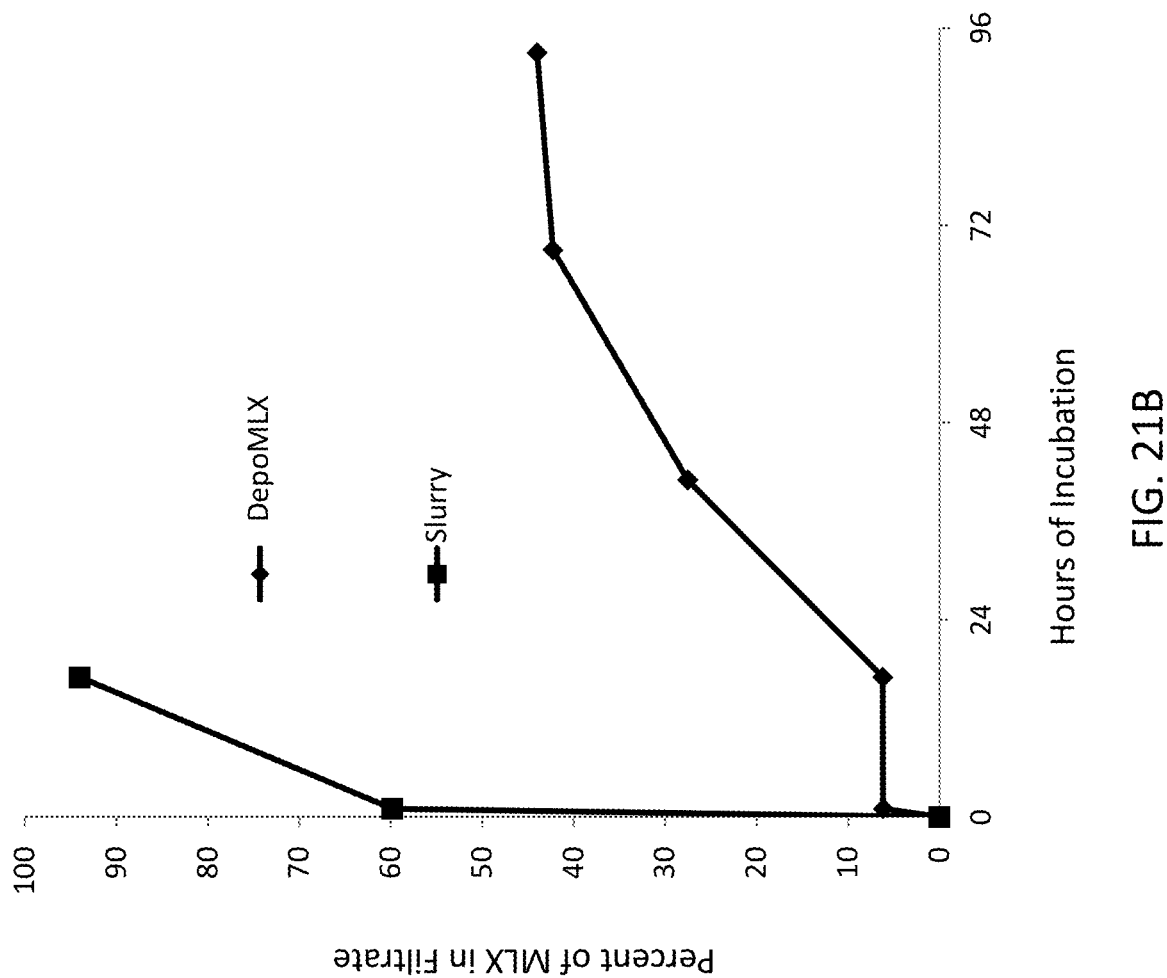
Figure 21C:
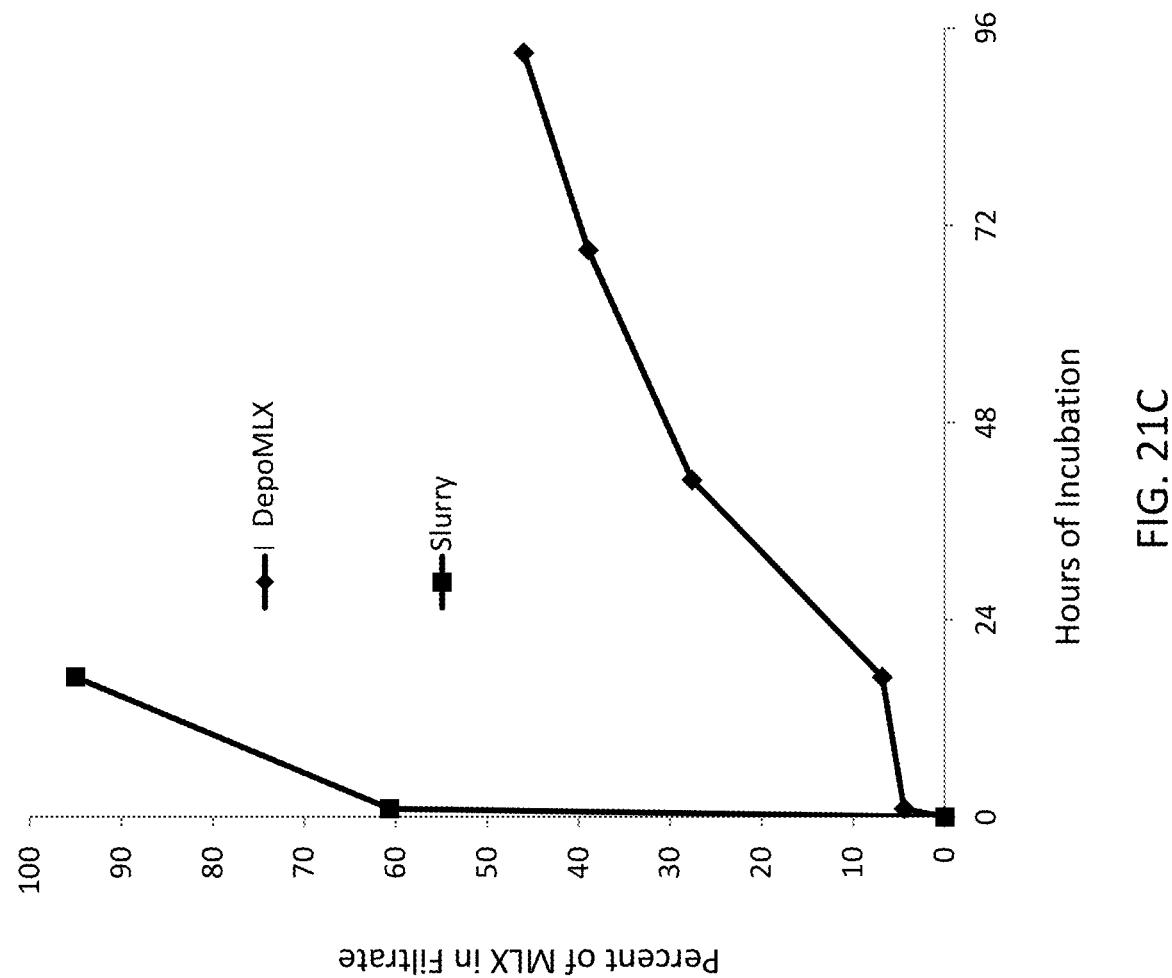

Thus, $Zn(MLX)_2$ suspensions dissolved very quickly following dilution into the buffers adjusted to physiological pH, while the $Zn(MLX)_2$ encapsulated as DepoMLX was released very slowly over 4 days. These findings support the hypothesis that DepoMLX will prolong the presence of $Zn(MLX)_2$ in the body and/or in the bloodstream following in vivo administration, and that $Zn(MLX)_2$ released from DepoMLX particles will dissolve in a physiological environment to produce a pharmaceutically active MLX compound. FIG. 21A, FIG. 21B, and FIG. 21C illustrate comparative data for the dissolution of zinc meloxicam complex microparticles as DepoMLX (diamonds—♦) and as an unencapsulated suspension (squares—■) into various buffers at pH 7.4. In FIG. 21A, the buffer is $NaHPO_4$, in FIG. 21B the buffer is 50 mM HisTA, while in FIG. 21C the buffer is 100 mM HisTA.

Example 11. Pharmacokinetic Studies in Rats

Figure 22A:
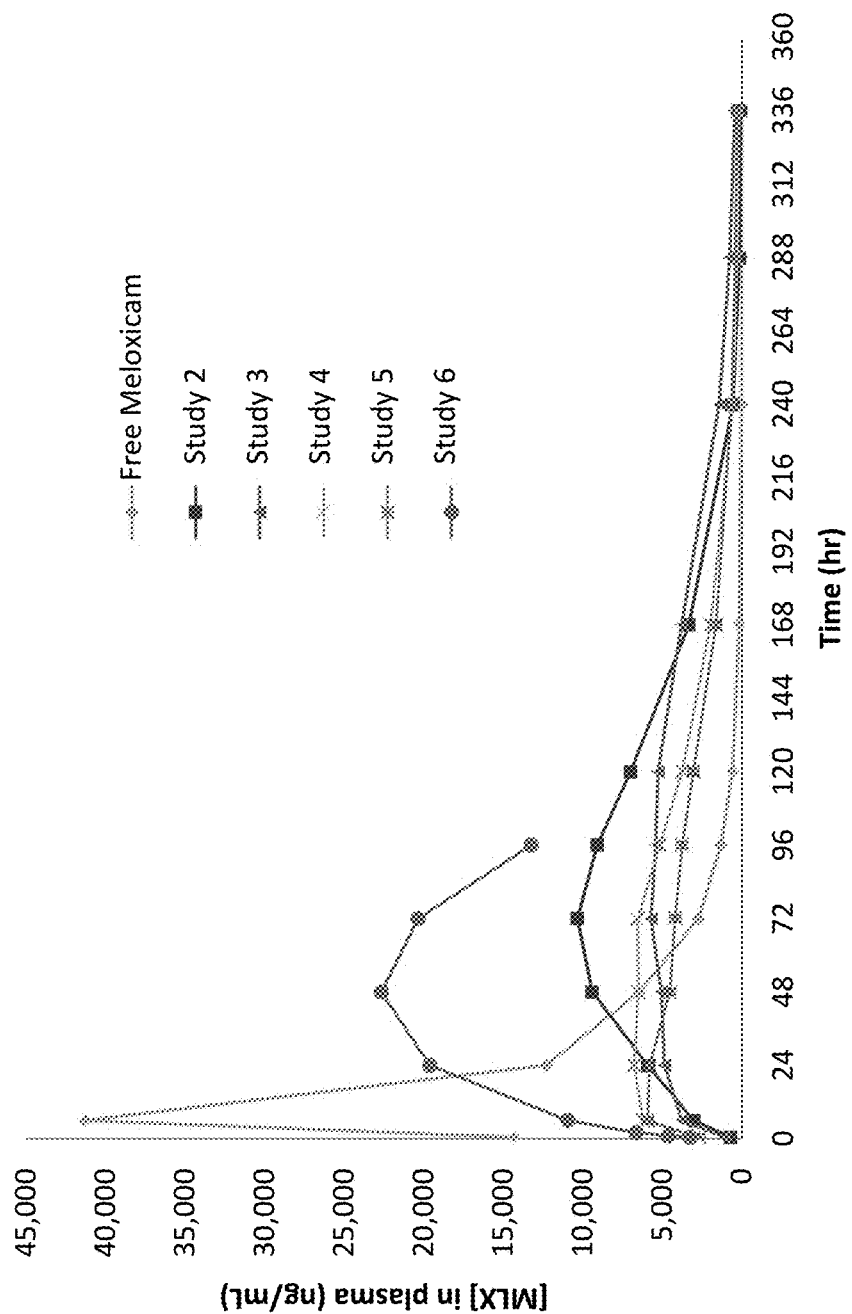
FIG. 22A, FIG. 22B, and FIG. 22C illustrate pharmacokinetic data following subcutaneous injection in rats for various formulations of DepoMLX, according to Example 11.
Figure 22B:
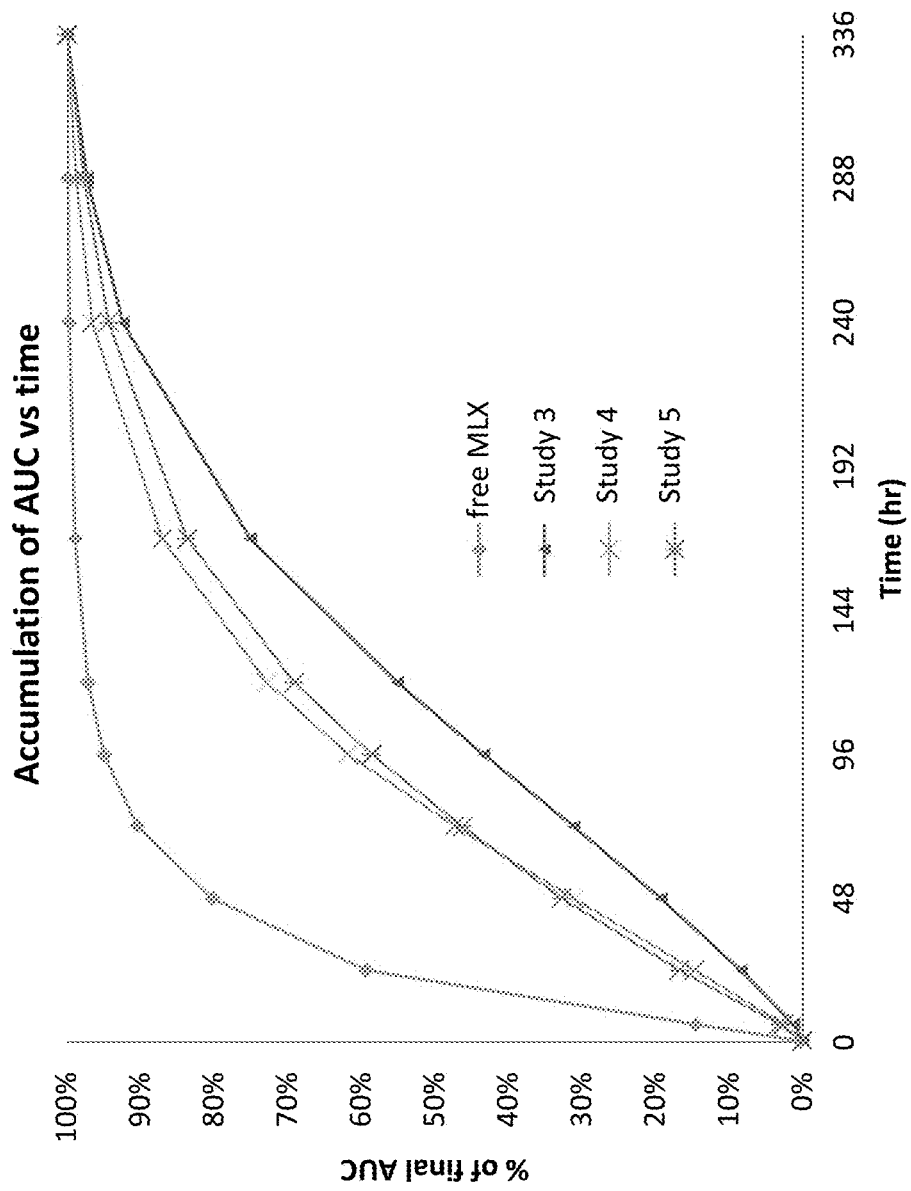

PK studies in rats of high potency formulations (~2.4 mg/ml at 50% ppv) manufactured according to Formulations 1 and 3 of Example 1 were carried out. Sprague-Dawley rats were injected subcutaneously with free MLX, DepoMLX prepared according to Formulation 1 of Example 1, or DepoMLX prepared according to Formulation 3 of Example 1, but with the given MLX potency. The release of MLX into plasma was measured, and AUC determined. A summary of the experiments and results is provided in Table 11. MLX blood plasma concentration data is illustrated in FIG. 22A. FIG. 22B provides data for AUC accumulation over time for the formulations of Studies 3, 4, and 5. Development scale formulations produced 0.6-0.8 L of MVLs at the indicated potency, while commercial scale formulations produced 40-50 L of MVLs at the indicated potency.

Figure 22C:
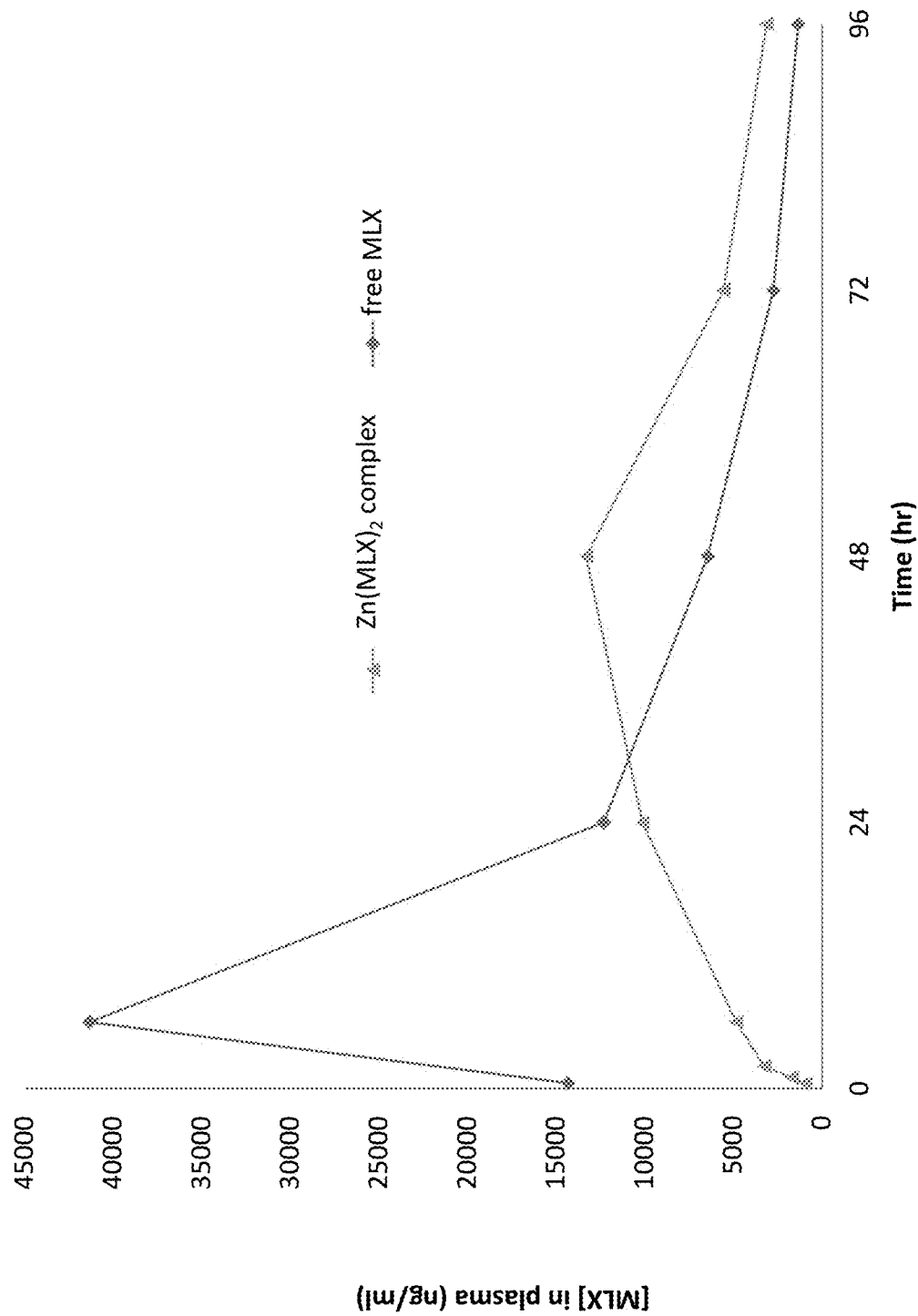

Additionally, zinc meloxicam complex microparticles prepared by a 1:1 process according to Formulation 1 of Example 1 were prepared on a scale of about 10 L (see Table 1A). The unencapsulated zinc meloxicam complex microparticles were administered subcutaneously to rats, and the release of MLX into plasma was measured. A summary of the experiment compared to the release of free meloxicam is provided in Table 12. MLX blood plasma concentration data for this experiment is illustrated in FIG. 22C.

TABLE 11

Studies determining release of free and encapsulated meloxicam into blood plasma following subcutaneous (SC) injection into rats for various formulations.

| Study | Formulation | Scale | Potency of MLX (mg/ml) | Dose vol. (mL) | Admin. route | $AUC_{0\text{-}last}$ (ng*h/mL) |
|---|---|---|---|---|---|---|
| 1 | Free MLX | n/a | 2.4 | 1 | SC | 1077989 |
| 2 | Formulation 3 | Development | 2.5 | 1 | SC | 1353556 |
| 3 | Formulation 3 | Commercial | 2.7 | 1 | SC | 1094430 |
| 4 | Formulation 3 | Commercial | 2.3 | 1 | SC | 971885.5 |
| 5 | Formulation 3 | Commercial | 2.6 | 1 | SC | 777361.5 |
| 6 | Formulation 1 | Development | 2.4 | 1 | SC | Not determined |

TABLE 12

Studies determining release of free and zinc-complexed meloxicam into blood plasma following subcutaneous (SC) injection into rats.

| Study | Formulation | Potency of MLX (mg/ml) | Dose vol. (mL) | Admin. route |
|---|---|---|---|---|
| 7 | Free MLX | 2.4 | 1 | SC |
| 8 | Zinc meloxicam complex microparticles | 2.7 | 1 | SC |

Example 12. Pharmacokinetic Studies in Beagle Dogs

Figure 23:
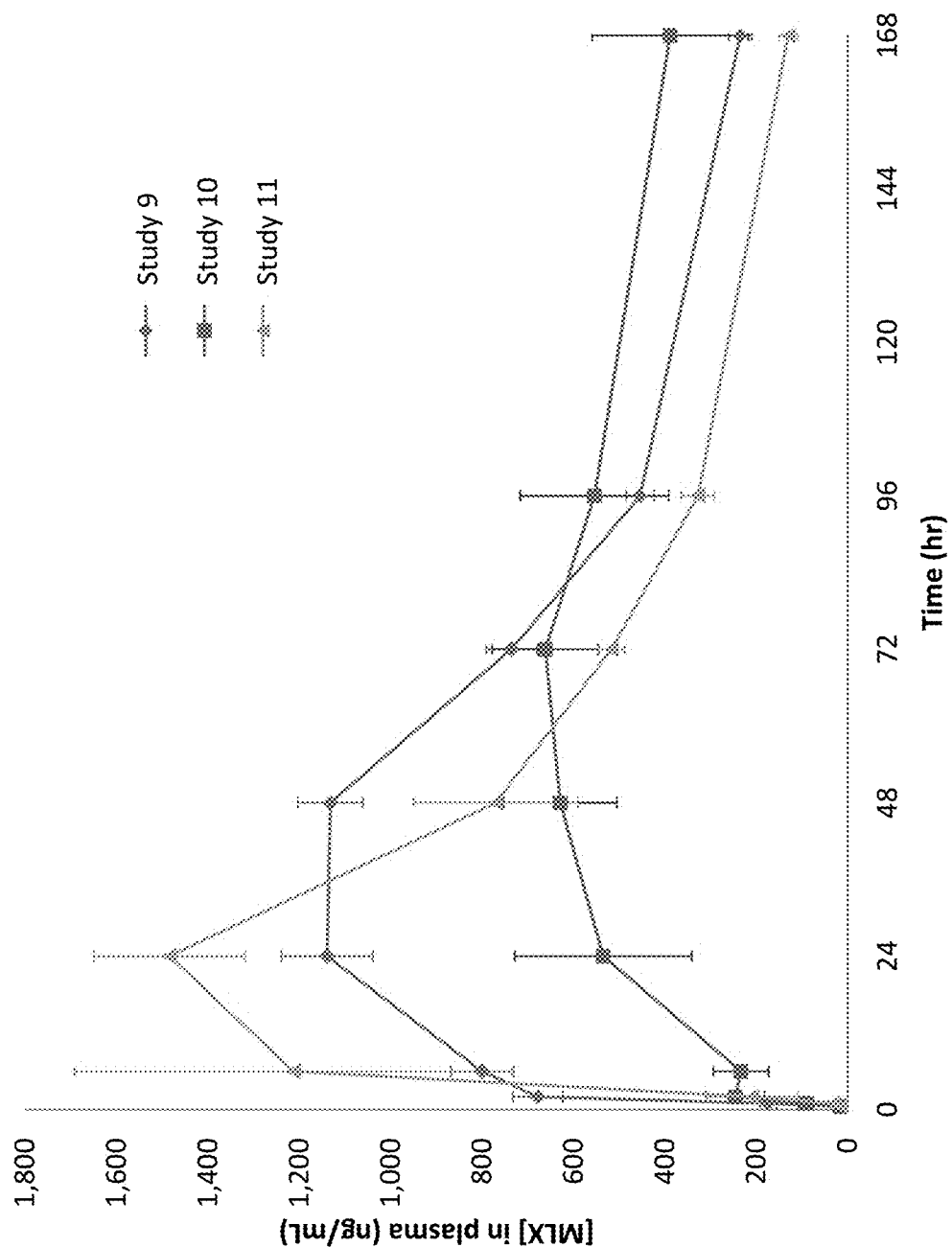
FIG. 23 illustrates data for pharmacokinetic data for various formulations of DepoMLX following subcutaneous injection in beagle dogs, according to Example 12.

PK studies in beagle dog of high potency formulations (2.4-3.0 mg/ml at 50% ppv) manufactured according to Formulations 1 and 3 of Example 1 were carried out. Male beagle dogs were injected subcutaneously with DepoMLX prepared according to Formulation 1 of Example 1, or DepoMLX prepared according to Formulation 3 of Example 1, but with the given MLX potency. The release of MLX into plasma was measured. A summary of the experiments and results is provided in Table 13. MLX blood plasma concentration data is illustrated in FIG. 23. Development scale formulations produced 0.6-0.8 L of MVLs at the indicated potency, while commercial scale formulations produced 40-50 L of MVLs at the indicated potency.

TABLE 13

Studies determining meloxicam release from DepoMLX into blood plasma following subcutaneous (SC) injection into beagle dogs for various formulations.

| Study | Formulation | Scale | Dose (mg/Kg) | Potency of MLX (mg/ml) | Dose vol. (mL/Kg) | Admin. route |
|---|---|---|---|---|---|---|
| 9 | Formulation 1 | Development | 0.6 | 2.4 | 0.25 | SC |
| 10 | Formulation 3 | Commercial | 0.6 | 2.7 | 0.22 | SC |
| 11 | Formulation 3 | Development | 0.6 | 3.0 | 0.20 | SC |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

In another embodiment, any one of the above described embodiments can be used alone or in combination with any one or more of the above described embodiments.

What is claimed is:

1. A formulation of multivesicular liposomes (MVLs) having multiple nonconcentric internal compartments, comprising:
   a zinc meloxicam complex having the formula $Zn(MLX)_2$, and one or more pH adjusting agents encapsulated in a first aqueous phase of the multivesicular liposomes; and
   lipid components comprising at least one amphipathic lipid selected from phosphatidyl choline or salts thereof, phosphatidyl glycerol or salts thereof, or combinations thereof, and at least one neutral lipid;
   wherein at least a portion of the zinc meloxicam complex forms a suspension of microparticles in the first aqueous phase.

2. The formulation of claim 1, wherein the zinc meloxicam complex has the formula $Zn(MLX)_2(OH_2)_2$.

3. The formulation of claim 1, wherein at least a portion of the zinc meloxicam complex is in a microcrystalline form.

4. The formulation of claim 3, wherein the microcrystalline zinc meloxicam complex is present as $Zn(MLX)_2 \cdot 4(H_2O)$.

5. The formulation of claim 1, wherein the microparticles have a median particle diameter of less than 2 μm.

6. The formulation of claim 1, wherein the pH adjusting agents comprise one or more organic acids, one or more organic bases, or combinations thereof.

7. The formulation of claim 6, wherein said one or more organic acids comprise tartaric acid.

8. The formulation of claim 6, wherein said one or more organic bases comprise lysine or histidine, or both.

9. The formulation of claim 1, wherein the pH of the first aqueous phase of the multivesicular liposomes is from about 5.4 to about 6.6.

10. The formulation of claim 1, wherein the first aqueous phase of the multivesicular liposomes further comprises one or more tonicity agents.

11. The formulation of claim 10, wherein the tonicity agents comprise sucrose.

12. The formulation of claim 10, wherein the osmolality of the first aqueous phase of the multivesicular liposomes is from about 250 mOsm/kg to about 350 mOsm/kg.

13. The formulation of claim 1, having a packed particle volume of 40-60%.

14. The formulation of claim 1, wherein the lipid components comprise at least one triglyceride.

15. The formulation of claim 1, wherein the phosphatidyl glycerol is dipalmitoyl phosphatidyl glycerol (DPPG).

16. The formulation of claim 1, wherein the phosphatidyl choline is dierucoyl phosphatidyl choline (DEPC).

17. The formulation of claim 14, wherein the at least one triglyceride is tricaprylin.

18. The formulation of claim 1, wherein the lipid components further comprise cholesterol.

19. The formulation of claim 1, wherein the multivesicular liposomes have a median particle diameter ranging from about 10 μm to about 50 μm.

20. The formulation of claim 1, wherein the concentration of the meloxicam in the multivesicular liposome formulation is from about 1 mg/mL to about 25 mg/mL.

21. The formulation of claim 20, wherein the concentration of the meloxicam in the multivesicular liposome formulation is from about 2.0 mg/mL to about 7.0 mg/mL.

22. The formulation of claim 3, wherein the microcrystalline form of the zinc meloxicam complex exhibits 20 characteristic peaks in an XRPD spectrum of about 6.3, about 10.3, about 12.5, about 13.7, about 16.9, about 23.1, about 23.3, about 25.3, about 26.3, about 31.3, about 39.9, and about 42.4 degrees.

23. The formulation of claim 1, wherein the formulation further comprises unencapsulated meloxicam or zinc meloxicam complex.

24. A method of treating pain or inflammation, comprising administering a formulation of claim 1 to a subject in need thereof.

25. The method of claim 24, wherein said subject is suffering from postoperative pain from a surgical site or pain from an acute or chronic condition.

26. The method of claim 24, wherein said subject is suffering from arthritis.

27. The method of claim 24, wherein the formulation is administered by intraarticular, intramuscular, subcutaneous, intraperitoneal, intraocular, or intrathecal injection, or administered topically, or by wound infiltration or instillation.

28. A multivesicular liposomes formulation prepared by a process comprising:
    preparing a first aqueous suspension of zinc meloxicam complex microparticles by mixing a first solution comprising meloxicam, a second solution comprising a zinc salt, and one or more pH adjusting agents to form a zinc meloxicam complex microparticle suspension;
    preparing a first emulsion by mixing the first aqueous suspension with a water-immiscible organic solvent phase comprising a volatile organic solvent, said organic solvent phase comprising at least one amphipathic lipid selected from phosphatidyl choline or salts thereof, phosphatidyl glycerol or salts thereof, or combinations thereof, and at least one neutral lipid;
    combining said first emulsion and a second aqueous phase to provide a second emulsion; and
    substantially removing the organic solvent from the second emulsion.

29. The multivesicular liposomes formulation of claim 28, wherein the zinc meloxicam complex microparticles have a median particle diameter of less than about 2 μm.

30. The multivesicular liposomes formulation of claim 28, the one or more pH adjusting agents of the first aqueous suspension comprise tartaric acid, lysine or histidine, or combinations thereof.

31. The multivesicular liposomes formulation of claim 28, wherein the pH of the first aqueous suspension is from about 5.6 to about 6.6.

32. The multivesicular liposomes formulation of claim 28, wherein the zinc meloxicam complex microparticle suspension has a pH of about 4.5 to about 8.0.

33. The multivesicular liposomes formulation of claim 28, wherein the pH of the second aqueous phase is from about 5 to about 9.0.

34. The multivesicular liposomes formulation of claim 28, further comprising exchanging the second aqueous phase with a suspending medium having a pH of 5.5 to 6.5.

* * * * *